United States Patent [19]

Cheng et al.

US005435990A

[11] Patent Number: 5,435,990
[45] Date of Patent: Jul. 25, 1995

[54] MACROCYCLIC CONUGATES AND THEIR USE AS DIAGNOSTIC AND THERAPEUTIC AGENTS

[75] Inventors: Roberta C. Cheng; William A. Fordyce; William F. Goeckleler, all of Midland; William J. Kruper, Jr., Sanford, all of Mich.; Richard K. Frank; Joseph R. Garlich, both of Lake Jackson, Tex.; Garry E. Kiefer; Kenneth McMillan, both of Richwood, Tex.; Jaime Simon, Angleton, Tex.; David A. Wilson, Richwood, Tex.; Sharon Braughman, Irvine, Calif.

[73] Assignee: The Dow Chemical Company, Midland, Mich.

[21] Appl. No.: 962,168

[22] Filed: Oct. 15, 1992

Related U.S. Application Data

[60] Division of Ser. No. 370,956, Jun. 21, 1989, abandoned, which is a continuation-in-part of Ser. No. 211,496, Jun. 24, 1988, abandoned.

[51] Int. Cl.⁶ .................. A61K 51/10; A61M 36/06; C07K 16/30
[52] U.S. Cl. ............................. 424/153; 424/179.1; 424/183.1; 530/388.85; 530/391.1; 530/391.3; 530/391.5; 530/391.7; 530/391.9
[58] Field of Search ............ 530/388.85, 391.1, 391.3, 530/391.5, 391.7, 391.9; 424/1, 1.9, 85.8, 85.91

[56] References Cited

U.S. PATENT DOCUMENTS

| | | | |
|---|---|---|---|
| 4,454,106 | 6/1984 | Gansow et al. | 424/1.1 |
| 4,472,509 | 8/1984 | Gansow et al. | 436/548 |
| 4,647,447 | 3/1987 | Gries et al. | 424/9 |
| 4,678,667 | 7/1987 | Meares et al. | 424/85.91 |
| 4,885,363 | 12/1989 | Tweedle et al. | 540/465 |
| 4,994,560 | 2/1991 | Kruper, Jr. et al. | 534/10 |
| 5,006,643 | 4/1991 | Fazio et al. | 424/85.91 |
| 5,057,302 | 10/1991 | Johnson et al. | 424/1.1 |

FOREIGN PATENT DOCUMENTS

| | | | |
|---|---|---|---|
| 232751 | 8/1987 | European Pat. Off. | C07D 273/00 |
| 0238196 | 9/1987 | European Pat. Off. | A61K 49/00 |
| 255471 | 2/1988 | European Pat. Off. | C07D 257/02 |
| 279307 | 8/1988 | European Pat. Off. | C07C 101/28 |
| 292689 | 11/1988 | European Pat. Off. | C07D 257/02 |
| 296522 | 12/1988 | European Pat. Off. | C07D 257/02 |
| 8403698 | 9/1984 | WIPO | C07K 164/04 |
| 8901475 | 2/1989 | WIPO | C07D 255/02 |

OTHER PUBLICATIONS

Desreux et al. (1988) Nucl. Med. Biol. 15 (1): 9–15
Sherry et al (1989) Inorg. Chem. 28: 620–622.
Washburn et al. (1988) Nucl. Med. Biol. 15 (6): 707–711.
Morrison and Boyd in *Organic Chemistry* 3rd Ed. Allyn and Bacon, Inc. Boston 1973 pp. 360–363.
Tweedle et al Proceed. 34th Ann. Nat. 28(4):705 abstract No. 626, 1987.
Forsberg et al. (1971) Inorganic Chemistry 10(12):2656–2660.
Forsberg et al. (1969) Inorg. Chem. 8(4):883–888.
Borch et al. (1971) J. Am. Chem. Soc. 93(12):2897–04.
Mattson et al. (1990) J. Org. Chem. 55:2552–2554.
Westerberg et al (1989) J. Med. Chem. 32(1):236–244.
Franz et al (1987) Nucl. Med. Biol. 14(5):479–484.
Muraro et al. (1988) Cancer Research 48:4588–4596.
Colcher et al. (1988) Cancer research 48:4597–4603.

(List continued on next page.)

*Primary Examiner*—Christine M. Nucker
*Assistant Examiner*—M. P. Woodward
*Attorney, Agent, or Firm*—Karen L. Kimble

[57] ABSTRACT

A group of functionalized macrocyclic polyaminocarboxylate chelants that form complexes with rare earth-type metal ions are disclosed. The complexes, covalently attached to an antibody or antibody fragment, can be used for therapeutic and/or diagnostic purposes for cancer.

40 Claims, 34 Drawing Sheets

OTHER PUBLICATIONS

Copy of application 07/547,336.
Roselli et al. (1989) J. Nucl. Med. 30:672–682.
Mears et al., *Anal. Biochem.* 142, 68–78 (1984).
Krejcarek et al., *Biochem. and Biophys. Res comm.* 77, 581–585 (1977).
Brechbiel et al., *Inorg. Chem.* 25, 2772–2781 (1986).
Moi et al., *Inorg. Chem.* 26, 3458–3463 (1987).
P. L. Carney et al., 3rd Int'l. Conf. on Monoclonal Antibodies for Cancer, San Diego, Calif. (Feb. 4–6, 1988).
D. K. Johnson et al., Florida Conf. on Chem. in Biotechnology, Palm Coast, Fla. (Apr. 26–29, 1988).
Moi et al. *J. Am. Chem. Soc.* 110, 6266–6267 (1988).
Brittain et al., *Inorg. Chem.* 23, 4459–4466 (1984).
J. F. Desreux et al., *Nucl Med. Biol.* 15 (1), 9–15 (1988).
Arzneimittel Wirkungen, pp. 46–55 (1981) (in German)
*Advanced Organic Chemistry*, Jerry March, 1984, pp. 145–150.

MACROCYCLIC CONGUGATES AND THEIR USE AS DIAGNOSTIC AND THERAPEUTIC AGENTS

CROSS-REFERENCE TO RELATED APPLICATION

This is a divisional of application Ser. No. 07/370,956, now abandoned, filed Jun. 21, 1989, which is a Continuation-in-part of application Ser. No. 07/211,496, filed Jun. 24, 1988, now abandoned.

BACKGROUND OF THE INVENTION

Functionalized chelants, or bifunctional coordinators, are known to be capable of being covalently attached to an antibody having specificity for cancer or tumor cell epitopes or antigens. Radionuclide complexes of such antibody/chelant conjugates are useful in diagnostic and/or therapeutic applications as a means of conveying the radionuclide to a cancer or tumor cell. See, for example, Meares et al., Anal. Biochem. 142, 68-78, (1984); and Krejcarek et al., Biochem. and Biophys. Res. Comm. 77, 581-585 (1977).

Aminocarboxylic acid chelating agents have been known and studied for many years. Typical of the aminocarboxylic acids are nitrilotriacetic acid (NTA), ethylenediaminetetraacetic acid (EDTA), hydroxyethylethylenediaminetriacetic acid (HEDTA), diethylenetriaminepentaacetic acid (DTPA), trans-1,2-diaminocyclohexanetetraacetic acid (CDTA) and 1,4,7,10-tetraazacyclododecanetetraacetic acid (DOTA). Numerous bifunctional chelating agents based on aminocarboxylic acids have been proposed and prepared. For example the cyclic dianhydride of DTPA [Hnatowich et al. Science 220, 613-615, (1983); U.S. Pat. No. 4,479,930] and mixed carboxycarbonic anhydrides of DTPA [Gansow, U.S. Pat. Nos. 4,454,106 and 4,472,509; Krejcarek et al., Biochem. and Biophys. Res. Comm. 77, 581-585, (1977)] have been reported. When the anhydrides are coupled to proteins the coupling proceeds via formation of an amide bond thus leaving four of the original five carboxymethyl groups on the diethylenetriamine (DETA) backbone [Hnatowich et al. Int. J. Appl. Isot. 33, 327-332, (1982)]. In addition, U.S. Pat. Nos. 4,432,907 and 4,352,751 disclose bifunctional chelating agents useful for binding metal ions to "organic species such as organic target molecules or antibodies." As in the above, coupling is obtained via an amide group through the utilization of diaminotetraacetic acid dianhydrides. Examples of anhydrides include dianhydrides of EDTA, CDTA, propylenediaminetetraacetic acid and phenylene 1,2-diaminetetraacetic acid. A recent U.S. Pat. No. 4,647,447 discloses several complex salts formed from the anion of a complexing acid for use in various diagnostic techniques. Conjugation via a carboxyl group of the complexing acid is taught which gives a linkage through an amide bond.

In the J. of Radioanalytical Chemistry 57(12), 553-564 (1980), Paik et al. disclose the use of p-nitrobenzylbromide in a reaction with a "blocked" diethylenetriamine, i.e. bis-(2-phthalimidoethyl)amine followed by deblocking procedures and carboxymethylation using chloroacetic acid, to give N'-p-nitrobenzyldiethylenetriamine N,N,N",N"-tetraacetic acid. Again, since the attachment is through a nitrogen, a tetraacetic acid derivative is obtained. Conjugation of the bifunctional chelating agent and chelation with indium is discussed. Substitution on the nitrogen atom is also taught by Eckelman, et al. in the J. of Pharm. Sci. 64(4), 704-706 (1975) by reacting amines such as "ethylenediamine or diethylenetriamine with the appropriate alkyl bromide before carboxymethylation." The compounds are proposed as potential radiopharmaceutical imaging agents.

Another class of bifunctional chelating agents based on aminocarboxylic acid functionality is also well documented in the literature. Thus, Sundberg, Meares, et al. in the J. of Med. Chem. 17(12), 1304 (1974), disclosed bifunctional analogs of EDTA. Representative of these compounds are 1-(p-aminophenyl)-ethylenediaminetetraacetic acid and 1-(p-benzene-diazonium)-ethylenediaminetetraacetic acid. Coupling to proteins through the para-substituent and the binding of radioactive metal ions to the chelating group is discussed. The compounds are also disclosed in Biochemical and Biophysical Research Communications 75(1), 149 (1977), and in U.S. Pat. Nos. 3,994,966 and 4,043,998. It is important to note that the attachment of the aromatic group to the EDTA structure is through a carbon of the ethylenediamine backbone. Optically active bifunctional chelating agents based on EDTA, HEDTA and DTPA are disclosed in U.S. Pat. No. 4,622,420. In these compounds an alkylene group links the aromatic group (which contains the functionality needed for attachment to the protein) to the carbon of the polyamine which contains the chelating functionality. Other references to such compounds include Brechbiel et al., Inorg. Chem. 25, 2772-2781 (1986), U.S. Pat. No. 4,647,447 and International Patent Publication No. WO 86/06384.

More recently, certain macrocyclic bifunctional chelating agents and the use of their copper chelate conjugates for diagnostic or therapeutic applications have been disclosed in U.S. Pat. No. 4,678,667 and by Moi et al., Inorg. Chem. 26, 3458-3463 (1987). Attachment of the aminocarboxylic acid functionality to the rest of the bifunctional chelating molecule is through a ring carbon of the cyclic polyamine backbone. Thus, a linker, attached at one end to a ring carbon of the cyclic polyamine, is also attached at its other end to a functional group capable of reacting with the protein.

Another class of bifunctional chelating agents, also worthy of note, consists of compounds wherein the chelating moiety, i.e. the aminocarboxylic acid, of the molecule is attached through a nitrogen to the functional group of the molecule containing the moiety capable of reacting with the protein. As an example, Mikola et al. in patent application (International Publication Number WO 84/03698, published Sep. 27, 1984) disclose a bifunctional chelating agent prepared by reacting p-nitrobenzylbromide with DETA followed by reaction with bromoacetic acid to make the aminocarboxylic acid. The nitro group is reduced to the corresponding amine group and is then converted to the isothiocyanate group by reaction with thiophosgene. These compounds are bifunctional chelating agents capable of chelating lanthanides which can be conjugated to bioorganic molecules for use as diagnostic agents. Since attachment of the linker portion of the molecule is through one of the nitrogens of the aminocarboxylic acid, then one potential aminocarboxyl group is lost for chelation. Thus, a DETA-based bifunctional chelant containing four (not five) acid groups is prepared. In this respect, this class of bifunctional chelant is similar to those where attachment to the protein is through an amide group with subsequent loss of a carboxyl chelating group.

Recently Carney, Rogers, and Johnson disclosed (3rd. International Conference on Monoclonal Antibodies For Cancer; San Diego, Calif.—Feb. 4–6, 1988) abstracts entitled "Absence of Intrinsically Higher Tissue Uptake from Indium-111 Labeled Antibodies: Co-administration of Indium-111 and Iodine-125 Labeled B72.3 in a Nude Mouse Model" and "Influence of Chelator Denticity on the Biodistribution of Indium-111 Labeled B72.3 Immunoconjugates in Nude Mice". The biodistribution of indium-111 complexed with an EDTA and DTPA bifunctional chelating agent is disclosed. Attachment of the aromatic ring to the EDTA/DTPA moieties is through an acetate methylene. Also at a recent meeting D. K. Johnson et al. [Florida Conf. on Chem. in Biotechnology, Apr. 26–29 (1988), Palm Coast, Fla.] disclosed bifunctional derivatives of EDTA and DTPA where a p-isothiocyanatobenzyl moiety is attached at the methylene carbon of one of the carboxymethyl groups. Previously Hunt et al. in U.S. Pat. Nos. 4,088,747 and 4,091,088 (1978) disclosed ethylenediaminediacetic acid (EDDA) based chelating agents wherein attachment of an aromatic ring to the EDDA moiety is through the alkylene or acetate methylene. The compounds are taught to be useful as chelates for studying hepatobiliary function. The preferred metal is technetium-99m. Indium-111 and indium-113m are also taught as useful radionuclides for imaging.

Consequently, it would be advantageous to provide a complex that does not readily dissociate, that exhibits rapid whole body clearance except from the desired tissue, and conjugates with an antibody to produce the desired results.

SUMMARY OF THE INVENTION

Figure 1:
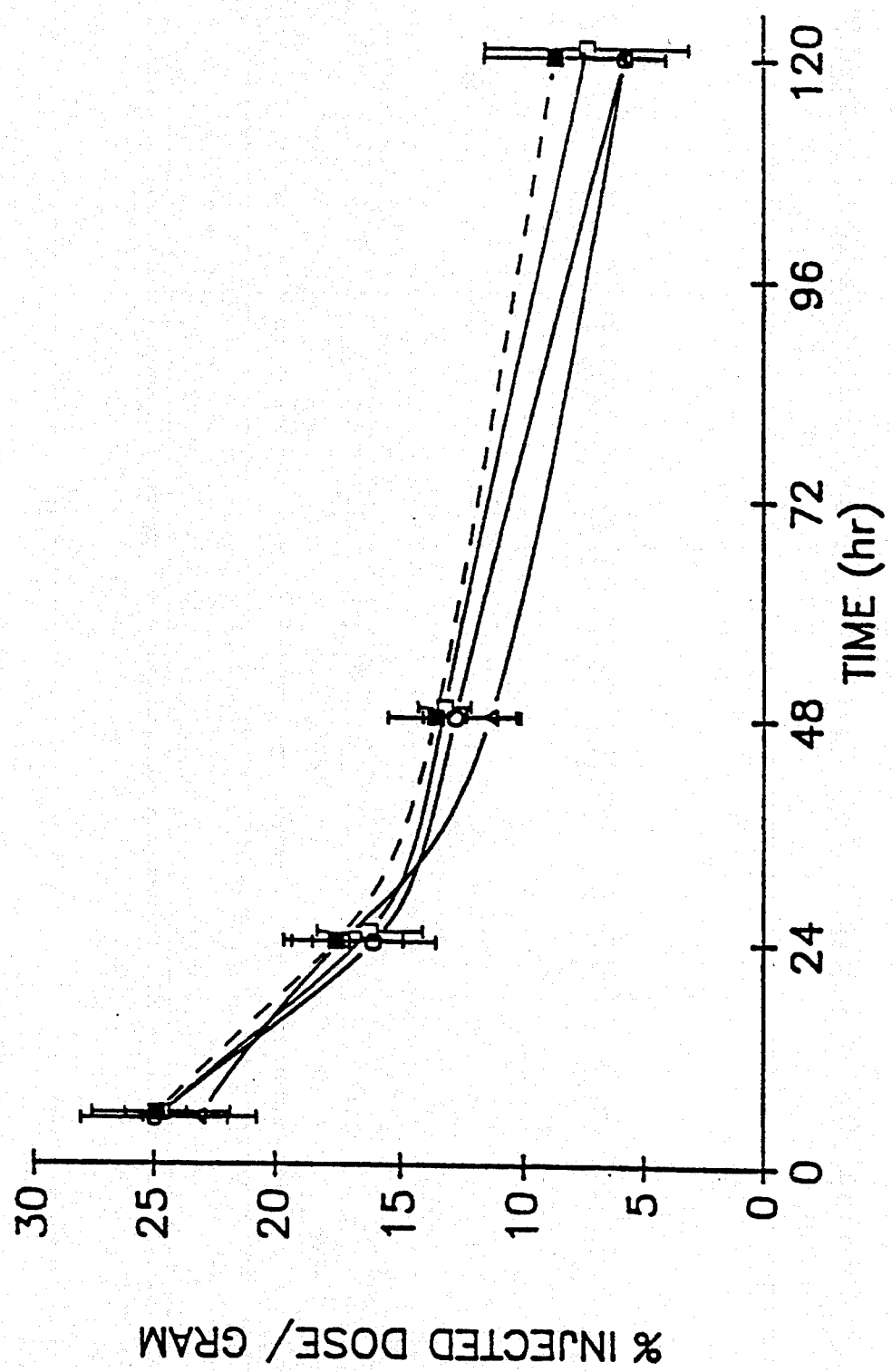
FIGS. 1–7 and 15–21 show the biodistribution of $^{153}$Sm as administered as a conjugate containing $^{153}$Sm of the present invention. The antibody, CC$_{49}$-IgG, was used in the conjugate of the present invention. The biodistribution was determined in nude mice bearing LS 174-T tumor.

Surprisingly, the complexes and/or conjugates of the invention are relatively stable (i.e. do not easily dissociate) and some display rapid clearance from the whole body and some non-target organs, such as liver, kidney and bone.

The invention includes the design and synthesis of novel bifunctional chelants, each containing a chelating functionality, and a chemically reactive group for covalent attachment to biomolecules. Also forming part of the invention are methods for preparing various bifunctional coordinator (BFC)-metal complexes and the linking of the complexes to antibody to prepare radionuclide (such as samarium-153, lutetium-177 and yttrium-90) labeled antibody and/or fragments suitable for diagnostic and/or therapeutic applications.

The present invention is directed to novel bifunctional chelating agents that form complexes with metal ions, especially "radioactive" metal ions having rare earth-type chemistry. Preferred rare earth-type metal ions include La, Ce, Pr, Nd, Pm, Sm, Eu, Gd, Tb, Dy, Ho, Er, Tm, Yb, Lu, Y and Sc, especially preferred are Sm, Ho, Y and Lu. Preferred radioactive rare earth-type metal ions include $^{153}$Sm, $^{166}$Ho, $^{90}$Y, $^{149}$Pm, $^{159}$Gd, $^{140}$La, $^{177}$Lu, $^{175}$Yb, $^{47}$Sc, and $^{142}$Pr, especially preferred are $^{153}$Sm, $^{166}$Ho, $^{90}$Y and $^{177}$Lu. Other radioactive metal ions which may be of interest are $^{47}$Sc, $^{99m}$Tc, $^{186}$Re, $^{188}$Re, $^{97}$Ru, $^{105}$Rh, $^{109}$Pd, $^{197}$Pt, $^{67}$Cu, $^{198}$Au, $^{199}$Au, $^{67}$Ga, $^{68}$Ga, $^{111}$In, $^{113m}$In, $^{115m}$In, $^{117m}$Sn, and $^{212}$Pb/$^{212}$Bi. The complexes so formed can be attached (covalently bonded) to an antibody or fragment thereof and used for therapeutic and/or diagnostic purposes. The complexes and/or conjugates can be formulated for in vivo or in vitro uses. A preferred use of the formulated conjugates is the treatment of cancer in animals, especially humans.

Uses of the complexes and/or conjugates of this invention which contain a non-radioactive metal for diagnosis and/or treatment of disease states such as cancer are also possible. Such uses are known for non-radioactive metals using radio frequency to induce hyperthermia (Jpn. Kokai Tokkyo Koho JP 61,158,931) and fluorescent-immunoguided therapy (FIGS) [K. Pettersson et al., *Clinical Chemistry* 29 (1), 60–64 (1983) and C. Meares et al., *Acc. Chem. Res.* 17, 202–1209 (1984].

More specifically, the present invention is directed to a compound of the formula:

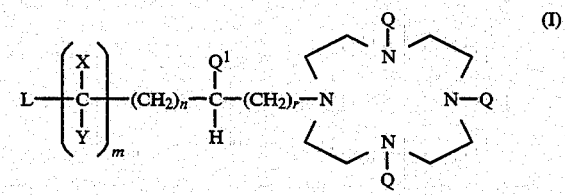

wherein:
each Q is independently hydrogen or (CHR$^{5'}$)$_p$CO$_2$R;
Q$^1$ is hydrogen or (CHR$^{5'}$)$_w$CO$_2$R;
each R independently is hydrogen, benzyl or C$_1$-C$_4$alkyl;
with the proviso that at least two of the sum of Q and Q$^1$ must be other than hydrogen;
each R$^{5'}$ independently is hydrogen, C$_1$-C$_4$ alkyl or —(C$_1$-C$_2$ alkyl)phenyl;
X and Y are each independently hydrogen or may be taken with an adjacent X and Y to form an additional carbon-carbon bond;
n is 0 or 1;
m is an integer from 0 to 10 inclusive;
p=1 or 2;
r=0 or 1;
w=0 or 1;
with the proviso that n is only 1 when X and/or Y form an additional carbon-carbon bond, and the sum of r and w is 0 or 1;
L is a linker/spacer group covalently bonded to, and replaces one hydrogen atom of one of the carbon atoms to which it is joined, said linker/spacer group being represented by the formula

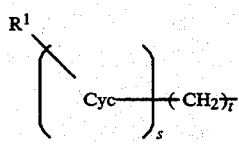

wherein:
s is an integer of 0 or 1;
t is an integer of 0 to 20 inclusive;
$R^1$ is an electrophilic or nucleophilic moiety which allows for covalent attachment to an antibody or fragment thereof, or a synthetic linker which can be attached to an antibody or fragment thereof, or precursor thereof3 and
Cyc represents a cyclic aliphatic moiety, aromatic moiety, aliphatic heterocyclic moiety, or aromatic heterocyclic moiety, each of said moieties optionally substituted with one or more groups which do not interfere with binding to an antibody or antibody fragment;
with the proviso that when s, t, m, r and n are 0, then $R^1$ is other than carboxyl; or
a pharmaceutically acceptable salt thereof.

Preferred features of the compounds of formula (I) are those where: R is hydrogen; $R^{5'}$ is H or methyl; n is 0; m is 0 through 5; r is 0 and L is a compound of the formula:

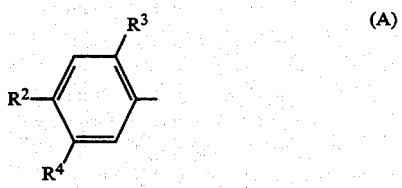

(A)

wherein:
$R^2$ is selected from the group consisting of hydrogen, nitro, amino, isothiocyanato, semicarbazido, thiosemicarbazido, carboxyl, bromoacetamido and maleimido;
$R^3$ is selected from the group consisting of $C_1$-$C_4$alkoxy, —$OCH_2CO_2H$, hydroxy and hydrogen;
$R^4$ is selected from the group consisting of hydrogen, nitro, amino, isothiocyanato, semicarbazido, thiosemicarbazido, carboxyl, bromoacetamido and maleimido;
with the proviso that $R^2$ and $R^4$ cannot both be hydrogen but one of $R^2$ and $R^4$ must be hydrogen; or
a pharmaceutically acceptable salt thereof.

When a conjugate of the present invention is desired $R^2$ and $R^4$ must be other than nitro. When $R^2$ or $R^4$ is nitro, then a precursor of the linker moiety (L) is present. This precursor moiety can be any moiety which is formed for $R^2$ or $R^4$ for the preparation of the compounds of formula (I) and which does not bind to an antibody or antibody fragment.

The present invention is also directed to rare-earth type metal ion complexes, especially radioactive neutral or charged rare-earth type metal ion complexes, and to conjugates formed with the aforementioned complexes and antibody or antibody fragments. In addition the present invention also includes formulations having the conjugates of the invention and a pharmaceutically acceptable carrier, especially formulations where the pharmaceutically acceptable carrier is a liquid. The invention also includes a method for the diagnosis or treatment of a disease state, especially cancer, in a mammal which comprises administering to the mammal an effective amount of the formulation.

DETAILED DESCRIPTION OF THE INVENTION

As used herein, the following indicated terms have these meanings: with respect to the definition of $R^1$, $R^2$ or $R^4$, electrophillc" moieties include, but are not limited to, isothiocyanate, bromoacetamide, maleimide, imidoester, thiophthalimide, N-hydroxysuccinimyl ester, pyridyl disulfide, and phenyl azide; suitable "nucleophilic" moieties include, but are not limited to, carboxyl, amino, acyl hydrazide, semicarbazide, and thiosemicarbazide; "synthetic linkers" include any synthetic organic or inorganic linkers which are capable of being covalently attached to an antibody or antibody preferred synthetic linkers are biodegradable synthetic linkers which are stable in the serum of a patient but which have a potential for cleavage within an organ of clearance for the radio-conjugate, for example biodegradable peptides or peptide containing groups. Of the electrophilic moieties isothiocyanate is preferred and of the nucleophilic moieties amino, semicarbazide and thiosemicarbazide are preferred. It is desirable that the nature and/or position of $R^1$ be such that it does not appreciably interfere with the chelation reaction.

The "X—C—Y" term in formula (I) represents the optional presence of a double or triple bond between adjacent carbon atoms. The unsaturated bonds may be present independently in the chain length of 0 to 10 carbon atoms inclusive as defined by the "m" term in formula (I).

As used herein, the term "mammal" means animals that nourish their young with milk secreted by mammary glands, preferably warm blooded mammals, more preferably humans. "Antibody" refers to any polyclonal, monoclonal, chimeric antibody or heteroantibody, preferably a monoclonal antibody; "antibody fragment" includes Fab fragments and F(ab')2 fragments, and any portion of an antibody having specificity toward a desired epitope or epitopes. When using the term "metal chelate/antibody conjugate" or "conjugate" the "antibody" portion is meant to include whole antibodies and/or antibody fragments, including semisynthetic or genetically engineered variants thereof.

As used herein, "complex" refers to a compound of the invention, e.g. formula (I), complexed with a rare-earth type metal ion, especially a radioactive rare-earth type metal ion, wherein at least one metal atom is chelated or sequestered; "radioactive metal ion chelate/antibody conjugate" or "radioactive metal ion conjugate" refers to a radioactive metal ion conjugate that is covalently attached to an antibody or antibody fragment; "radioactive" when used in conjunction with the word "metal ion" refers to one or more isotopes of the rare-earth type elements that emit particles and/or photons, such as $^{153}Sm$, $^{166}Ho$, $^{90}Y$, $^{149}Pm$, $^{159}Gd$, $^{140}La$, $^{177}Lu$, $^{175}Yb$, $^{47}Sc$, and $^{142}Pr$; the terms "bifunctional coordinator", "bifunctional chelating agent" and "functionalized chelant" are used interchangeably and refer to compounds that have a chelant moiety capable of chelating a metal ion and a linker/spacer moiety covalently bonded to the chelant moiety that is capable of serving as a means to covalently attach to an antibody or antibody fragment.

As used herein, "pharmaceutically acceptable salt" means any salt of a compound of formula (I) which is sufficiently non-toxic to be useful in therapy or diagnosis of mammals. Thus, the salts are useful in accordance with this invention. Representative of those salts, which are formed by standard reactions, from both organic and inorganic sources include, for example, sulfuric, hydrochloric, phosphoric, acetic, succinic, citric, lactic, maleic, fumaric, palmitic, cholic, palmoic, mucic, glutamic, d-camphoric, glutaric, glycolic, phthalic, tartaric, formic, lauric, steric, salicylic, methanesulfonic, benzenesulfonic, sorbic, picric, benzoic, cinnamic acids and other suitable acids. Also included are salts formed by standard reactions from both organic and inorganic sources such as ammonium, alkali metal ions, alkaline earth metal ions, and other similar ions. Particularly preferred are the salts of the compounds of formula (I) where the salt is potassium, sodium, ammonium, or mixtures thereof.

Of course, the free acid of the compounds of formula (I) may be used, also the protonated form of the compounds, for example when the carboxylate is protonated and/or the nitrogen atoms i.e. when the HCl salt is formed.

Preferred compounds of formula (I) include those compounds where $Q^1$ is hydrogen and L is represented by formula A as shown by the following formula:

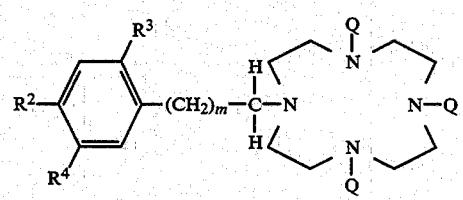

wherein:
  each Q is independently hydrogen or $CHR^5CO_2R$;
  each R independently is hydrogen, benzyl or $C_1$-$C_4$alkyl;
  with the proviso that at least two of Q must be other than hydrogen;
  m is an integer from 0 to 5 inclusive;
  $R^2$ is selected from the group consisting of hydrogen, nitro, amino, isothiocyanato, semicarbazido, thiosemicarbazido, carboxyl, bromoacetamido and maleimido;
  $R^3$ is selected from the group consisting of $C_1$-$C_4$alkoxy, $-OCH_2CO_2H$, hydroxy and hydrogen;
  $R^4$ is selected from the group consisting of hydrogen, nitro, amino, isothiocyanato, semicarbazido, thiosemicarbazido, carboxyl, bromoacetamido and maleimido;
  each $R^5$ independently is hydrogen or $C_1$-$C_4$ alkyl;
  with the proviso that $R^2$ and $R^4$ cannot both be hydrogen but one of $R^2$ and $R^4$ must be hydrogen; or
  a pharmaceutically acceptable salt thereof.

In formula (II) when $R^3$ and $R^4$ are both hydrogen, the compounds are represented by the following formula:

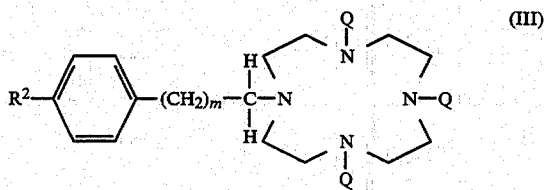

wherein:
  each Q is independently hydrogen or $CHR^5CO_2R$;
  each R independently is hydrogen, benzyl or $C_1$-$C_4$alkyl;
  with the proviso that at least two of Q must be other than hydrogen;
  m is an integer from 0 to 5 inclusive;
  $R^2$ is selected from the group consisting of nitro, amino, isothiocyanato, semicarbazido, thiosemicarbazido, carboxyl, bromoacetamido and maleimido;
  each $R^5$ independently is hydrogen or $C_1$-$C_4$ alkyl; or
  a pharmaceutically acceptable salt thereof.

In formula (II) when $R^2$ is hydrogen, the compounds are represented by the formula:

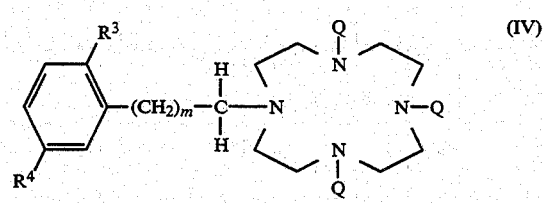

wherein:
  each Q is independently hydrogen or $CHR^5CO_2R$;
  each R independently is hydrogen, benzyl or $C_1$-$C_4$alkyl;
  with the proviso that at least two of Q must be other than hydrogen;
  m is an integer from 0 to 5 inclusive;
  $R^3$ is selected from the group consisting of $C_1$-$C_4$alkoxy, $-OCH_2CO_2H$ and hydroxy;
  $R^4$ is selected from the group consisting of nitro, amino, isothiocyanato, semicarbazido, thiosemicarbazido, carboxyl, bromoacetamido, and maleimido;
  each $R^5$ independently is hydrogen or $C_1$-$C_4$ alkyl; or
  a pharmaceutically acceptable salt thereof.

Additional preferred compounds of formula (I) include those compounds where at least one Q is hydrogen and are represented by the formula:

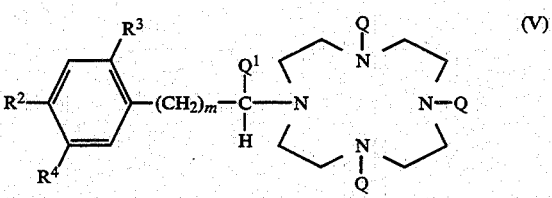

wherein:
  each Q is independently hydrogen or $CHR^5CO_2R$;
  $Q^1$ is hydrogen or $(CHR^5)_wCO_2R$;
  each R independently is hydrogen, benzyl or $C_1$-$C_4$alkyl;
  with the proviso that at least two of the sum of Q and $Q^1$ must be other than hydrogen and one of Q is hydrogen;
  m is an integer from 0 to 5 inclusive;

w is 0 or 1;

R² is selected from the group consisting of hydrogen, nitro, amino, isothiocyanato, semicarbazido, thiosemicarbazido, carboxyl, maleimido and bromoacetamido;

R³ is selected from the group consisting of $C_1$-$C_4$ alkoxy, —$OCH_2CO_2H$, hydroxy and hydrogen;

R⁴ is selected from the group consisting of hydrogen, nitro, amino, isothiocyanato, semicarbazido, thiosemicarbazido, carboxyl, maleimido and bromoacetamido;

each R⁵ independently is hydrogen or $C_1$-$C_4$ alkyl; with the proviso that R² and R⁴ cannot both be hydrogen but one of R² and R⁴ must be hydrogen;

a pharmaceutically acceptable salt thereof.

Other preferred compounds of formula (I) include compounds where $Q^1$ is $CO_2R$ (w=o) and are represented by the formula:

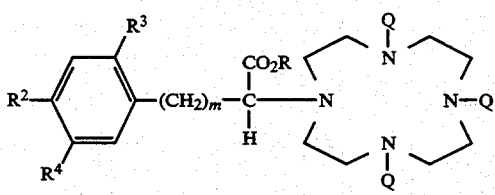
(VI)

wherein:
each Q is independently hydrogen or $CHR^5CO_2R$;
each R independently is hydrogen, benzyl or $C_1$-$C_4$ alkyl;
with the proviso that at least one Q must be other than hydrogen;
m is an integer from 0 to 5 inclusive;
R² is selected from the group consisting of hydrogen, nitro, amino, isothiocyanato, semicarbazido, thiosemicarbazido, carboxyl, maleimido and bromoacetamido;
R³ is selected from the group consisting of $C_1$-$C_4$ alkoxy, —$OCH_2CO_2H$, hydroxy and hydrogen;
R⁴ is selected from the group consisting of hydrogen, nitro, amino, isothiocyanato, semicarbazido, thiosemicarbazido, carboxyl, maleimido and bromoacetamido;
each R⁵ independently is hydrogen or $C_1$-$C_4$ alkyl; with the proviso that R² and R⁴ cannot both be hydrogen but one of R² and R⁴ must be hydrogen; or
a pharmaceutically acceptable salt thereof.

Some preferred compounds of formula (VI) are those where R³ and R⁴ are both hydrogen, the compounds are represented by the formula:

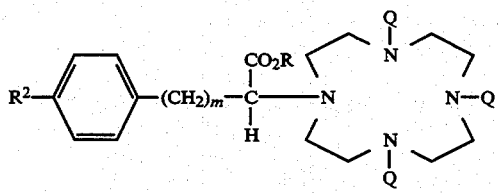
(VII)

wherein:
each Q is independently hydrogen or $CHR^5CO_2R$;
each R independently is hydrogen, benzyl or $C_1$-$C_4$ alkyl;
with the proviso that at least one Q must be other than hydrogen;
m is an integer from 0 to 5 inclusive;
R² is selected from the group consisting of nitro, amino, isothiocyanato, semicarbazido, thiosemicarbazido, carboxyl, bromoacetamido and maleimido;
each R⁵ independently is hydrogen or $C_1$-$C_4$ alkyl; or
a pharmaceutically acceptable salt thereof.

Other preferred compounds of formula (VI) are those where R² is hydrogen and are represented by the formula:

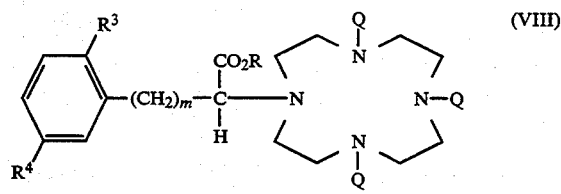
(VIII)

wherein:
each Q is independently hydrogen or $CHR^5CO_2R$;
each R independently is hydrogen, benzyl or $C_1$-$C_4$ alkyl;
with the proviso that at least one Q must be other than hydrogen;
m is an integer from 0 to 5 inclusive;
R³ is selected from the group consisting of $C_1$-$C_4$ alkoxy, —$OCH_2CO_2H$, and hydroxy;
R⁴ is selected from the group consisting of nitro, amino, isothiocyanato, semicarbazido, thiosemicarbazido, carboxyl, maleimido, and bromoacetamido;
each R⁵ independently is hydrogen or $C_1$-$C_4$ alkyl; or
a pharmaceutically acceptable salt thereof.

The bifunctional chelating agents described herein [represented by any one of formulas (I)–(VIII)] can be used to chelate or sequester the rare-earth type metal ions, particularly radioactive rare-earth type metal ions, so as to form metal ion chelates (also referred to herein as "complexes"). The complexes, because of the presence of the functionalizing moiety [represented by "R¹" in formula (I)], can be attached to functionalized supports, such as functionalized polymeric supports, or preferably, when a complex of formula (I) where L represents formula (A) and R² and R⁴ must be other than nitro, can be covalently attached to proteins or more specifically to antibodies or antibody fragments. Thus the complexes described herein (represented by any one of formulas I–VIII complexed with rare-earth type metal ions, particularly radioactive rare-earth type metal ions) may be covalently attached to an antibody or antibody fragment and are referred to herein as "conjugates".

The antibodies or antibody fragments which may be used in the conjugates described herein can be prepared by techniques well known in the art. Highly specific monoclonal antibodies can be produced by hybridization techniques well known in the art, see for example, Kohler and Milstein [*Nature* 256,495–497 (1975); and *Eur. J. Immunol.* 511–519 (1976)]. Such antibodies normally have a highly specific reactivity. In the radioactive metal ion conjugates, antibodies directed against any desired antigen or hapten may be used. Preferably the antibodies which are used in the radioactive metal ion conjugates are monoclonal antibodies, or fragments thereof having high specificity for a desired epitope(s). Antibodies used in the present invention may be directed against, for example, tumors, bacteria, fungi, viruses, parasites, mycoplasma, differentiation and other cell membrane antigens, pathogen surface antigens, toxins, enzymes, allergens, drugs and any biologically active molecules. Some examples of antibodies or antibody fragments are CC-11, CC-46, CC-49, CC-49 F(ab')$_2$, CC-83, CC-83 F(ab')$_2$, and B72.3. [See D. Colcher et al., *Cancer Res.* 48, 4597–4603 (Aug. 15, 1988) for CC-49, CC-83 and B72.3 antibodies. The CC MAbs, CC83, CC49, CC46, CC92, CC11, and CC30, were developed by the immunization of mice with purified TAG-72 as described previously [see R. Muraro et al., *Cancer Res.* 48, 4588–4596 (1988)]. Purified TAG-72 was used to immunize 4-week-old BALB/c mice over an extended period of time and the spleen cells were fused with NS-1 cells to generate hybridomas. Selected cells were chosen for further study and the hybridomas were cloned twice by limiting dilution. The monoclonal antibodies were extensively characterized and their reactivity to colon carcinomas with minimal reactivity to normal human and adult tissues has been described [see R. Muraro et al., *Cancer Res.* 48, 4588–4596 (1988)]. Ascitic fluid containing the various MAbs were generated by the i.p. inoculation of approximately $1 \times 10^6$ hybridoma cells into BALB/c mice that were previously primed with pristane. The ascitic fluid was harvested and clarified at $10,000 \times g$ for 10 minutes before storage at $-20°$ C. The hybridoma cell line B72.3 is deposited in the American Type Culture Collection (ATCC) having the accession number HB 8108. The various CC antibodies are disclosed in U.S. patent application 7-073,685, filed Jul. 15, 1987, now abandoned, and a continuation-in-part application was filed on Jul. 2, 1990 as U.S. Application Ser. No. 547,336, which is pending, and which are available through NTIS. The monoclonal antibodies specifically developed in the stated U.S. Applications, are designated CC 1 to CC 92 (IgG monoclonal antibodies) and all have binding specificity to TAG-72 (high molecular weight tumor associated glycoprotein) and numerous types of human carcinomas (including breast, ovarian, lung, colorectal, endometrial and pancreatic carcinomas) and are different from B72.3 in that they:

(1) have binding specificity to more human carcinomas than B72.3 while still maintaining essentially no specificity to normal adult human tissues;

(2) have a higher binding affinity for TAG-72 than B72.3 i.e., on the order of greater than $3 \times 10^9$M, preferably greater than $8 \times 10^9$M and consequently bind human carcinomas in vivo at a higher efficiency;

(3) exhibit a 50% or more efficiency than B72.3 in targeting human carcinomas in-stitu (i.e., 50% more injected dose/gram tumor than B72.3 and preferably greater than 100% more injected dose/gram tumor than B72.3);

(4) can be easily fragmented with pepsin to obtain F(ab')$_2$, F(ab') and Fab fragments that are highly immunoreactive; and (5) include monoclonal antibodies of the IgG2a, IgG2b, and IgM isotypes so they can more efficiently be used in monoclonal antibody targeted effector cell mediated cytotoxicity or complement mediated cytotoxicity studies. The other murine monoclonal antibodies bind to epitopes of TAG-72, a tumor associated antigen.] A more complete list of antigens can be found in U.S. Pat. No. 4,193,983, which is incorporated herein by reference. The radioactive metal ion conjugates of the present invention are particularly preferred for the diagnosis and treatment of various cancers.

The preferred rare-earth type (lanthanide or pseudolanthanide) complexes of the present invention are represented by the formula:

$$C[Ln(BFC)] \qquad \text{(IX)}$$

wherein: Ln is a rare-earth metal (lanthanide) ion, such as $Ce^{3+}$, $Pr^{3+}$, $Nd^{3+}$, $Pm^{3+}$, $Sm^{3+}$, $Eu^{3+}$, $Gd^{3+}$, $Tb^{3+}$, $DY^{3+}$, $Ho^{3+}$, $Er^{3+}$, $Tm^{3+}$, $Yb^{3+}$, and $Lu^{3+}$, or pseudo-lanthanide metal ion, such as $Sc^{3+}$, $Y^{3+}$ and $La^{3+}$ such as, especially preferred metal ions are $Y^{3+}$, $Ho^{3+}$, $Lu^{3+}$ or $Sm^{3+}$; BFC represents a bifunctional chelant; and C represents a pharmaceutically acceptable ion or group of ions of sufficient charge to render the entire complex neutral. If the BFC contains four or more negatively charged moieties, then C is a cation or group of cations such as $H^+$, $Li^+$, $Na^+$m $K^+$, $Rb^+$, $Cs^+$, $Mg^{2+}$, $Ca^{2+}$, $Sr^{2+}$, $Ba^{2+}$, $NH_4^+$, $N(CH_3)_4^+$, $N(C_2H_5)_3^+$, $N(C_3H_7)_4^+$, $N(C_4H_9)_4^+$, $As(C_6H_5)_4^+$, $[N(C_6H_5)_3P=]_2N^+$ and other protonated amines. If the BFC contains three negatively charged moieties, then C is not required. If the BFC contains two negatively charged moieties, then C is an anion such as $F^-$, $Cl^-$, $Br^-$, $I^-$, $ClO_4^-$, $BF_4^-$, $H_2PO_4^-$, $HCO_3^-$, $HCO_2^-$, $CH_3SO_3^-$, $H_3C-C_6H_4-SO_3^-$, $PF_6^-$, $CH_3CO_2^-$ and $B(C_6H_5)_4^-$.

The conjugates of this invention, and in some instances the complexes of this invention, may be employed as a formulation. The formulation comprises a compound of formula (I) with the antibody and/or metal ion and a physiologically acceptable carrier, excipient or vehicle therefore. Thus, the formulation may consist of a physiologically acceptable carrier with a complex (metal ion + ligand), conjugate (metal ion + ligand + antibody) or (ligand + antibody). The methods for preparing such formulations are well known. The formulation may be in the form of a suspension, injectable solution or other suitable formulation. Physiologically acceptable suspending media, with or without adjuvants, may be used.

The formulations of the present invention are in the solid or liquid form containing the active radionuclide complexed with the ligand. These formulations may be in kit form such that the two components (i.e. ligand and metal, complex and antibody, or ligand/antibody and metal) are mixed at the appropriate time prior to use. Whether premixed or as a kit, the formulations usually require a pharmaceutically acceptable carrier.

Injectable compositions of the present invention may be either in suspension or solution form. In the preparation of suitable formulations it will be recognized that, in general, the water solubility of the salt is greater than the acid form. In solution form the complex (or when desired the separate components) is dissolved in a physiologically acceptable carrier. Such carriers comprise a suitable solvent, preservatives such as benzyl alcohol, if needed, and buffers. Useful solvents include, for example, water, aqueous alcohols, glycols, and phosphonate or carbonate esters. Such aqueous solutions contain no more than 50 percent of the organic solvent by volume.

Injectable suspensions are compositions of the present invention that require a liquid suspending medium, with or without adjuvants, as a carrier. The suspending medium can be, for example, aqueous polyvinylpyrrolidone, inert oils such as vegetable oils or highly refined mineral oils, or aqueous carboxymethylcellulose. Suitable physiologically acceptable adjuvants, if necessary to keep the complex in suspension, may be chosen from among thickeners such as carboxymethylcellulose, polyvinylpyrrolidone, gelatin, and the alginates. Many surfactants are also useful as suspending agents, for example, lecithin, alkylphenol, polyethylene oxide adducts, napthalenesulfonates, alkylbenzenesulfonates, and the polyoxyethylene sorbitan esters.

Many substances which effect the hydrophilicity, density, and surface tension of the liquid suspension medium can assist in making injectable suspensions in individual cases. For example, silicone antifoames, sorbitol, and sugars are all useful suspending agents.

An "effective amount" of the formulation is used for therapy. The dose will vary depending on the disease being treated. Although in vitro diagnostics can be performed with the formulations of this invention, in vivo diagnostics are also contemplated using formulations of this invention. The conjugates and formulations of this invention can also be used in radioimmuno guided surgery (RIGS); however, other metals which could be used for this purpose also include $^{99m}$Tc, $^{111}$In, $^{113m}$In, $^{67}$Ga and $^{68}$Ga.

Other uses of some of the chelants of the present invention may include magnetic resonance imaging, e.g. the complexes of formula I, especially complexes of formula VI, with $Gd^{+3}$ attachment to polymeric supports for various purposes, e.g. as diagnostic agents, and removal of lanthanide metal or pseudo-lanthanide metal ion by selective extraction.

The present invention provides chelants, complexes, and antibody conjugates some of which are more stable, and/or have improved biodistribution, and/or have more rapid clearance from the body, than those known in the art.

DETAILED DESCRIPTION OF THE PROCESS

A reasonable and general synthetic approach to a twelve-membered macrocyclic, bifunctional chelant of the present invention as represented by formula (I) involves monofunctionalization of a free-base macrocycle (e.g. 1,4,7,10-tetraazacyclododecane) at only one of the nitrogen atoms with an appropriate electrophile (e.g. any appropriately substituted α-halocarboxylic acid ester). This electrophile must possess a suitable linker moiety or suitably protected linker moiety which would allow covalent attachment of the bifunctional ligand to a protein, antibody or antibody fragment.

It is recognized in the art that alkylative techniques for the production of mono-N-functional polyazamacrocycles may result in mixtures of difficult to separate products [T. Kaden, *Top. Curr. Chem.* 121, 157-75 (1984)]. This problem has been overcome through the reported use of large excesses of macrocycle (5-10 equivalents relative to electrophile) which favors formation of the monoalkylation adduct [M. Studer and T. A. Kaden, *Helv. Chim. Acta* 69, 2081-86 (1986); E. Kimura et al., *J. Chem. Soc. Chem. Commun.* 1158-59 (1986)].

Other routes to mono-N-functional polyazamacrocycles involve lengthy protection, functionalization, and deprotection schemes [P. S. Pallavicini et al., *J. Amer. Chem. Soc.* 109, 5139-44 (1987); M. F. Tweedle et al., *Eur. Pub. Pat. Appln. No.* 0232-751]. A recent report of a reductive amination of substituted phenyl pyruvic acids and amines has issued by Abbott Labs. as an Abstract from a recent meeting (D. K. Johnson et al., Florida Conf. on Chem. in Biotechnology, April 26-29 (1988), Palm Coast, Fla.). A process that prepares mono-N-alkylated polyazamacrocycles by using an electrophile with between about one and five equivalents of a suitable macrocycle in a solvent which will not promote a proton transfer is disclosed in U.S. application Ser. No. 289,163, by W. J. Kruper, filed Dec. 22, 1988, now abandoned, and a continuation-in-part application was filed on Jul. 9, 1990 as U.S. Application Ser. No. 549,791, which has issued as U.S. Pat. No. 5,064,956, the disclosure of which is hereby incorporated by reference.

General synthetic routes to the chelants of the present invention are disclosed in Synthesis Schemes I-IV hereinafter and involve the reaction of a suitable electrophile and the polyazamacrocycle, at various stoichiometries, temperatures and concentrations, in an appropriate organic solvent. Examples of suitable organic solvents are any hydrocarbon which supports solubility, such as acetonitrile, isopropanol, methylene chloride, toluene, chloroform, n-butanol, carbon tetrachloride, tetrahydrofuran, 5% ethanol in chloroform, with the most preferred being chloroform, methylene chloride, n-butanol, 1,4-dioxane and acetonitrile. Stoichiometric amounts or nearly stoichiometric amounts of macrocycle and electrophile may be employed and yield the corresponding mono-N-alkylation product in a single step. The temperature range for the reaction is from about 0° C. to about reflux, preferably from 0° C. to 2.5° C. The time of the reaction until completion is about 1 to about 24 hours.

General access to substituted α-haloacid esters is desirable for the overall viability of Synthesis Schemes II and IV. One suitable approach involves bromination or chlorination of the acid halide generated in situ, e.g. D. N. Harpp et al., *J. Org. Chem.* 40, 3420-27 (1975). This approach allows for exclusive alpha halogenation of alkanoic acids which contain even reactive benzylic groups. A general method to substituted acid halides involves reaction of the organic acid with thionyl chloride or sulfuryl chloride, e.g. E. Schwenk et al. *J. Amer. Chem. Soc.* 70, 3626-27 (1944). Both methods utilize the free carboxylic acid which is frequently available from commercial sources.

Polyazamacrocycles such as 1,4,7,10-tetraazacyclododecane may be prepared by documented methods such as T. J. Atkins et al., *J. Amer. Chem. Soc.* 96, 2268-70 (1974) and T. J. Richman et al., *Org. Synthesis* 58, 86-98 (1978).

Carboxymethylation of the mono-N-functional macrocycle may be performed by the method of Desreux using bromoacetic acid derivatives and a suitable base [J. F. Desreux, *Inorg. Chem.* 19, 1319-24 (1980)].

All of the starting materials required for preparing the compounds of this invention are either available from commercial sources or can be made from known literature reference descriptions.

In the following Scheme I, the compounds of formula (I) are prepared where $Q^1$ is hydrogen. Although only one compound is indicated by the terms shown, other similar moieties within formula (I) where $Q^1$ is hydrogen, r=0 or 1, n=0 or 1, and m=0 through 10 can also be prepared by this method.

Scheme I

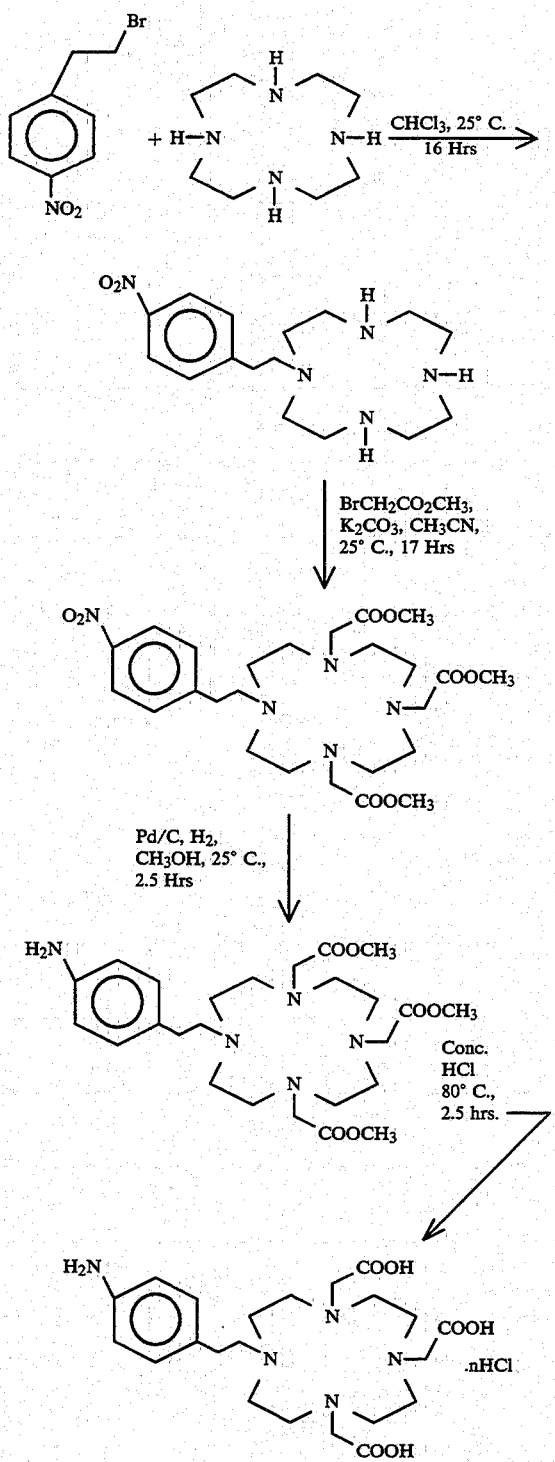

Scheme II

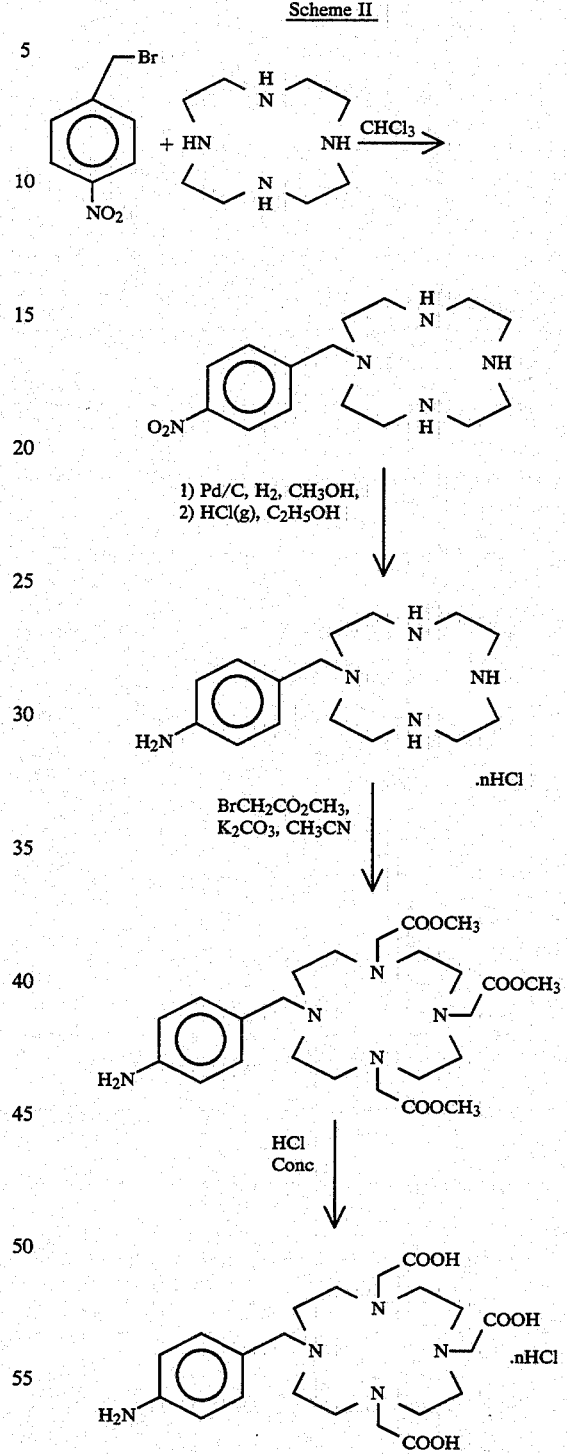

In the following Scheme II, the compounds of formula (I) are prepared where $Q^1$ is hydrogen. Although only one compound is indicated by the terms shown, other similar moieties within formula (I) where $Q^1$ is hydrogen, r=0 or 1, n=0 or 1 and m=0 through 10 can also be prepared by this method.

In the following Scheme III, the compounds of formula (I) are prepared where $Q^1$ is $CO_2R$. Although only one compound is indicated by the terms shown, other similar moieties within formula (I) where $Q^1$ is $CO_2R$, including m=0 through 10, n=0 or 1 and r=0 or 1 can also be prepared by this method.

Scheme III

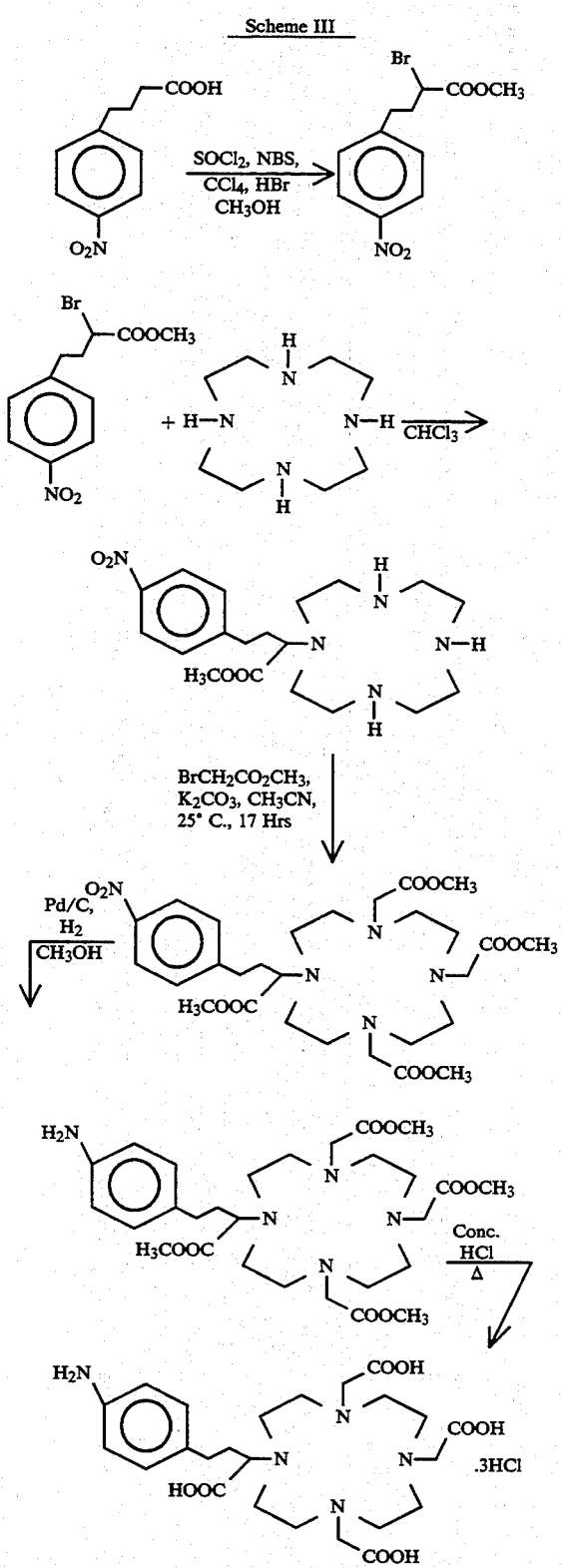

Scheme IV

In Scheme IV, the reagent shown containing A' can be any suitable leaving group for a α-acid, i.e. A' is phenyl or $CF_3$.

Use of an optically active alkylating agent has minimized the diastereomers and simplifies the synthesis. Isolation of a single diastereomer which would give rise to a single, easily purified lanthanide complex would be desirable for radiochelation as well as antibody conjugation.

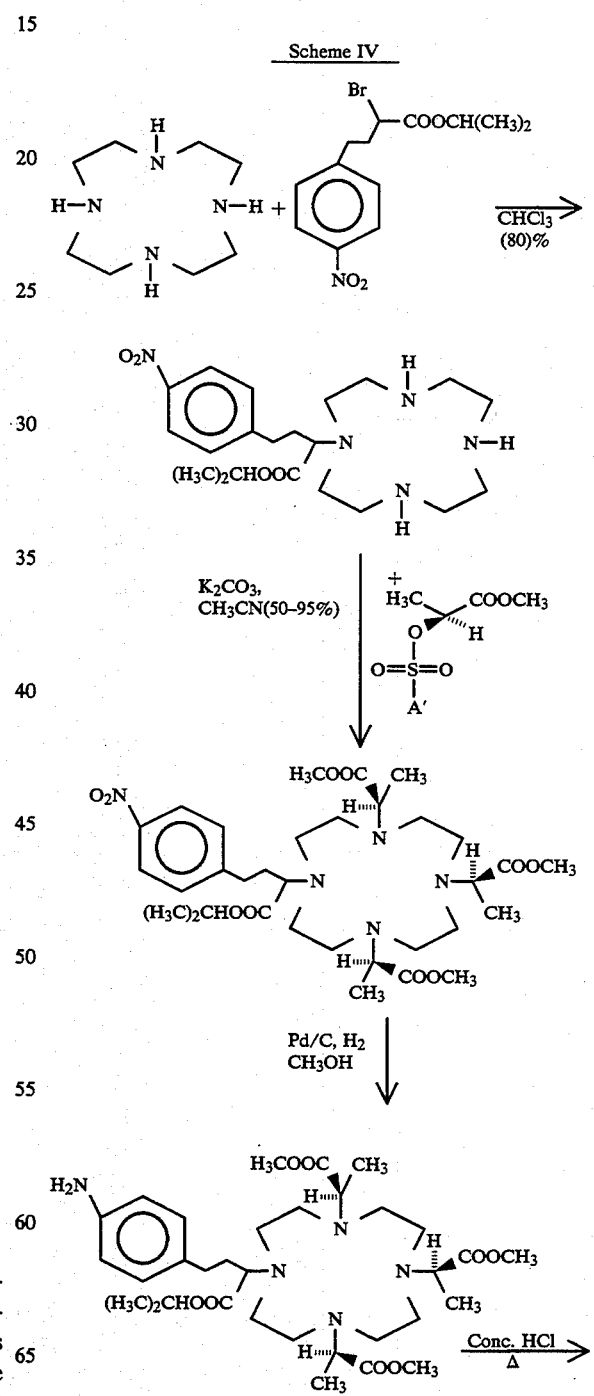

In the following Scheme IV, the compounds of formula (I) are prepared where $Q^1$ is $(CHR^{5'})_wCO_2R$. Although only one compound is indicated by the terms shown, other similar moieties within formula (I) where $Q^1$ is $(CHR^{5'})_wCO_2R$, including m=0 through 10, n=0 or 1 and r=0 can also be prepared by this method.

-continued
Scheme IV

Scheme V

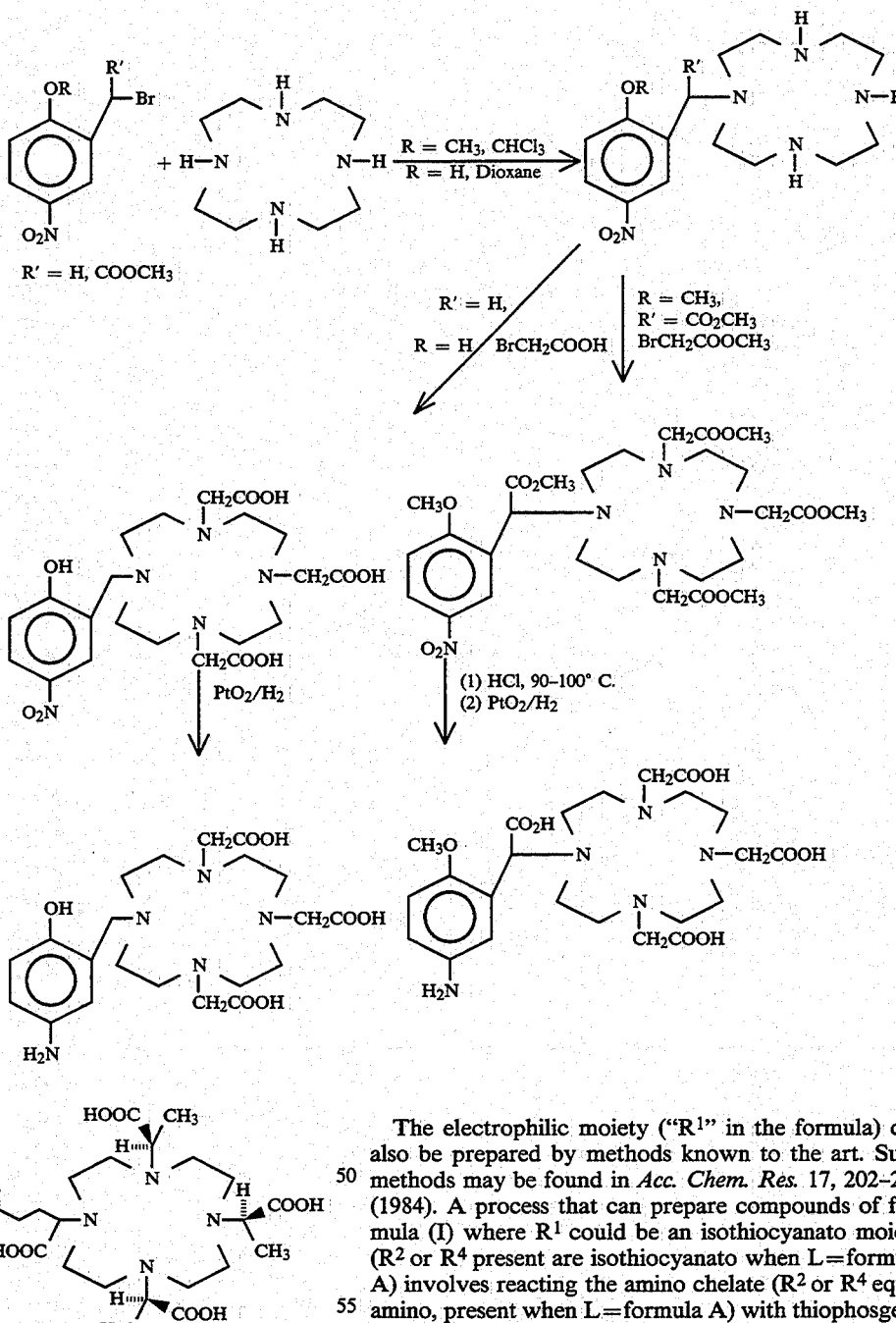

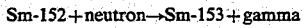

In the following Scheme V, the compounds of formula (I) are prepared where $Q^1$ is hydrogen or $(CHR^5)_wCO_2R$ and $R^2$ is hydrogen. Although only two compounds are indicated by the terms shown, other similar moieties within formula (I) where $Q^1$ is hydrogen or $(CHR^5)_wCO_2R$, Q is hydrogen or $(CHR^5)_pCO_2R$, r=0 or 1, n=0 or 1, w=0 or 1, m=0 through 10, p=1 or 2, L represents formula A wherein $R^3$ is defined as before, $R^2$ and $R^4$ are selected from the group consisting of hydrogen, amino, nitro, isothiocyanato, semicarbazido, thiosemicarbazido, maleimido, bromoacetamido and carboxyl, can also be prepared by this method.

The electrophilic moiety ("$R^1$" in the formula) can also be prepared by methods known to the art. Such methods may be found in Acc. Chem. Res. 17, 202–209 (1984). A process that can prepare compounds of formula (I) where $R^1$ could be an isothiocyanato moiety ($R^2$ or $R^4$ present are isothiocyanato when L=formula A) involves reacting the amino chelate ($R^2$ or $R^4$ equal amino, present when L=formula A) with thiophosgene and is disclosed in U.S. application Ser. No. 289,172, by M. J. Fazio, et al., filed Dec. 23, 1988, the disclosure of which is hereby incorporated by reference.

Radionuclides can be produced in several ways. In a nuclear reactor a nuclide is bombarded with neutrons to obtain a radionuclide, e.g.

Sm-152+neutron→Sm-153+gamma

Another method of obtaining radionuclides is to bombard nuclides with particles in a linear accelerator or a cyclotron. Yet another way is to isolate the radionuclide from a mixture of fission products. The method of obtaining the nuclides employed in the present invention is not critical thereto.

The conjugates of the present invention can be prepared by first forming the complex and then binding the antibody or antibody fragment. Thus the process involves preparing or obtaining the ligand, forming the complex with the metal and then adding the antibody. Alternatively, a process for making labeled antibody conjugates can involve first conjugation of the BFC to the antibody and its subsequent chelation to yield the radionuclide-BFC labeled Ab. Any suitable process that results in the formation of the conjugates of this invention is within the scope of this invention.

In the following examples, the following terms and conditions were used unless otherwise specified.

GENERAL EXPERIMENTAL

Mass spectra were obtained on either a Finnigan TSQ mass spectrometer ($Q^1MS$ mode) or a VG ZAB-MS high resolution mass spectrometer (fast atom bombardment with xenon, using 3:1 dithiothreitol:dithioerythritol).

$^1H$ and $^{13}C$ NMR spectra were obtained using a Varian VXR-300, Bruker APC 300, IBM/Bruker NR-80 or a Jeol FX400 spectrometer. All spectra were obtained at 30° C. unless otherwise noted. $^1H$ NMR was done at 300 MHz, 80 MHz or 400 MHz, respectively to the equipment listed above; $^{13}C$ NMR was done at 75 MHz, 20 MHz or 100 MHz, respectively to the equipment listed above. The values for the NMR are δ versus TMS (tetramethylsilane) or when $D_2O$ was the solvent versus DSS (2,2-dimethyl-2-silapentane-5-sulfonic acid, sodium salt).

Infrared spectra (IR) were recorded on a Nicolet 5SX FT/IR instrument.

For the chromatography procedures, most solvents were Fisher HPLC grade materials. Ammonium acetate was purchased from Aldrich. Water was purified using a Barnstead NANOpure TM water filtration system. Preparative chromatography of organic compounds was performed either by normal gravity chromatography using standard techniques or by flash chromatography as described by C. W. Still et al., *J. Org. Chem.* 43, 2923–24 (1978). The following solvent systems were used:

| Solvent System | Components |
|---|---|
| 1 | $CHCl_3:CH_3OH$:conc. $NH_4OH$ 2:2:1 V:V:V |
| 2 | $CHCl_3:CH_3OH$:conc. $NH_4OH$ 12:4:1 V:V:V |
| 3 | $CHCl_3:CH_3OH$:conc. $NH_4OH$ 16:4:1 V:V:V |
| 4 | $CHCl_3:CH_3OH$:conc. $NH_4OH$ 4:2:1 V:V:V |
| 5 | $CHCl_3:CH_3OH$:conc. $NH_4OH$ 3:2:1 V:V:V |
| 6 | $CHCl_3:CH_3OH$:conc. $NH_4OH$ 7:3:1 V:V:V |
| 7 | saline (0.85% of NaCl in distilled water):conc. $NH_4OH$ 4:1 V:V |
| 8 | $CHCl_3:CH_3OH$:conc. $NH_4OH$ 4:4:1 V:V:V |

$R_f$ values are reported using these solvent systems and commercially available, normal phase, silica TLC plates [GHLF 250 micron, Analtech Inc. or Merck Kiesel gel $60F_{254}$]. Preparative column chromatography was done using Merck grade 60, 60 Å silica gel. All percentages are by weight unless stated otherwise.

Some solids were dried using a rotary evaporator (Buchi 461) and/or a vacuum oven at a temperature of about 55°–60° C. for several hours. In addition, a Virtis model 10-010 automatic freezer dryer or Speed Vac TM concentrator was used for solvent removal.

Samarium-153 and lutetium-177 were produced by the Research Reactor, University of Missouri (Columbia, Mo.). Yttrium-90 was purchased from Oak Ridge National Laboratory.

1-(4-Isothiocyanatobenzyl)diethylenetriaminepentaacetic acid (SCN-Bz-DTPA) was prepared by a modification to the procedure of M. W. Brechbiel, et al., *Inorg. Chem.* 25, 2772–2781 (1986), and purified to give a single species on anion exchange HPLC (Q-Sepharose TM ). Some of the chemicals used were obtained from the sources indicated: N-2-hydroxyethylpiperazine-N'-2-ethanesulfonic acid (HEPES), free acid and sodium salt were purchased from Behring Diagnostics (La Jolla, Calif.); sodium citrate (certified) was from Fisher Scientific; thiophosgene was from Aldrich Chemicals; ammonium acetate, sodium acetate, ethylenediaminetetraacetic acid (EDTA) and phosphate buffered saline (PBS) were from Sigma Diagnostics.

HPLC columns used were: Hand-packed Q-Sepharose TM (Pharmacia) either 1.5 cm×25 cm or 2.5 cm×25 cm; Zorbax TM BIO Series GF-250 (9.4 mm×25 cm) from Du Pont Instruments; Vydac TM (Trademark of the Separations Group, Hesperia, Calif.) protein C-4 (4.6 mm×25 cm) from the Separation Group (Hesperia, Calif.); and Mono-Q TM and SP-Sephadex TM (Tradename of Pharmacia Biotechnology Products) from Pharmacia. Sep-Pak TM (Tradename of Waters Associates) C-18 cartridge was purchased from Waters Associates (Milford, Mass.), Sephadex TM G-25 disposable columns (2.2 ml) from Isolab Inc. (Akron, Ohio), and Centricon TM -30 (Tradename of Amicon Division, W. R. Grace & Co., Danvers, Mass.) microconcentrators from Amicon.

Five HPLC systems were used for analyses and sample separations:

System I consisted of LKB 2150 pump, and 2152 controller, a UV detector—LKB 2238 UV Cord, a Berthold LB 506 A HPLC Radioactivity Monitor (of the International Berthold Group) and a Gilson Fraction collector 201-202 (Gilson International, Middleton, Wisc.);

System II was equipped with an auto-sampler, WISP 710 B, two pumps (model 510) and an automated gradient controller (of Waters Associates), a Perkin-Elmer LC-75 spectrophotometric detector, a Beckman model 170 Radioisotope Detector, and a fraction collector (Frac-100 of Pharmacia);

System III consisted of two Waters M-6000A pumps with a Waters 660 solvent Programmer, a Waters Model 481 Variable Wavelength Detector, and a Waters Data Module, also an ISCO fraction collector was used preparatively;

System IV was Dionex BioLC ™ System equipped with a variable wavelength UV detector; and System V was a Waters Model 590 Pump with an ISCO Model 2360 gradient programmer and a Dionex variable wavelength detector.

For centrifugation and concentration, a Sorvall RT 6000B (refrigerated centrifuge of Du Pont) was used. A Speed Vac concentrator (Savant Instruments Inc., Hicksville, N.Y.) was employed for removal of volatile solvents. Radioactivity measurements were done on a Capintec ™ Radioisotope Calibrator (Trademark of Capintec Inc.) CRC-12, or by liquid scintillation on Beckman LS 9800 (Beckman Instruments, Inc., Irvine, Calif.), or on a Canberra 35+ multichannel analyzer interfaced with a 3 in. thallium drifted sodium iodide well crystal.

In the examples concerning formation of complex, the percent complex determination was performed by the following general method where indicated.

Percent Complex Determination by Cation Exchange

A 10 ml plastic column was filled with 1 to 2 ml of SP-Sephadex ™ C-25 resin which was swelled in water. The excess water was removed by applying pressure to the top of the column. The test solution (15 μl) was added to the top of the resin, then 2 ml of 4:1 (V:V) of isotonic saline: conc. NH₄OH was used as an eluent. The eluent was collected in a counting tube. An additional 2 ml of eluent was used. After collection of eluent into a second counting tube, air pressure was applied to the top of the resin to bring it to dryness. The dried resin was transferred to a third counting tube. The activity of each counting tube was measured with a NaI well counter coupled to a Canberra multichannel analyzer. The amount of the metal as a complex was given as the percentage of the total activity that was found in the eluent. The amount of metal in the free uncomplexed state was given as the percentage of the total metal that remains in the resin.

Removal of Uncomplexed Metal by Ion Exchange

A 10 ml plastic column was filled with 0.5 ml of SP-Sephadex ™ C-25 resin swelled in water. The excess water was removed by centrifuging the column at 3,000 rpm for 4 min. A volume of 200-500 μl of the complex solution was placed at the top of the resin and the tube centrifuged again for 4 minutes at 3,000 rpm. The uncomplexed metal remained in the column and the complexed metal eluted with the solvent.

Yttrium Complex Preparation

Complexes were made by preparing a $3 \times 10^{-4}$M yttrium solution in water (YCl$_3$.6H$_2$O, 303.26 g/mole; or Y(OAc)$_3$, 12.1% H$_2$O). Radioactive Y$^{3+}$ solution (Oakridge National Laboratories) was added to give the desired level of radioactivity. Ten μl of ligand solution (at 0.03M) was added to 990 μl of the Y$^{3+}$ solution, giving a 1:1 molar ratio of ligand:metal. Ten times the amount of ligand solution was used for a 10:1 ligand to ratio. The pH was adjusted to 7.4 using microliter quantities of HCl or NaOH. The solution was then tested for the amount of complexed yttrium using the cation exchange method given above.

Samarium Complex Preparation

Samarium complexes were formed as described above for yttrium complexes except that $3 \times 10^{-4}$M samarium was prepared by dissolution of Sm$_2$O$_3$ (348.7 g/mole) in 0.1M HCl. Radioactive Sm-153 was obtained as a about $3 \times 10^{-4}$M solution in 0.1M HCl from the University of Missouri Research Reactor, Columbia, Mo.

The following definitions are provided for some terms that are used throughout this text.

GLOSSARY

Conc. means concentrated;
−OAc means the acetate moiety, −OCOCH$_3$;
TLC means thin layer chromotography;
DI H$_2$O means deionized NANOpure ™ water;
NANOpure ™ water is pure water obtained from a Barnstead NANOpure ™ water filtration system;
Ambient temperature means room temperature or about 20° to about 25° C.;
Overnight means from about 9 to 18 hours;
LC means liquid chromatography;
NBS means N-bromosuccinimide;
MES means 2-(N-morpholino)ethanesulfonic acid;
HPLC means high performance liquid chromatography;
PBS means phosphate buffered saline from Sigma, containing 120 mM NaCl, 2.7 mM KCl and 10 mM phosphate buffer, pH 7.4;
SP-Sephadex ™ C-25 resin is a cation exchange resin having sulfonic acid functionality, sold by Pharmacia, Inc.;
rpm = revolutions per minute;
pD means pH where the hydrogen is deuterated;
DOTA = 1,4,7,10-tetraazacyclododecane-1,4,7,10-tetraacetic acid;
HEPES = N-2-hydroxyethylpiperazine-N'-2ethanesulfonic acid;
BFC = bifunctional chelant;
Cyclen = 1,4,7,10-tetraazacylododecane;
PA-DOTA = α-[2-(4-aminophenyl)ethyl]-1,4,7,10-tetraazacyclododecane-1,4,7,10-tetraacetic acid;
PA-DOTMA = α-[2-(4-aminophenyl)ethyl]-1,4,7,10-tetraazacyclododecane-1-acetic-4,7,10-tris(methylacetic) acid;
BA-DOTA = α-(4-aminophenyl)-1,4,7,10-tetraazacyclododecane-1,4,7,10-tetraacetic acid;
OMe-BA-DOTA = α-(5-amino-2-methoxyphenyl)-1,4,7,10-tetraazacyclododecane-1,4,7,10-tetraacetic acid;
EA-DO3A = 1-[2-(4-aminophenyl)ethyl]-1,4,7,10-tetraazacyclododecane-4,7,10-triacetic acid;
DTPA = diethylenetriaminepentaacetic acid;
SCN-Bz-DTPA = 1-(4-isothiocyanatobenzyl)diethylenetriaminepentaacetic acid;
EDTA = ethylenediaminetetraacetic acid;
chelant is equivalent to ligand;
complex is equivalent to chelate;
conjugate means a chelant or complex covalently attached to an antibody or antibody fragment; and
antibodies mean CC-49, CC-83 and B72.3 and their fragments such as Fab and F(ab')$_2$. Other possible antibodies are given hereinbefore. The hybridoma cell line B72.3 is deposited in the American Type Culture Collection, having the accession number ATCC HB 8108, and the other named murine monoclonal antibodies bind to epitopes of TAG-72, a tumor associated antigen.

The invention will be further clarified by a consideration of the following examples, which are intended to be purely exemplary of the use of the invention.

Preparation of Starting Materials

EXAMPLE A

Preparation of d,l-2-bromo-4-(4-nitrophenyl)butanoic acid, methyl ester

To a solution of 5 ml of carbon tetrachloride and 15 ml (0.2 mole) of thionyl chloride was added 10.46 g (0.05 mole) of 4-(4-nitrophenyl)butanoic acid under a nitrogen atmosphere. The solution was brought to reflux for 1 hour with initial liberation of hydrogen chloride gas and sulphur dioxide gas. To the warm solution was added 11.0 g (0.06 mole) of N-bromosuccinimide in 25 ml of carbon tetrachloride and three drops of 48 percent aqueous hydrogen bromide catalyst. Bromine gas liberation was noted. The dark red solution was refluxed for 35 minutes. The solution was cooled and poured into 100 ml of methanol with stirring. TLC analysis (60:40 ethylacetate:hexane v:v) indicated a new product ($R_f$=0.69, silica plates). The excess solvent was removed by rotary evaporation and the dark red oil was filtered through a flash silica gel pad (1 in. ×5 in.) using methylene chloride as the eluent. Evaporation of the solvent gave a clear oil, yield 15.43 g, which was a 85:15 mixture of the titled product: methyl ester of the starting butanoic acid derivative. The titled product was characterized by:

$^1$H NMR (CDCl$_3$) 8.16(d), 7.38(d), 4.20(dd), 3.79(s), 2.88 (m), 2.38(m);

$^{13}$C NMR (CDCl$_3$, 75 MHz) 169.6, 147.5, 129.3, 123.7, 53.0, 44.4, 35.5, 33.0.

EXAMPLE B

Preparation of α-[2-(4-nitrophenyl)ethyl]-1,4,7,10-tetraazacyclododecane-1-acetic acid, 1-methyl ester To a stirred solution of 1.72 g (10.0 mmole) of 1,4,7,10-tetraazacyclododecane in 17 ml of pentene stabilized chloroform was added 2.07 g (5.82 mmole) of d,l-2-bromo-4-(4-nitrophenyl)butanoic acid, methyl ester (prepared by the procedure of Example A) over five minutes under a nitrogen atmosphere with stirring. The reaction mixture was stirred for 48 hours at about 25° C. TLC (using Solvent System 2, on Analtech silica gel plates) indicated the formation of the title product ($R_f$=0.73). The yellow chloroform solution was applied to a 1 inch×16 inch flash silica gel column (pre-eluted with 5 percent methanolic chloroform), eluted with 250 ml of 5 percent methanolic chloroform, followed by elution with Solvent System 2. Fractions containing pure title product were combined and evaporated to provide 2.15 g (5.46 mmole, 94 percent) of the title product as a light yellow glass. Trituration of a chloroform solution of this glass with diethyl ether resulted in precipitation of a white powder (MP=156°-59° C.) of analytical purity and characterized by:

$^1$H NMR (CDCl$_3$) 8.14(d), 7.39(d), 3.71(s), 3.39(dd), 2.5-3.0(m), 2.08(m), 2.01(m);

$^{13}$C NMR (CDCl$_3$, 75 MHz) 172.7, 149.3, 146.4, 129.2, 123.6, 62.3, 51.2, 48.9, 47.2, 45.8, 45,4, 32.8, 30.9.

EXAMPLE C

Preparation of 2-bromo-2-(4-nitrophenyl)ethanoic acid, methyl ester

A mixture of p-nitrophenylacetic acid (25.0 g, 0.14 mole) and thionyl chloride (15.1 ml, 0.21 mole) in dry benzene (100 ml) was stirred at reflux under a N$_2$ pad for three hours. The mixture was then evaporated to dryness in vacuo. The residue was dissolved in carbon tetrachloride and stirred at reflux under a nitrogen pad. Bromine (7.2 ml, 0.14 mole) was added in small portions over a period of three days to the refluxing mixture. The reaction mixture was allowed to cool and the acid chloride was quenched with methanol (50 ml, added slowly). The resulting bromoester (27 g, 71 percent) was recovered as a yellow oil by distillation at reduced pressure (BP=168° C. at 1.1 mm) through a six-inch column of glass helices. The structure of the title product was confirmed by:

$^1$H NMR (CDCl$_3$) 8.25(d), 7.81(d), 5.51(s), 3.86(s).

EXAMPLE D

Preparation of α-(4-nitrophenyl)-1,4,7,10-tetraazacyclododecane-1-acetic acid, 1-methyl ester To 529 mg (2.068 mmole) of 2-bromo-2-(4nitrophenyl)ethanoic acid, methyl ester (prepared by the procedure of Example C) in 20 ml of acetonitrile was added all at once a solution of 354 mg (2.068 mmole) of 1,4,7,10-tetraazacyclododecane in 20 ml of acetonitrile containing just enough methanol to effect complete solution. The resulting pink solution was stirred for 1.5 hours then concentrated in vacuo at 35° C. to a low volume. This crude monoestertetraamine was purified by silica gel chromatography eluting with 20 percent (wt/v) NH$_4$OAc/CH$_3$OH. The purified monoestertetraamine thus isolated as the triacetate salt was then converted to the free amine. Thus, 270 mg in 3 ml of water was treated at 0° C. with aqueous K$_2$CO$_3$ (10 percent wt/wt) to a pH of 11. The basic solution was then extracted with 10 ml of chloroform, five times, and the chloroform layers combined, dried over sodium sulfate and concentrated to give 160 mg (42 percent yield) of the desired monoestertetraamine, characterized by NMR and fast atom bombardment mass spectrometry ([M+H]$^+$=366) and by:

1H NMR (CDCl$_3$) 8.12(d), 7.44(d), 4.75(s), 3.76(s), 2.67-2.44(m);

$^{13}$C NMR (CDCl$_3$) 171.5, 147.6, 144.0, 130.0, 124.0, 67.0 49.8, 47.9, 46.9, 46.0.

EXAMPLE E

Preparation of N-(2-methoxy-5-nitrobenzyl)-1,4,7,10-tetraazacyclododecane

To a stirred chloroform solution (20 ml) containing 2.9 g of 1,4,7,10-tetraazacyclododecane (16.8 mmole) was added a chloroform solution (20 ml) containing 2.1 g of 2-methoxy-5-nitrobenzyl bromide (8.5 mmole) in one portion. After stirring at room temperature for three hours the reaction mixture was filtered and the filtrate concentrated (in vacuo) to give a residue which was chromatographed (silica, Solvent System 3). The monoalkylated product was isolated in 79 percent yield (MP=154°-156° C.), and characterized by:

13$_C$ NMR (CDCl$_3$) 162.47, 140.63, 127.92, 125.49, 124.53, 109.91, 55.88, 53.25, 50.90, 47.18, 45.45, 45.29.

EXAMPLE F

Preparation of N-(2-hydroxy-5-nitrobenzyl)-1,4,7,10-tetraazacyclododecane

To a 1,4-dioxane solution (20 ml) of 1,4,7,10-tetraazacyclododecane (2.3 g, 14 mmole) was added a dioxane solution (15 ml) of 2-hydroxy-5-nitrobenzyl bromide (1.2 g, 7 mmole) in one portion with constant stirring. After several minutes K$_2$CO$_3$ (1 g) was added and stirring continued for 1 hour at room temperature. The reaction mixture was then filtered and the filtrate concentrated in vacuo to give a yellow semi-solid which was chromatographed (column) on silica gel eluting with Solvent System 5. The desired monoalkylated product was isolated from the last ⅓ of bright yellow eluent which also contained unreacted amine. After concentration, the yellow oil was triturated with CHCl$_3$ (100 ml) and filtered to remove CHCl$_3$-soluble amine starting material. The final product was then isolated in pure form as a yellow solid (1.2 g, 55 percent); (MP=142°–145° C.) and further characterized by:

$^{13}$C NMR (D$_2$O) 25.04, 25.28, 26.83, 31.80, 36.54, 101.88, 107.22, 110.92, 111.80, 115.26, 159.99.

EXAMPLE G

Preparation of 1-[2-(4-nitrophenyl)ethyl]-1,4,7,10-tetraazacyclododecane

To a stirred solution of 3.50 g (20.3 mmole) of 1,4,7,10-tetraazacyclododecane in 50 ml of pentene stabilized chloroform was added dropwise over a five minute period with vigorous stirring under a nitrogen atmosphere 4.00 g (17.4 mmole) of 1-(2-bromoethyl)-4-nitrobenzene.

Stirring was continued for about 18 hours at room temperature (about 25° C.) whereupon crystals of amine hydrobromide precipitated from solution. The entire reaction mixture was applied to a flash silica gel column (1 in×18 in) which had been pre-eluted with 5 percent methanol in chloroform; 200 ml of this solution was applied as an eluent, followed by elution with Solvent System 3. From the desired product was separated 1.45 g (9.7 mmole) of p-nitrostyrene (R$_f$=0.98; Solvent System 1). The desired monofunctional title product was isolated as an orange-yellow oil (2.27 g, 7.06 mmole, 40.6 percent) which solidified upon standing (R$_f$=0.73, Solvent System A sample of the titled product was recrystallized from CHCl$_3$/cyclohexane and showed the following characteristics: MP=146.5°–148.5° C.;

1H NMR (CDCl$_3$) 8.135(d, m), 7.395(d, m), 2.91(t), 2.77(t), 2.72(t), 2.50(t), 2.60(s);

$^{13}$C NMR (CDCl$_3$, 75 MHz) 148.5, 146.7, 129.6, 123.4, 55.5, 51.4, 46.9, 45.9, 45.1, 33.7.

EXAMPLE H

Preparation of 1-(4-nitrobenzyl)-1,4,7,10-tetraazacyclododecane.

In 50 ml of chloroform was added 3.5 g (20.3 mmole) of 1,4,7,10-tetraazacyclododecane and 1.7 g (7.87 mmole) p-nitrobenzyl bromide and the mixture stirred under nitrogen for 24 hours at 25° C. The chloroform slurry of hydrobromide salt was then applied to a 1 in.×17 in. column of flash silica gel (Solvent System 3). There was obtained 2.13 g (6.93 mmole) of the title product as a pale yellow solid of analytical purity in 88 percent yield (R$_f$=0.58, Solvent System 3), MP=128°–129° C., and further characterized by:

$^1$H NMR (CDCl$_3$) 8.19 (d), 7.49 (d), 3.69 (s), 2.82 (t), 2.70 (t), 2.59 (m);

$^{13}$C NMR (CDCl$_3$, 75 MHz) 147.2, 128.4, 123.8, 58.8, 51.7, 47.1, 46.3, 45.1.

(No Example I; to avoid confusion with later biology example numers).

EXAMPLE J

Preparation of 1-(4-aminobenzyl)-1,4,7,10-tetraazacyclododecane

In 10 ml of methanol was dissolved 690 mg (2.25 mmole) of 1-(4-nitrobenzyl)-1,4,7,10-tetraazacyclododecane (prepared by the procedure of Example H). To the solution was added 350 mg of 10 percent palladium on carbon catalyst. Excess hydrogen was purged through the solution at 25° C. Within 45 minutes TLC indicated that the title product was prepared (R$_f$=0.33, Solvent System 3). Chromatographic purification of the formed titled product was conducted on 1 in.×16 in. flash silica column (Solvent System 3) and provided 480 mg (77 percent) of the title product as a pale yellow, clear oil.

The free base title product (103 mg, 0.37 mmole) was converted to the hydrochloride salt by bubbling anhydrous hydrogen chloride through ethanol solutions of the free base. The resulting tetrahydrochloride salt of the title product, after washing with cold ethanol and drying in vacuo, was obtained in a yield of 147 mg (0.347 mmole), MP=255°–260° C. (dec), and was further characterized by:

$^1$H (D$_2$O, pD=1.9) 7.56 (d), 7.47 (d), 3.95 (s), 3.28 (t), 3.23 (t), 3.09 (t), 2.96 (t);

$^{13}$C NMR (D$_2$O, pD=1.9, 75 MHz) 138.3, 134.2, 132.2, 126.0, 58.5, 50.3, 46.7, 44.6, 44.3.

EXAMPLE K

Preparation of 2-methoxy-5-nitrobenzylnitrile

To a solution of sodium cyanide (6 g, 121.9 mmole) in water (5.3 ml) at 70° C. was added in small portions with stirring a hot solution of 2-methoxy-5-nitrobenzylbromide (25 g., 101.6 mmole) in ethanol (15 ml). The reaction mixture was then refluxed for 1.5 hours, cooled, and filtered. The filter cake was washed with acetonitrile and the filtrate was evaporated in vacuo to yield 2-methoxy-5-nitrobenzylnitrile (19.5 g., 100 percent) as a tan solid. The product was characterized by:

$^{13}$C NMR (CDCl$_3$) 161.4, 141.0, 125.7, 124.6, 119.8, 116.5, 110.2, 56.3, 18.8.

EXAMPLE L

Preparation of 2-methoxy-5-nitrophenylacetic acid

A slurry of 2-methoxy-5-nitrobenzylnitrile (19.5 g) (prepared by the procedure of Example K) in conc. HCl (20 ml) was refluxed for three hours. After cooling, the crude product was recovered by filtration and washed with water. The solid was taken up in hot aqueous sodium hydroxide and filtered while hot. The orange solution was cooled and acidified with HCl. The precipitate was filtered, washed with water, and dried to yield 2-methoxy-5-nitrophenylacetic acid as a white solid (15 g, 70 percent). The product was characterized by:

$^{13}$C NMR (CDCl$_3$-CD$_3$OD) 172.8, 162.5, 140.7, 126.2, 124.7, 124.1, 109.7, 55.8, 35.0.

EXAMPLE M

Preparation of
α-bromo-(2-methoxy-5-nitrophenyl)acetic acid, methyl ester

To a slurry of 2-methoxy-5-nitrophenylacetic acid (2.266 g, 10.74 mmole) (prepared by the procedure of Example L) in dry benzene (50 ml) was added thionyl chloride (4.0 ml, 54.8 mmole). A drying tube and condenser were placed on the flask and the mixture was refluxed for 2 hours. The resulting yellow solution was concentrated in vacuo to a small volume and taken up in dry carbon tetrachloride. Bromine (0.6 ml, 11.6 mmole) was added and the solution was refluxed for two days with the exclusion of atmospheric moisture. The reaction mixture was concentrated to a small volume and methanol (50 ml) was added. After evaporation of excess methanol in vacuo the resulting oil was purified chromatographically (silica gel, methylene chloride-hexane 4:1). The title product (2.399 g., 74 percent) was obtained as a yellow oil. The product was characterized by:

$^1$H NMR (CDCl$_3$) 8.45(dd), 8.15(dd), 6.95 (d), 5.75(s), 3.99(s), 3.78(s).

EXAMPLE N

Preparation of
α-(2-methoxy-5-nitrophenyl)-1,4,7,10-tetraazacyclodo-decane, 1-acetic acid, methyl ester A solution of α-bromo (2-methoxy-5-nitrophenyl)acetic (2.399 g, 7.89 mmole) (prepared by the procedure of Example M) in chloroform (10 ml) was added to a stirred solution of 1,4,7,10-tetraazacyclododecane (2.72 g, 15.79 mmole) in chloroform (50 ml The mixture was stirred at room temperature for 2 hour The cloudy mixture was then concentrated to a small volumn in vacuo at room temperature. The crude product was purified by chromatography (silica gel, Solvent System 3). The title compound was recovered as a yellow solid (2.60 g, 83 percent) and characterized by:

$^{13}$C NMR (CDCl$_3$) 170.7, 161.6, 139.9, 125.0, 124.5, 124.2, 110.2, 59.5, 55.5, 50.5, 48.0, 47.3, 45.6, 44.3, 43.5.

EXAMPLE O

Preparation of d,l-2-bromo-4-(4-nitrophenyl)butanoic acid isopropyl ester 4-(4-Nitrophenyl)butanoic acid (21.0 g, 0.10 mole) was added to a solution of carbon tetrachloride (10 ml) and thionyl chloride (30 ml, 0.4 mole) under a nitrogen atmosphere using the procedure of Harpp et al., *J. Org. Chem* 40, 3420–27 (1975). The solution was brought to reflux for 1 hour with initial rapid liberation of hydrogen chloride and sulfur dioxide. At this point, N-bromosuccinimide (22.0 g, 0.12 mole) was added as a solution in carbon tetrachloride (50 ml) and 8 drops of 48% aqueous hydrogen bromide catalyst was added to the warm solution whereupon bromine liberation was noted. The dark red solution was refluxed for an additional 35 minutes. The solution was cooled and poured into isopropanol (400 ml) with stirring. TLC analysis (methylene chloride, silica gel plates) revealed a new product (R$_f$=0.73). The excess solvent was removed and the dark red oil was filtered through a flash silica gel pad (3 in.×6 in.) using methylene chloride as an eluent. The solvent was removed in vacuo and the light yellow oil was applied to a flash silica gel column (3 in.×18 in.) and eluted with methylene chloride to afford 25.0 g (0.076 mole) of the titled bromoester product as a clear oil in 75% yield as a isopropanol solvate which contained less than 5% of unbrominated ester and characterized by:

$^1$H NMR (CDCl$_3$) 8.16(d, 2H), 7.38(d, 2H), 5.05(septet, 1H), 4.14(dd, 1H), 2.88(m, 4H), 2.39(m, 4H), 1.29(d, 6H);

$^{13}$C NMR (CDCl$_3$) 168.7, 147.7, 129.3, 123.8, 69.9, 45.1, 35.6, 33.0, 21.5, 21.2.

EXAMPLE P

Preparation of
α-[3-(4-nitrophenyl)propyl]-1,4,7,10-tetraazacyclodo-decane-1-acetic acid, 1-methyl ester To a stirred solution of 3.137 g (18.2 mmoles) of cyclen free base in 30 ml of pentene stabilized chloroform was added 4.81 g (14.6 mmoles corrected) of d,l-2-bromo-4-(4-nitrophenyl)-butanoic acid isopropyl ester (prepared by the procedure of Example O) over a 5 minute period under a nitrogen atmosphere with stirring. The reaction solution was stirred for 24 hours at room temperature. TLC analysis (Solvent System 2) revealed conversion to the titled monoalkylation product (R$_f$=0.78 detection withninhydrin, iodine, and UV activity). The yellow chloroform solution was applied to a 1 in.×17 in. flash silica gel column which had been pre-eluted with 5% methanolic chloroform. Elution with 300 ml of this solvent system was followed by elution with Solvent System 2 and provided fractions containing pure titled product which were combined and evaporated affording 4.85 g (5.46 mmoles) of the titled product free base as a light oil in 79% yield and further characterized by:

$^1$H NMR (CDCl$_3$) 8.15(d, 2H), 7.40(d, 2H), 5.07(p, 1H), 3.35(dd, 1H), 2.65–3.0(m, 13H), 2.5–2.64(m, 4H), 2.14(m, 1H), 2.00(m, 1H), 1.28(dd, 6H);

$^{13}$C NMR (CDCl$_3$) 171.6, 149.5, 146.5, 129.2, 123.6, 68.1, 62.7, 49.2, 47.5, 45.9, 45.7, 32–9, 31.0, 22.1, 22.0;

IR (CDCl$_3$) cm$^{-1}$ 3231(N—H), 2978, 2933, 1721(ester carbonyl), 1601, 1512, 1458, 1345, 1107;

Fast atom bombardment mass spectrum, m/e 422 (M+H)]+, 408, 392.

Preparation of Final Products—Ligands

EXAMPLE 1

Preparation of
α-(4-nitrophenyl)-1,4,7,10-tetraazacyclododecane-1,4,7,10-tetraacetic acid, monomethyl, triethyl ester In 46 ml of acetonitrile containing 4.6 g (33.3 mmole) of freshly powdered anhydrous potassium carbonate was dissolved 700 mg (1.91 mmole) of α-(4-nitrophenyl)-1,4,7,10-tetraazacyclododecane-1-acetic acid, 1-methyl ester (prepared by the procedure of Example D). To this suspension was added all at once 1.022 g (6.12 mmole) of ethyl bromoacetate. After four hours of stirring at room temperature, the suspension was vacuum filtered, the filter cake washed with 15ml of acetonitrile, two times, and the filtrate evaporated in vacuo at 38° C. to give the crude titled tetraester as a purple solid. The tetraester was then purified by silica gel chromatography eluting with 5 percent C$_2$H$_5$OH/CHCl$_3$ then Solvent System 3, to give 620 mg (0,988 mmole, 52 percent) of the desired product. This product was characterized by fast atom bombardment mass spectrometry ([M+H]+ =624) and futher characterized by:

$^1$H NMR (CDCl$_3$) 8.24(d), 7.45(d), 4.94(s), 4.35–4.10(m), 3.79(s), 3.75–1.84(m), 1.34–1.22(m);

$^{13}$C NMR (CDCl$_3$) 174.3, 173.8, 173.6, 171.5, 147.6, 138.9, 131.5, 123.4, 64.8, 61.5, 61.4, 60.2, 55.4, 55.0, 53.1, 52.9, 52.7, 52.4, 51.9, 51.7, 48.8, 48.3, 44.9, 19.1, 14.1.

EXAMPLE 2

Preparation of
α-(4-nitrophenyl)-1,4,7,10-tetraazacyclododecane-1,4,7,10-tetraacetic acid In 30 ml of 6N HCl was dissolved 300 mg (0.478 mmole) of α-(4-nitrophenyl)-1,4,7,10-tetraazacyclododecane-1,4,7,10-tetraacetic acid, monomethyl, triethyl ester (prepared by the procedure of Example 1) and the mixture was heated at reflux overnight. At the end of this reflux period, the solution was concentrated in vacuo at 70° C. to give a yellow solid. This solid was dissolved in 3 ml of water, filtered, and the filtrate evaporated to give 253 mg (0.378 mmole, 79 percent) of the crude product. This product was purified by preparative TLC [silica gel, developed in 20 percent NH$_4$OAc/CH$_3$OH (wt/v)] and characterized by fast atom bombardment mass spectrometry ([M+H]+ =526) and futher characterized by:

$^1$H NMR (D$_2$O) 8.21(d), 7.42(d), 4.83(s), 3.83–2.19(m), 1.92(s);

$^{13}$C NMR (D$_2$O) 175.0, 173.6, 171.8, 167.0, 166.3, 146.9, 138.3, 130,1, 123.0, 62.2, 54.0, 53.0, 52.2, 50.4, 97.3, 46.8, 44.8, 42.8, 20.0.

EXAMPLE 3

Preparation of
α-(4-aminophenyl)-1,4,7,10-tetraazacyclododecane-1,4,7,10-tetraacetic acid; (BA-DOT A)

Method A

Catalytic hydrogenation of the nitro group of the tetraacid (prepared by the procedure of Example 2) was performed using Adams catalyst (PtO$_2$) and hydrogen in essentially quantitative yield to give the titled product. This product was characterized by fast atom bombardment ([M+H]+ =496) and anion exchange HPLC (on Q-Sepharose ™) and futher characterized by:

$^1$H NMR (D$_2$O) 8.12(d), 7.86(d), 5.66(s), 4.73–4.57(m), 4.27–3.78 (m), 3.39–2.91(m);

$^{13}$C NMR (D$_2$O) 176.54, 176.52, 176.46, 141.1,128.9, 120.9, 112.5, 65.0, 55.9, 55.7, 53.6, 49.7, 49.5, 49.3, 45.7, 45.4, 44.9, 44.6, 41.4.

Method B

Another method to synthesize this compound was to convert the monoester tetraamine compound from Example D to the monoacid tetraamine compound (6N HCl, reflux overnight), followed by aqueous alkylation using bromoacetic acid, then reduction of the nitro group to the amine group (PtO$_2$ catalyst) to give a product identical to that described above.

EXAMPLE 4

Preparation of
α-(4-nitrophenyl)-1,4,7,10-tetraazacyclododecane-1,4,7-triacetic acid In 60 ml of 6N HCl was dissolved 2.0 g (5.48 mmole) of the monoester tetraamine compound (prepared by the procedure of Example D). The mixture was heated to 95° C. overnight (about 10 hours) after which it was concentrated in vacuo at 75° C. to give 2.53 g (5.11 mmole, 96 percent) of the monoacid tetraamine tetrahydrochloride as a yellow solid.

The above monoacid tetraamine tetrahydrochloride (0.5 g, 1.0 mmole) was dissolved in 15 ml of water and adjusted to pH 9 with NaOH. A separate solution of bromoacetic acid was prepared (0.71 g, 5.13 mmole) and added to the water solution of the monoacid tetraamine. The pH of the solution was again adjusted to 9 and maintained at this pH during the reaction by small additions of 1.0N NaOH. While the reaction was stirred, aliquots were removed at different time points and the progress of the alkylation was monitored by anion exchange HPLC. When the amount of dialkylation product (total of three acetate groups present) had reached a maximum, the whole reaction mixture was lyophilized to give a dark solid. This crude mixture of alkylated products was then purified by silica gel chromatography (eluting with Solvent System 1), followed by preparative anion exchange chromatography (eluting with a gradient of 0–100 percent 1M NH$_4$OAc), then by preparative TLC plates (developed in Solvent System 4) and finally by silica gel chromatography (eluting with Solvent System 4). This extensive purification procedure gave, as a yellow solid, 30 mg (0.06 mmole, 6.0 percent) of the title product. This product was characterized by fast atom bombardment mass spectrometry ([M+H]+ =468), anion exchange HPLC and futher characterized by:

$^1$H NMR (D$_2$O) 8.12(bs), 7.35(bs), 4.76(s), 3.57–3.44(m), 2.97–1.83(m), 1.80(s);

$^{13}$C NMR (D$_2$O) 181.75, 180.68, 179.00, 175.37, 147.70, 141.22, 133.08, 123.53, 68.44, 59.72, 56.00, 52.80, 49.96, 49.29, 47.86, 45.36, 44.26, 42.78, 42.25, 23.72.

EXAMPLE 5

Preparation of
α-(4-aminophenyl)-1,4,7,10-tetraazacyclododecane-1,4,7-triacetic acid pentahydrochloride and
α-(4-aminophenyl)-1,4,7,10-tetraazacyclododecane-1,4,10-triacetic acid pentahydrochloride A crude mixture of alkylated products was prepared by the procedure described in Example 4. This crude mixture was chromatographed on a silica gel column eluting with 20 percent NH$_4$OAc/CH$_3$OH (wt:v). The appropriate fractions from this column were combined and evaporated to dryness. The crude product, having substantial amounts of NH$_4$OAc, was dissolved in 80 ml of NANOpure ™ water and lyophilized to yield a light brown solid. This solid was dissolved in 20 ml of NANOpure ™ water, shaken with PtO$_2$ catalyst under a H$_2$ atmosphere until hydrogen uptake stopped. The catalyst was separated by vacuum filtration, and the filtrate lyophilized to give a yellow solid. The solid was dissolved in 3 ml of Solvent System 4 and chromatographed on silica gel using Solvent System 4. The pooled fractions were then stripped in vacuo and lyophilized to yield 779.6 mg of light yellow solid. $^{13}$C NMR and proton NMR suggests that this product is a 50/50 mixture of the two possible geometric isomers. The isomeric mixture was contacted with excess HCl and lyophilized to yield 548.4 mg (61 percent yield) of the title products. M.P.>270° C. Anion exchange chromatography (HPLC System III) showed one major peak (>94 percent purity); fast atom bombardment mass spectrum indicated the geometrical isomers [M+H]+ =438.

EXAMPLE 6

Preparation of
α-[2-(4-nitrophenyl)ethyl]-1,4,7,10-tetraazacyclododecane-1,4,7,10-tetraacetic acid 1,4,7,10-tetramethyl ester To a solution of 1.43 g (3.63 mole) of α-[2-(4-nitrophenyl)ethyl]-1,4,7,10-tetraazacyclododecane-1-acetic acid, 1-methyl ester (prepared by the procedure of Example B) in 40 ml of argon purged acetonitrile was added 1.71 g (12.34 mmole) of anhydrous potassium carbonate with vigorous stirring. To the reaction mixture was added 1.78 g (11.61 mmole) of methyl bromoacetate and the reaction mixture was stirred at about 25° C. for 48 hours. TLC analysis indicated formation of a new product ($R_f$=0.62, Solvent System 2). To the slurry was added 6.0 g of flash silica gel and acetonitrile was removed on a rotary evaporator. The resulting material was applied to 1 in. × 16 in. silica column which had been pre-eluted with 5 percent methanolic chloroform. About 400 ml of the prepared solution was used to elute several nonpolar impurities and unreacted alkylating agent. Then Solvent System 2 was applied, fractions containing product ($R_f$= 0.62) were collected, combined and evaporated to provide 2.1 g (3.44 mmole, 95 percent) of the titled product as a pale yellow glass. $^1$H NMR indicated this product to be a 2:1 mixture of conformational or geometric isomers.

$^1$H NMR (CDCL$_3$, 50° C. ) 8.137(d), 8.128(d), 7,398(d), 7.385(d), 3.82(s), 3.76(s), 3.75(s), 3.74(s), 3.68(s), 1.5–3.52(m);

$^{13}$C NMR (CDCl$_3$, 50° C., 75 MHz) 175.8, 174.2, 174.1, 174.0, 149.0, 129.5, 129.3, 123.6, 60.1, 55.1, 52.8, 52.7, 52.6, 52.4, 52.2, 52.1, 52.0, 51.2, 51.1, 51.0, 49.1, 48.8, 47.5, 45.2, 34.2, 32.6.

EXAMPLE 7

Preparation of
α-[2-(4-aminophenyl)ethyl]-1,4,7,10-tetraazacyclododecane-1,4,7,10-tetraacetic acid, 1,4,7,10-tetramethyl ester In 25 ml of methanol containing 400 mg of 10 percent palladium-on-carbon catalyst under a nitrogen atmosphere was dissolved 1.41 g (2.31 mole) of α-[2-(4-nitrophenyl)ethyl]-1,4,7,10-tetraazacyclododecane-1,4,7,10-tetraacetic acid, 1,4,7,10-tetramethyl ester (prepared by the procedure of Example 6). Excess hydrogen was purged through the solution at one atmosphere for three hours. TLC indicated the formation of a strongly ninhydrin positive material ($R_f$=0.62, Solvent System 2). The methanolic catalyst slurry was filtered through celite and evaporation of sol vent provided the title product, 1.21 g (2.08 mmole, 91 percent), as a white solid glass (as a 2:1 mixture of conformational isomers). The minor conformational or geometric isomer was separated from the major isomer by flash chromatrography using 10 percent methanolic chloroform to yield the title product as an off white powder (MP=89°–95° C.) and characterized by:

$^1$H NMR (CDCl$_3$, 50° C.) 6.94(d), 6.89(d), 6.69(d), 6.66(d), 3.91(s), 3.80(s), 3.78(s), 3.74(s), 3.73(s), 3.72(s), 3.71(s), 1.5–3.5(m);

$^{13}$C NMR (CDCl$_3$, 50° C., 75 MHz) 176.1,174.0, 173.9, 172.2, 170.4, 169.6, 144.2, 144.1, 130.6, 130.5, 129.5, 129.1, 115.9, 115.8, 62.6, 58.7, 55.1, 54.3, 52.7, 52.5, 52.3, 52.2, 52.1, 52.0, 51.9, 51.8, 51.7, 50.2, 50.0, 47.3, 44.7, 32.8, 31.8, 30.0, 25.2;

Fast atom bombardment mass spectrum, m/e 602 [M+Na$^+$], 618 M+K$^+$]$^+$, [624 M+2Na$^+$-H$^+$]$^+$.

EXAMPLE 8

Preparation of
α-[2-(4-aminophenyl)ethyl]-1,4,7,10-tetraazacyclododecane-1,4,7,10-tetraacetic acid; (PA-DOTA)

In 50 ml of conc. hydrodrochloric acid was dissolved 1.5 g (2.59 mmole) of α-[2-(4-aminophenyl)ethyl]-1,4,7,10-tetraazacyclododecane-1,4,7,10-tetraacetic acid, 1,4,7,10-tetramethyl ester (as the crude 2:1 mixture prepared by the procedure of Example 7). The reaction mixture was refluxed at about 105° C. for six hours. TLC (Solvent System 1) indicated conversion of the ester ($R_f$=0.88) to the title product as the hydrochloride salt ($R_f$=0.43). Excess solvent was removed on a rotary evaporator and the resulting white solid was dried. The title product as the hydrochloride salt was obtained in a yield of 1.6 g and characterized by:

$^1$H NMR (D$_2$O, pD=1.0., 90° C.) 7.48(d), 7.42(d), 2.8–4.3(m), 2.23(m), 2.03(m);

$^{13}$C NMR (D$_2$O, pD=1.0, 90° C. , 75 MHz) 176.4, 174.9, 171.6, 144.7, 132.9, 132.8, 130.4, 125.7, 61.7, 56.8, 56.0, 53.7, 53.1, 51.6, 47.9, 34.3, 37.6,

Fast atom bombardment mass spectrum m/e 524 [M+H]$^+$, 546 M+Na$^+$]$^+$, 568 [M+2Na$^+$-H$^+$]$^+$.

Using flash chromatography and Solvent System 1, any trace impurities of the ester were removed from the title product as the hydrochloride salt. To a 1 in.×23 in. flash silica gel column was applied 1.10 g of the title product, as the hydrochloride salt. Fractions containing only the title product, as the mixed ammonium potassium salt were combined to provide 580 mg.

HPLC analysis indicated the material to be greater than 98 percent area purity at 230 and 254 nm.

Fast atom bombardment mass spectrum, m/e 562 (M+K)$^+$, 584 [M+K$^+$+Na$^+$-H$^+$], 600 [M+2K$^+$-H$^+$]$^+$.

EXAMPLE 9

Isolation of α-[2-(4-aminophenyl)ethyl]-1,4,7,10-tetraazacyclododecane-1,4,10-triacetic acid, mixed ammonium, potassium salt A crude solution containing both the tetra and tri acids (2.05 g) (prepared by the procedure of Example 8) was dissolved in a minimum amount of Solvent System 1 and applied to a 12 in.×3 in. column of flash silica gel which had been pre-eluted with this solvent. Elution of fractions containing the title product ($R_f$=0.63 in Solvent System 1) were collected and afforded 200 mg of α-[2-(4-aminophenyl)ethyl]-1,4,7,10-tetraazacyclododecane-1,4,10-triacetic acid, mixed ammonium, potassium salt. $^1$H and $^{13}$C NMR analysis suggested that this triacid was the symmetrical isomer (1,4,10-triacid positional isomer):

$^1$H NMR (D$_2$O, pD=0.5 with DCl, T=90° C.) 7.52(d), 7.46(d), 3.60(m), 3.54(m), 3.19(m);

$^{13}$C NMR (D$_2$O, pD=0.5, T=90° C.) 176.1, 170.2, 140.0, 132.7, 131.1, 126.1, 57.6, 57.2, 56.1, 54.9, 53.2, 51.5, 51.2, 31.2.

Fast atom bombardment mass spectrum, m/e 466[M+H$^+$]$^+$, 488[M+Na$^+$]$^+$, 504[M+K$^+$]$^+$, 526[M+K$^+$+Na$^+$-H$^+$]$^+$, 542[M+2K-H)]$^+$.

EXAMPLE 10

Preparation of
α-(2-methoxy-5-nitrophenyl)-1,4,7,10-tetraazacyclododecane-1,4,7,10-tetraacetic acid, tetramethyl ester Methyl bromoacetate (565 μl, 5.97 mmole) was added to a stirred mixture of α-(2-methoxy-5-nitrophenyl)-1,4,7,10-tetraazacyclododecane, 1-acetic acid, methyl ester (580 mg, 1.47 mmole) (prepared by the procedure of Example N) and pulverized potassium carbonate (1.15 g, 8.32 mmole) in acetonitrile (20 ml). The reaction mixture was stirred at room temperature for 2 hours. The mixture was then filtered and the filtrate was concentrated to an oil in vacuo. The crude product was purified by chromatography (silica gel, 8 percent methanol in methylene chloride). The title product was obtained as a yellow solid (469 mg, 52 percent), TLC $R_f=0.4$ (silica gel, 10% $CH_3OH$ in $CHCl_3$), and further characterized by:

$^{13}C$ NMR ($CDCl_3$) 173.2, 172.6, 161.2, 139.1,125.1, 124.6, 120.5, 110.7, 57.0, 55.6, 53.5, 52.6, 51.3, 50.8, 46.8, 46.0, 44.0.

EXAMPLE 11

Preparation of
α-(2-methoxy-5-nitrophenyl)-1,4,7,10-tetraazacyclododecane-1,4,7,10-tetraacetic acid A solution of α-(2-methoxy-5-nitrophenyl)-1,4,7,10-tetraazacyclododecane-1,4,7,10-tetraacetic acid, tetramethyl ester (prepared by the procedure of Example 10) in concentrated HCl (5 ml, J. T. Baker ULTREX) was refluxed under a nitrogen atmosphere for 5 hours. The solution was then concentrated to dryness in vacuo to leave a solid residue. This was purified by chromatography (silica gel, Solvent System 6) to yield the title product as an off-white solid (209 mg). This material was converted to the tetrahydrochloride salt and was characterized by:

$^{13}C$ NMR ($D_2O$-DCl, 80° C.) 171.0, 166.9, 161.2, 139.0, 125.5, 119.3, 110.7, 56.8, 54.5, 52.7, 51.0, 49.2, 49.0, 46.3, 42.9.

EXAMPLE 12

Preparation of
α-(2-methoxy-5-aminophenyl)-1,4,7,10-tetraazacyclododecane-1,4,7,10-tetraacetic acid, tetraammonium salt To a solution of α-(2-methoxy-5-nitrophenyl)-1,4,7,10-tetraazacyclododecane-1,4,7,10-tetraacetic acid (157 mg) (prepared by the procedure of Example 11) in water (20 ml) was added platinum oxide (20 mg). This mixture was hydrogenated (1 atmosphere hydrogen) for 1 hour at room temperature. After filtration, the material was further purified by chromatography (silica gel, Solvent System 5) to yield the title compound (141 mg) as an off-white solid, and characterized by:

$^{13}C$ NMR ($D_2O$)-DCl) 175.5, 172.6, 172.3, 159.9, 128.8, 127.5, 124.6, 123.8, 115.5, 61.2, 58.1, 57.3, 55.7, 53.4, 51.6, 49.6, 47.4.

EXAMPLE 13

Preparation of
1-(4-aminobenzyl)-1,4,7,10-tetraazacyclododecane-4,7,10-triacetic acid, 4,7,10-trimethyl ester To 4 ml of argon purged acetonitrile with stirring was added 100 mg (0.236 mmole) of 1-(4-aminobenzyl)-1,4,7-10-tetraaacyclododecane, tetrahydrochloride salt (prepared by the procedure of Example J), 260 mg (1.88 mmole) of potassium carbonate, and 108 mg (0.708 mmole) of methylbromoacetate. The mixture was stirred for 48 hours at 25° C. The salt containing solution was applied to a 1 cm×4 cm flash silica gel column and was eluted with acetonitrile. Fractions containing the desired product were combined and the solvent removed by rotary evaporation to provide 65 mg (0.132 mmole, 56 percent) of the title product which was further characterized by:

$^1H$ NMR ($CDCl_3$) 7.29 (d), 6.75 (d), 4.62 (s), 4.20 (broad 3.70 (s), 3.69 (s), 3.64 (s), 3.62 (t), 3.27 (s), 3.06 (t), 2.82 (broad t), 2.79 (broad t);

$^{13}C$ NMR ($CDCl_3$, 75 MHz) 171.4, 171.0, 148.4, 132.8, 117.5, 115.0, 55.9, 55.3, 54.7, 53.1, 51.7, 51.4, 50.6, 50.5, 47.4.

EXAMPLE 14

Preparation of
1-(4-aminobenzyl)-1,4,7,10-tetraazacyclododecane-4,7,10-triacetic acid, hydrochloride salt In 2 ml of 6N hydrochloric acid, 42 mg (0.085 mmole) of 1-(4-aminobenzyl)-1,4,7,10-tetraazacyclododecane-4,7,10-triacetic acid, 4,7,10-trimethyl ester (prepared by the procedure of Example 13) was heated to 80° C. for 2 hours. TLC indicated several products ($R_f=0.60$ for the desired title product, Solvent System 1). Removal of solvent afforded 41 mg of crude title product.

EXAMPLE 15

Preparation of
1-[2-(4-nitrophenyl)ethyl]-1,4,7,10-tetraazacyclododecane-4,7,10,-triacetic acid, 4,7,10-trimethyl ester To a solution of 2.24 g (6.97 mmole) of 1-[2-(4-nitrophenyl)ethyl]-1,4,7,10-tetraazacyclododecane (prepared by the procedure of Example G) in 75 ml of argon purged acetonitrile was added with vigorous stirring 3.17 g of anhydrous potassium carbonate. To this reaction mixture was added dropwise over a five minute period 3.20 g (20.9 mmole) of methylbromoacetate. The reaction mixture was stirred for 17 hours under argon atmosphere. TLC analysis showed conversion of the starting material ($R_f=0.73$, Solvent System 1) to a new product ($R_f=0.46$, Solvent System 1). To the solution was added 70 ml of chloroform and the solution with the suspended salt was applied to a 1 in.×7 in. flash silica column. The product was eluted using 10 percent methanol in chloroform to yield 2.95 g of the title product as an amber oil which formed a friable glass upon vacuum drying (78 percent). The title product was characterized by:

$^1H$ NMR ($CDCl_3$) 8.17 (m,m), 7.4–7.66 (m), 2.38–3.95 (m).

$^{13}C$ NMR ($CDCl_3$, 75 MHz) 171.5, 171.2, 146.7, 144.5, 130.3, 123.9, 56.0, 55.2, 53.5, 53.4, 52.6, 51.9, 51.8, 50.6, 48.1, 29.5.

EXAMPLE 16

Preparation of
1-[2-(4-aminophenyl)ethyl]-1,4,7,10-tetraazacyclododecane-4,7,10-triacetic acid, 4,7,10-trimethyl ester In 50 ml of methanol was dissolved 2.8 g (5.18 mmole) of crude 1-[2-(4-nitrophenyl)ethyl]-1,4,7,10-tetraazacyclododecane-4,7,10-triacetic acid, 4,7,10-trimethyl ester (prepared by the procedure of Example 15). To the stirred solution which was purged with nitrogen was added 10 percent palladium on carbon catalyst (600 mg). The solution was maintained under an atmosphere of nitrogen, and then hydrogen (1 atm, 20°-25° C.) was purged through the stirred solution for 2.5 hours. The solution was then purged for several minutes with nitrogen and the catalyst removed by filtration through a short bed of celite. TLC analysis (10 percent methanol in chloroform) revealed the title product ($R_f$=0.14). The title product was eluted with chloroform from silica gel to yield 2.2 g (4.33 mmole, 83 percent) as a white glass and characterized by:

$^1$H NMR (CDCl$_3$) 7.03 (d,m), 6.63 (d), 3.4–3.6 (m), 2.7–3.2 (m);

$^{13}$C NMR (CDCl3, 75 MHz) 171.4, 171.2, 145.6, 129.7, 125.6, 115.5, 55.9, 54.4, 54.3, 53.0, 52.8, 51.8, 51.6, 50.3, 47.8, 28.6;

Fast atom bombardment mass spectrum, m/e 508 [M+H+]+.

EXAMPLE 17

Preparation of
1-[2-(4-aminophenyl)ethyl]-1,4,7,10-tetraazacyclo-dodecane-4,7,10-triacetic acid, hydrochloride salt; (EA-DO3A)

In 30 ml of conc. HCl was dissolved 850 mg (1.69 mmole) of 1-[2-(4-aminophenyl)ethyl]-1,4,7,10-tetraazacyclododecane-4,7,10-triacetic acid, 4,7,10-trimethyl ester (prepared by the procedure of Example 16). The solution was stirred at 70°-80° C. for 2.5 hours and the solution allowed to cool with stirring to 25° C. and the stirring continued for about 18 hours. Solvent was removed on a rotary evaporator at reduced pressure (10 mm, 75° C.). Solvate and excess hydrogen chloride were removed from the resulting clear oil by vacuum drying (10$^{-1}$ mm, 45° C.). The title product was provided as a white solid, in a yield of 890 mg, ($R_f$=0.46, Solvent System 2) and further characterized by:

$^1$H NMR (D$_2$O, pD=1.9, T=90° C.) 7.50(d), 7.41(d), 4.26(s), 3.43–3.68(m), 3.0–3.3(m);

$^{13}$C NMR (D$_2$O, pD=1.9, T=90° C.) 176.7, 170.9 139.8, 133.0, 131.2, 125.9, 57.5, 57.1, 55.4, 54.4, 52.7, 51.0, 50.6, 31.3;

Fast atom bombardment mass spectrum, m/e 466 (M+H+), 488 [M+Na+], 510 [M+2Na+-H+]+.

HPLC analysis indicated greater than 92 percent area purity (254 mm) using a 10 cm Partisil-5 OD53 RAC II reverse phase column. The eluent was 10 percent acetonitrile in 0.05M pH=7.0 potassium phosphate solution.

EXAMPLE 18

Preparation of
1-[2-(4-isothiocyanatophenyl)ethyl]-1,4,7,10-tetraazacyclododecane-4,7,10-triacetic acid; (SCN-EA-DO3A)

1-[2-(4-Aminophenyl)ethyl]-1,4,7,10-tetraazacyclododecane-4,7,10-triacetic acid, hydrochloride salt (prepared by the procedure of Example 17, 106 mg, 0.21 mmole) was dissolved in 2 ml of water under a nitrogen atmosphere with stirring. Sodium bicarbonate (105.6 mg, 1.26 mmole) was slowly added to prevent frothing from carbon dioxide evolution (resulting pH=8.0). Thiophosgene (16.8 μl, 0.22 mmole) was added and after one hour of vigorous stirring, TLC analysis (20 percent water in acetonitrile) indicated conversion of starting material ($R_f$=0.12) to title product ($R_f$=0.26). The solvent was removed from the crude product by rotary evaporation to afford 130 mg of title product which contained sodium chloride. Infrared analysis of this material (KBr pellet) confirmed the presence of the isothiocyanate moiety (SCN=2150 cm$^{-1}$).

EXAMPLE 19

Preparation of
1-[2-(4-nitrophenyl)ethyl]-1,4,7,10-tetraazacyclododecane-4,7,10-triacetic acid, triethyl ester To 5 ml of a stirred acetonitrile solution containing 395 mg (1.12 mmole) of 1-[2-(4-nitrophenyl)ethyl]-1,4,7,10-tetraazacyclododecane (prepared by the procedure of Example G) and 1.5 g (11 mmole) of K$_2$CO$_3$ was added 496 μl (4.5 mmole) of ethyl bromoacetate in one portion. After heating at 68° C. under a N$_2$ atmosphere for one hour, the resulting suspension was filtered. The filter cake was washed with CH$_3$CN (2×10 ml). The filtrate was then concentrated to give the crude product as a viscous oil, triturated with 30 ml of diethyl ether, and concentrated to give 650 mg (100% yield) of 1-[2-(4-nitrophenyl)ethyl]-1,4,7,10-tetraazacyclododecane-4,7,10-triacetic acid, triethyl ester and characterized by:

$^1$H NMR (CDCl$_3$) 8.2(d), 7.6(d), 4.3(q), 2.6–3.8(m), 1.55(t);

Fast atom bombardment mass spectrum [M+H]+=588.

EXAMPLE 20

Preparation of
1-[2-(4-nitrophenyl)ethyl]-1,4,7,10-tetraazacyclododecane-4,7,10-triacetic acid To a suspension of 200 mg (0.35 mmole) of 1-[2-(4-nitrophenyl)ethyl]-1,4,7,10-tetraazacyclododecane-4,7,10-triacetic acid, triethyl ester (prepared by the procedure of Example 19) in 15 ml of water was added 59 μl of NaOH (50% wt/wt, 3 eq). The mixture was stirred at 80° C. for 6 hours. The resulting homogeneous orange solution was then cooled to room temperature and freeze-dried to yield a brown solid which was purified by HPLC (Q-Sepharose ™, HPLC System III) using a linear gradient of 0–10% aqueous HOAc over 60 minutes to yield (50%) of the hydrolyzed product 1-[2-(4-nitrophenyl)ethyl]-1,4,7,10-tetraazacyclododecane-4,7,10-triactic acid, and characterized by:

$^1$H NMR (D$_2$O) 8.22(d), 7.55(d), 3.60–3.90(m), 3.10–3.40(m).

EXAMPLE 21

Preparation of
1-[2-(4-aminophenyl)ethyl]-1,4,7,10-tetraazacyclododecane-4,7,10-triacetic acid; (EA-DO3A).

In a Parr-hydrogenater was placed 50 ml of an aqueous solution of 214 mg (0.43 mmole) of 1-[2-(4-nitrophenyl)ethyl]-1,4,7,10-tetraazacyclododecane-4,7,10-triacetic acid (prepared by the procedure of Example 20) and 40 mg of 10% Pd/C. The suspension was shaken until hydrogen uptake ceased. After filtration, the aqueous solution was freeze-dried yielding 197 mg (98%), as a tan solid, 1-[2-(4-aminophenyl)ethyl]-1,4,7,10-tetraazacyclododecane-4,7,10-triacetic acid, and characterized by:

$^1$H NMR (D$_2$O) 7.35(d), 7.20(d), 3.10–3.70(m);

$^{13}$C NMR (D$_2$O) 173.85, 172.50, 137.90, 131.90, 130.22, 121.55, 56.25, 55.14, 54.42, 50.12, 49.65, 49.31, 31.00.

EXAMPLE 22

Preparation of
1-(2-methoxy-5-nitrobenzyl)-1,4,7,10-tetraazacyclodo-
decane-4,7,10-triacetic acid, 4,7,10-trimethyl ester To a stirred acetonitrile solution (20 ml) containing 1.0 g of 1-(2-methoxy-5-nitrobenzyl)-1,4,7,10-tetraazacyclododecane (3 mmole) (prepared by the procedure of Example E) was added 1.6 g of methyl bromoacetate (11 mmole) in one portion. After one hour potassium carbonate (0.3 g) was added and stirring continued at room temperature for twelve hours. The reaction mixture was then filtered and the filtrate concentrated (in vacuo). The resulting residue was column chromatographed (silica, $CH_3CN/CH_3OH$, 9:1, V:V) yielding the triester as a white solid in 68 percent yield after concentration, and was further characterized by:

$^1H$ NMR ($CDCl_3$) 8.19(d), 8.14(s), 7.18(d), 2.58–3.99(m);

$^{13}C$ NMR ($CDCl_3$) 173.53, 172.83, 164.59, 142.28, 128.51, 127.69, 126.49, 112.30, 57.25, 56.90, 55.03, 54.21, 53.06, 52.09, 52.00, 51.54, 50.68, 50.30, 49.85, 49.63, 49.31, 49.00, 48.68, 48.37, 48.05, 47.70, 47.39.

EXAMPLE 23

Preparation of
1-(2-methoxy-5-nitrobenzyl)-1,4,7,10-tetraazacyclodo-
decane-4,7,10-triacetic acid A 6M hydrochloric acid solution (3 ml) containing 0.25 g of 1-(2-methoxy-5-nitrobenzyl)-1,4,7,10 -tetraazacyclododecane-4,7,10-triacetic acid, 4,7,10-trimethyl ester (0.45 mmole) (prepared by the procedure of Example 22) was stirred and heated at 100° C. for 24 hours. After cooling to room temperature, 5 ml of water was added and the aqueous solution freeze-dried to give a tan solid. Following column chromatography (silica, Solvent System 5) the triacid was isolated in 60 percent yield as an off-white solid, MP=228°–230° C. (dec), and further characterized by:

$^1H$ NMR ($D_2O$) 8.18(d), 8.09(s), 7.12(d), 3.87(s), 2.10–3.60(m);

$^{13}C$ NMR ($D_2O$) 180.45, 179.80, 163.66, 140.22, 128.60, 126.24, 122.66, 111.50, 59.91, 59.06, 56.44, 52.75, 50.92, 48.84.

EXAMPLE 24

Preparation of
1-(2-methoxy-5-aminobenzyl)-1,4,7,10-tetraazacyclodo-
decane-4,7,10-triacetic acid To a nitrogen purged aqueous (50 ml) solution containing 50 mg of $PtO_2$ was added 50 mg of 1-(2-methoxy-5-nitrobenzyl)-1,4,7,10-tetraazacyclododecane-4,7,10-triacetic acid (prepared by the procedure of Example 23). After hydrogenating in a Parr bomb for one hour, the solution was filtered and the aqueous filtrate freeze-dried to give the aniline derivative as a tan solid (95 percent yield), MP>240° C. dec, and further characterized by:

$^1H$ NMR ($D_2O$) 7.54(bs), 7.21(d), 7.09(d), 7.05(s), 6.88(s), 3.84(s), 3.78(s), 2.85–3.56(m);

$^{13}C$ NMR ($D_2O$) 180.59, 179.77, 153.38, 124.16, 124.03, 122.82, 120.18, 113.68, 112.43, 59.06, 57.02, 55.96, 53.67, 50.52, 50.08, 49.70, 49.04, 48.32.

EXAMPLE 25

Preparation of
1-(2-hydroxy-5-nitrobenzyl)-1,4,7,10-tetraazacyclodo-
decane-4,7,10-triacetic acid To an aqueous solution (1 ml) of 1-(2-hydroxy-5-nitrobenzyl-1,4,7,10-tetraazacyclododecane (200 mg, 0.62 mmole) (prepared by the procedure of Example F) was added bromoacetic acid (309 mg, 2.2 mmole, and NaOH (3.5 ml, ≈1M) with stirring at room temperature. The reaction progress was monitored by LC (anion exchange, Q-Sepharose TM) and the pH maintained at about 8 via the addition of NaOH as needed. After 12 hours the solution was freeze-dried and the solid residue chromatographed (column) on silica gel eluting with Solvent System 5. The major yellow fraction was concentrated, dissolved in $H_2O$ and freeze dried to give the desired product as a bright yellow powder (150 mg, 49 percent); MP=230°–235° C. (dec), and further characterized by:

$^{13}C$ NMR ($D_2O$) 166.41, 165.60, 160.00, 119.91, 116.02, 113.85, 111.71, 104.59, 45.20, 44.50, 43.96, 36.43.

EXAMPLE 26

Preparation of
1-(2-hydroxy-5-aminobenzyl)-1,4,7,10-tetraazacyclodo-
decane-4,7,10-triacetic acid To an argon purged, aqueous solution (25 ml) of N-(2-hydroxy-5-nitrobenzyl)-1,4,7,10-tetraazacyclododecane-4,7,10-triacetic acid (200 mg, 0.4 mmole) (prepared by the procedure of Example 25) was added $PtO_2$(130 mg) followed by the introduction of $H_2$ (Parr hydrogenator). After total disappearance of yellow color, the solution was purged with argon and filtered. The aqueous solution was then freeze-dried to give the product as a tan solid (146 mg, 78 percent).

EXAMPLE 27

Preparation of
α-[2-(4-nitrophenyl)ethyl]-1,4,7,10-tetraazacyclododec-
ane-1-(R,S)-acetic-4,7,10-tris-(R-methylacetic) acid,
1-isopropyl-4,7,10-trimethyl ester; (PN-DOTMA
trimethylisopropyl ester)

To a solution of 1.00 g (2.37 mmole) of α-[3-(4-nitrophenyl)propyl]-1,4,7,10-tetraazacyclododecane-1acetic acid, 1-methyl ester (prepared by the procedure of Example P) in 35 ml dry acetonitrile was added 1.15 g (8.32 mmoles) of anhydrous potassium carbonate with vigorous stirring under nitrogen. Optically active α-benzene sulfonate of lactic acid methyl ester (1.79 g, 7.36 mmoles S:R=98.2) was added and the mixture was stirred at room temperature for 60 hours. TLC analysis indicated formation of new products ($R_f$=0.71, Solvent System 2 for titled tetraesters and $R_f$=0.89 for triester). The resulting solution with suspended carbonate salts was poured into 40 ml of chloroform and the precipitated inorganic salts were filtered. Solvent was removed from this filtrate and the crude orange oil was chromatographed twice on a 1 in. × 16 in. flash silica gel column using Solvent System 2 as the eluent to afford the titled product as a nonresolved mixture of tetraester diastereomers (1.00 g, 1.47 mmole, 62% yield) which were free of underalkylated products.

$^1H$ NMR analysis of this material showed it to contain approximately 0.5 equivalents of unreacted benzene sulfonate derivative. The NMR spectra of this material were not coalescent at 60° C. in chloroform:

$^1$H NMR (CDCl$_3$, 60° C.) 7.9–8.1(m, 2H), 7.2–7.4(m, 2H), 5.06(m, 1H), 3.4–4.0(m, 9H), 1.7–3.4(m, 2OH), 1.0–1.7(m, 15H);

IR (CDCl$_3$) cm$^{-1}$ 2980, 2840, 1725, 1710 (ester carbonyl), 1590, 1510, 1440, 1340;

Fast atom bombardment mass spectrum, m/e 702 [M+Na$^+$]$^+$, 687.

EXAMPLE 28

Preparation of α-[2-(4-aminophenyl)ethyl]-1,4,7,10-[tetraazacyclododecane-1-(R,S)-acetic-4,7,10-tris-(R-methylacetic) acid, 1-isopropyl-4,7,10-trimethyl ester; (PA-DOTMA trimethylisopropyl ester)

α-[2-(4-nitrophenyl)ethyl]-1,4,7,10-tetraazacyclododecane-1-(R,S)-acetic-4,7,10-tris-(R-methylacetic) acid, 1-isopropyl-4,7,10-trimethyl ester (950 mg, 1.40 mmoles uncorrected) (prepared by the procedure of Example 27), which contained unreacted α-[3-(4-nitrophenyl)propyl]- 1,4,7,10-tetraazacyclododecane-1-acetic acid, 1-methyl ester, was dissolved in 10 ml of 30% aqueous methanol containing 1.00 g of 10% palladium on carbon catalyst under a nitrogen atmosphere. Excess hydrogen was purged through the solution for 7 hours. At this point, TLC inspection revealed formation of a strongly ninhydrin positive material ($R_f$=0.62 Solvent System 2, $R_f$=0.71 for starting material). The methanolic catalyst slurry was filtered through celite and evaporation of solvent provided 800 mg of the crude title product as a clear oil which contained benzene sulfonic acid ($R_f$=0.09 Solvent System 2) from the concomitant hydrogenolysis of the benzene sulfonate ester. The crude oil was chromatographed on a 1 in. × 8 in. flash silica gel column with 10% methanol in chloroform which eluted a light yellow band in the void volume. Solvent System 2 was then applied to elute the titled product (480 mg) in 52% yield as a mixture of unresolved diastereomers and geometric isomers. Three distinct ab quartets were observed in the aromatic region of the $^1$H NMR:

$^1$H NMR (CDCl$_3$, 30° C.) 6.63–8.0(m (quartets), 4H), 5.07(m, 1H, isopropyl methine H), 3.53–3.9(m, 13H with four singlets at 3.85, 3.73, 3.69 and 3.56), 3.46(m, 1H), 3.25(broad t, 3H), 2–3.1(m, 14H), 1.0–2.0(m, 15H);

$^{13}$C NMR (CDCl$_3$, 30° C.) 177.3, 177, 176.4, 176.2, 175.9, 174.3, 172.9, 170.6, 145.3, 144.9, 130.8, 129.7, 129.3, 129.1, 128.8, 128.4, 127.5, 126.3, 115.2, 115.1, 114.9, 69.0, 68.4, 67.3, 61.6, 57.8, 57.4, 56.7, 56.5, 56.4, 52.9, 52.7, 52.1, 50.8, 50.7, 50.6, 47.3, 47.1, 47.0, 46.9, 46.5, 46.3, 46.1, 44.8, 44.5, 44.3, 34.1, 32.9, 32.5, 32.2, 31.8, 24.8, 22.2, 22.1, 22.0, 21.8, 21.6, 15.8, 14.9, 7.7, 7.5, 7.4, 7.1;

IR (CDCl$_3$) cm$^{-1}$ 2960, 2840, 1720, 1510, 1450, 1375;

Fast atom bombardment mass spectrum, m/e 672 [M+Na$^+$]$^+$, 686.

EXAMPLE 29

Preparation of α-[2-(4-aminophenyl)ethyl]-1,4,7,10-tetraazacyclododecane-1-(R,S)-acetic-4,7,10-tris-(R-methylacetic) acid; (PA-DOTMA)

The diastereomeric mixture of α-[2-(4aminophenyl)ethyl]-1,4,7,10-tetraazacyclododecane-1-(R,S)-acetic-4,7,10-tris-(R-methylacetic) acid, 1-isopropyl-4,7,10-trimethyl ester (400 mg, 0.59 mmoles) (prepared by the procedure of Example 28) was dissolved in 50 ml of 6N concentrated hydrochloric acid and refluxed for 30 hours. TLC analysis (Solvent System 1) indicated conversion of ester ($R_f$=0.98 Solvent System 1) to two new spots ($R_f$=0.6, high diastereomer and $R_f$=0.54, low diastereomer Solvent System 1, both spots UV, ninhydrin, and iodine positive). Excess solvent was removed on a rotary evaporator and after drying, a mixture of crude diastereomers of the title product (403 mg) was obtained as the hydrochloride salt. Preparative separation of the two diastereomers of the title product was accomplished by applying 290 mg (0.51 mmole) of the crude salt to a 1×13 cm silica flash gel column which was eluted with Solvent System 8. The high $R_f$ diastereomer (119 mg, 0.21 mmole) was obtained in purer form than the low $R_f$ diastereomer (90 mg, 0.16 mmole) since high $R_f$ diastereomer eluted from the column first:

$^1$H NMR for high $R_f$ diastereomer:

$^1$H NMR (D$_2$O, 90° C. pD=7.5) 7.12(d, 2H), 6.80(d, 2H), 3.66(m, 1H), 3.57(broad t, 3H), 2–3.4(m, 19H), 1.89(m, 1H), 1.37(m, 1H), 1.15(d, 3H), 1.10(d, 3H), 1.06(d, 3H);

$^{13}$C NMR (D$_2$O, 90° pD=7.5) 184.4, 184.2, 184.0, 183.3, 135.9, 132.6, 131.7, 119.1, 78.2, 69.0, 61.7, 61.5, 61.1, 57.4, 54.1, 49.7, 49.6, 48.2, 47.7, 47.2, 34.8, 33.8, 9.6, 9.1, 9.0;

Fast atom bombardment mass spectrum, m/e 566 M+H$^+$]$^+$, 588 [M+Na$^+$]$^+$, 604 [M+K$^+$]$^+$, 626 [M+K$^+$+Na$^+$-H$^+$]$^+$, 642 [M+2K$^+$-H$^+$]$^+$.

Preparation of Final Products—Complexes

Metal ligand complexes were prepared by various methods as shown below. The methods included mixing of the metal and ligand in aqueous solution and adjusting the pH to the desired value. Complexation was done in solutions containing salts and/or buffers as well as water. Sometimes heated solutions were found to give higher complex yields than when the complexation was done at ambient temperatures. Also the work-up used in the synthesis of BFC has been shown to effect the complexation.

EXAMPLE 30

Preparation of α-(4-aminophenyl)-1,4,7,10-tetraazacyclododecane-1,4,7,10-tetraacetic acid, ammonium salt, samarium(III) complex; Sm(BA-DOTA)

A small sampler 53 mg, (0.094 mmole) of α-(4-aminophenyl)-1,4,7,10-tetraazacyclododecane-1,4,7,10-tetraacetic acid (prepared by the procedure of Example 3) was dissolved in 100 μl of water and treated with 3 ml of 0.043M Sm(OAc)$_3$ solution (48.8 mg, 0.128 mmole) at pH 6–7. This solution was heated at 100° C. and the degree of complexation was determined by anion exchange HPLC. When complexation was complete by anion exchange chromatography, HPLC System III, the solution of the complex was cooled to room temperature (about 25° C.) and freeze dried. The samarium complex was purified by silica gel chromatography (eluting with Solvent System 1). This procedure gave the title product in 82 percent yield. This complex was characterized by TLC, fast atom bombardment mass spectrometry, anion exchange HPLC, and futher characterized by:

1H (D$_2$O) 8.94, 7.81, 7.21, 6.97, 6.80, 5.63, 5.01, 4.58, 4.01, 3.56, 1.78, 1.53, 1.24, 1.10, 0.77, −2.80, −2.95, −3.21, −3.91;

$^{13}$C NMR (D$_2$O) 190.3, 184.9, 181.4, 146.8, 134.3, 122.7, 116.4, 80.8, 72.6, 64.2, 57.2, 55.8, 54.7, 53.4, 51.5, 49.7, 45.5, 43.5, 23.6.

Fast atom bombardment mass spectrum, [M+H$^+$]$^+$=645 (Sm isotope pattern).

EXAMPLE 31

Preparation of α-(4-aminophenyl)-1,4,7,10-tetraazacyclododecane-1,4,7,10-tetraacetic acid, samarium(III) complex A solution of 150 μl Sm-153 (3×10$^{-4}$M, in 0.1N HCl) and 600 μl SmCl$_3$ (3×10$^{-4}$M) in 0.1N HCl was prepared by adding the Sm-153 solution to the SmCl$_3$ solution. Then 5.0 μl of 2.0M NaOAc was added followed by 45 μl of 50 mM ligand (prepared by the procedure of Example 3) in HEPES buffer. The pH of the solution was adjusted to 7 with 275 μl of 0.5M HEPES. This solution was split into two fractions of 500 μls each, and one fraction was heated for 1 hour at 100° C.

The solutions were passed through SP-Sephadex ™ cation excange resin. The percent of metal as a complex was determined using the procedure previously described. The results showed 99.6% of the metal as a complex for the heated sample and 96.6% for the non-heated sample.

Stability of Chelates by pH Profile

The stability of metal ligand complexes was measured by subjecting them to various pH values and analyzing for complex in solution. At low pH, protonation of the ligand can cause the release of metal. At high pH, metal hydroxides compete with chelate formation. Thus, when looking for inert chelates, a desirable inert chelate will remain as a chelate when exposed to high and low pH values.

Profiles of the inertness at various pH values for some of the chelates of this invention were generated using the methods described in the following examples. In some cases non-chelated metal was removed by passing the solution through a cation exchange resin. Dilute sodium hydroxide and hydrochloric acid solutions were used to adjust the pH of the complex solutions from about 1 to about 14. The percent metal as a complex was then determined by the methods previously described.

In a similar manner, several bifunctional chelate conjugates were prepared and subjected to pH 2.8, 4.0 and 6.0. The amount of conjugate remaining in solution was determined by HPLC using a radiometric detector. The results are shown in Example XX in the biology section.

EXAMPLE 32 pH Stability of α-(4-aminophenyl)-1,4,7,10-tetraazacyclododecane-1,4,7,10-tetraacetic acid, samarium(III) complex The heated and non-heated samples from Example 30 were each split into 2×250 μl aliquots. One 250 μl aliquot was adjusted with HCl to give the pH's represented in the table following. The second 250 μl aliquot was adjusted with μl quantities of NaOH to the desired pH's. Once the desired pH was reached, a 25 μl aliquot was removed and the percent of metal as complex determined as previously described. The results are as follows:

| pH | % Complex Heated | % Complex Not heated |
|---|---|---|
| 1 | 98.9 | 92.7 |
| 3 | 99.6 | 93.3 |
| 5 | 99.6 | 92.9 |
| 7 | 99.6 | 95.7 |
| 9 | 99.9 | 95.8 |
| 11 | 99.6 | 95.7 |
| 13 | 99.6 | 94.5 |

This data shows the stability for this sample whether heated or not and regardless of the pH tested.

EXAMPLE 33

Preparation of α-(4-aminophenyl)-1,4,7,10-tetraazacyclododecane-1,4,7,10-tetraacetic acid, yttrium(III) complex Ten μl of a solution containing 1.4 mg/100 μl of α-(4-aminophenyl)-1,4,7,10-tetraazacyclododecane-1,4,7,10-tetraacetic acid (prepared by the procedure of Example 3) was added to 100 μl of Y(OAc)$_3$ (0.003M) spiked with Y-90. To this solution was added 500 μl of water followed by 125 μl of NaOAc (0.5M). Water (265 μl) was added to the solution to bring the total volume to 1 ml. This solution was divided into two aliquots. One aliquot was heated to 100° C. for 1 hour. Both heated and non-heated samples were tested to determine the percent of metal as a complex using the cation exchange procedure previously described. The results showed 84% and 4% of the metal as a complex for the heated sample and the non-heated sample, respectively.

EXAMPLE 34

Preparation of α-(4-aminophenyl)-1,4,7,10-tetraazacyclododecane-1,4,7,10-tetraacetic acid, lutetium(III) complex A solution of α-(4-aminophenyl)-1,4,7,10-tetraazacyclododecane-1,4,7,10-tetraacetic acid (prepared by the procedure of Example 3) was dissolved in distilled water to yield a concentration of 1.63 mg/ml.

A lutetium chloride solution was prepared by dissolving lutetium chloride in 0.1N HCl to result in a concentration of 3.9 mg/ml (0.01M). Lutetium-177 (0.3 mmolar) was used as a tracer.

A volume of 30 μl of 0.01M lutetium solution was added to 2 μl of Lu-177 solution. The appropriate amount of ligand from above was added and HEPES buffer (0.1M, pH=7.6) was added to give a total volume of 1.0 ml. The resultant solutions were 0.3 mmolar in ligand and lutetium. The solution was then heated to 100° C. for one hour and the percent of Lu as a complex determined to be 86% by the cation exchange method described previously.

EXAMPLE 35

Preparation of α-(4-isothiocyanatophenyl)-1,4,7,10-tetraazacyclododecane-1,4,7,10-tetraacetic acid, samarium(III) complex A sample, 7 mg, (10.8 μmole) of α-(4-aminophenyl)-1,4,7,10-tetraazacyclododecane-1,4,7,10-tetraacetic acid, samarium(III) complex (prepared by the procedure of Example 30) was dissolved in 400 μl water. Excess thiophosgene (50 μl) was added, followed by 400 μl CHCl$_3$ and the two-phase reaction stirred vigorously for 30 minutes. At the end of this time, the water layer was extracted with 500 μl CHCl$_3$ four times, and the water layer then was lyophilized to give the desired titled product in quantitative yield.

The UV showed this compound to have a band at 272 and 282 nm. The TLC, silica gel developed by 75:25 V:V CH$_3$CN:H$_2$O, gave R$_f$=0.38. The starting material has an R$_f$=0. 19. IR showed —SCN stretch at 2100 cm$^{-1}$; fast atom bombardment mass spectrum [M+H$^+$]$^+$=687.

EXAMPLE 36

Preparation of α-(4-aminophenyl)-1,4,7,10-tetraazacyclododecane-1,4,7,10-tetraacetic acid, ammonium salt, yttrium(III) complex A sample, 90 mg (160 mmole), of α-(4-aminophenyl)-1,4,7,10-tetraazacyclododecane-1,4,7,10-tetraacetic acid (prepared by the procedure of Example 3) was dissolved in 1 ml water. To this solution was added 3 ml of water containing 51 mg (192 mmole) of Y(OAc)$_3$. The reaction mixture, pH=6 to 7, was then heated at 100° C. for two hours. The resulting solution was then passed through glass wool and lyophilized to give 126 mg of yellow solid. The solid was chromatographed on silica gel (Solvent System 1) to yield 71 mg (76 percent) of the desired complex product. Analysis by anion exchange showed the same retention time as was found for the analogous Sm complex. The title product was characterized by:

$^{13}$C NMR (D$_2$O) 180.8, 180.5, 179.9, 146.1, 133.4, 122.0, 116.1, 74.9, 66.3, 56.3, 55.8,55.4, 55.1, 54.8, 52.2, 46.0, 44.0, 23.6;

$^1$H NMR (D$_2$O) 6.90(d), 6.70(d), 4.40(s), 3.45-3.06(m), 2.71-2.10(m), 1.75(s).

Fast atom bombardment mass spectrum, [M+H$^+$]$^+$=582.

EXAMPLE 37

Preparation of α-(4-isothiocyanatophenyl)-1,4,7,10-tetraazacyclododecane-1,4,7,10-tetraacetic acid, sodium salt, yttrium(III) complex A sample of the α-(4-aminophenyl)-1,4,7,10-tetraazacyclododecane-1,4,7,10-tetraacetic acid, yttrium complex (prepared by the procedure of Example 36) (10 mg, 17 μmole) was dissolved in 400 μl H$_2$O. To this solution was added 64 μl thiophosgene (excess) and 400 μl CHCl$_3$ and the resulting mixture stirred vigorously for 40 minutes. During this time several small additions of solid NaHCO$_3$ were made to keep the pH at about 8. At the end of the reaction, the water layer was separated and extracted with 1 ml of CHCl$_3$, four times, and lyophilized. The title product was characterized by TLC and UV spectroscopy.

EXAMPLE 38

Preparation of α-[2-(4-aminophenyl)ethyl]-1,4,7,10-tetraazacyclododecane-1,4,7,10-tetraacetic acid, yttrium(III) complex, ammonium salt; NH$_4$[Y(PA-DOTA)]

The ligand, α-[2-(4-aminophenyl)ethyl]-1,4,7,10-tetraazacyclododecane-1,4,7,10-tetraacetic acid (prepared by the procedure of Example 8) was converted to the mixed protonated-ammonium salt by chromatography on a strong cation exchange resin (SP-Sephadex ™ C-25, Pharmacia). The column was in the protonated form and washed with distilled water. A concentrated aqueous solution of the ligand was applied to the column, followed by washing the column with distilled water. The ligand was eluted from the column with 0.5M NH$_4$OH. The eluent was reduced to dryness.

A solution of Y(OAc)$_3$.4H$_2$O (0.0728 g, 0.215 mmole) in 5 ml of distilled water was added to a warm solution of the mixed protonated-ammonium salt ligand (0.120 g, 0.215 mmole) in 5 ml of water. The solution was brought to reflux and the pH adjusted to about 7.0 with 0.1M NH$_4$OH. After 1 hour at reflux, the solution was cooled and reduced to dryness. Excess NH$_4$OAc was removed by heating the white solid in an oil bath at about 105° C. under vacuum. The title product (which contained about one equivalent of ammonium acetate) yield was 0.142 g (94 percent) and was characterized by:

$^{13}$C NMR (D$_2$O, 88° C., 75 MHz) 23.8, 27.6, 35.4, 49.6, 55.0, 56.2, 56.9, 57.1, 65.7, 68.0, 121.7, 132.6, 138.8, 180.7, 181.4, 182.0, 183.1;

Fast atom bombardment mass spectrum, m/e 610 (positive ion, [M$^-$+2H$^+$]$^+$), 608 (negative ion, M$^-$).

EXAMPLE 39

Preparation of (1-[2-(4-aminophenyl)ethyl]-1,4,7,10-tetraazacyclododecane-1,4,7,10-tetraacetic acid, samarium(III) complex, ammonium salt; NH$_4$[Sm(PA-DOTA)]

When the procedure of Example 38 was repeated, using Sm(OAc)$_3$.3H$_2$O (0.082 g, 0.215 mmole) in place of Y(OAc)$_3$.4H$_2$O, the title product (which contained about one equivalent of ammonium acetate) was prepared in a yield of 0. 155 g (94 percent) and was characterized by:

$^{13}$C NMR (D$_2$O, 88° C. 75 MHz) 23.5, 27.2, 35.6, 50.5, 54.5, 56.0, 57.2, 57.9, 69.5, 71.5, 122.3, 133.0, 139.7, 181.2, 188.4, 189.3, 190.9;

Fast atom bombardment mass spectrum, m/e 673 (positive ion, [M$^-$+2H$^+$]$^+$, Sm isotope pattern), m/e 671 (negative ion, M$^-$, Sm isotope pattern).

EXAMPLE 40

Preparation of α-[2-(4-isothiocyanatophenyl)ethyl]-1,4,7,10-tetraazacyclododecane-1,4,7,10-tetraacetic acid, samarium(III) complex, ammonium salt; NH$_4$[Sm(SCN-PA-DOTA)]

Solutions of Sm(OAc)$_3$.3H$_2$O (27.9 mg, 381.56 g/mole, 73.1 μmole) in 10 ml of distilled water and 42 mg of PA-DOTA, mixed ammonium-potassium salt (632.97 g/mole, 66.4 μmole) (prepared by the procedure of Example 8) in 10 ml of distilled water were mixed and heated on a steam bath. After 30 min., the reaction to form [Sm(PA-DOTA)] was complete as determined by HPLC using the method described in Example 41. The solution was reacted with a solution of 45.4 mg of CSCl$_2$ (114.98 g/mole, 395 μmole) in 20 ml of chloroform by shaking in a separatory funnel. The reaction was complete after about one min. as determined by HPLC and by the absence of a positive test with ninhydrin (0.2% in ethanol) when the aqueous solution was spotted on a silica gel TLC plate (the starting chelate, [Sm(PA-DOTA)], tested positive). The chloroform layer was removed and the aqueous layer was washed with two 20 ml portions of chloroform. The aqueous layer was reduced to dryness by the addition of 100 ml of acetonitrile and evaporated at ambient temperature under a stream of nitrogen to yield 56 mg of the title product.

Fast atom bombardment mass spectrum, m/e 715 (positive ion, [M⁻+2H⁺]⁺, Sm isotope pattern), m/e 713 (negative ion, M⁻, Sm isotope pattern).

EXAMPLE 41

HPLC Analysis of the rate of chelation of $Y^{3+}$ with PA-DOTA

The rate of PA-DOTA chelation with $Y^{3+}$ was studied as a function of the work-up used in the synthesis of PA-DOTA. The extent of chelation was monitored by HPLC using an Alltech Econosphere ™ C18 100 mm column. The gradient used was: A) 95:5 of pH 6.0, 0.05M NaOAc buffer:CH₃CN, B) 30:70 of pH 6.0, 0.05M NaOAc buffer:CH₃CN, A to B in 15 min. A solution of PA-DOTA, hydrochloride salt, (retention time=1.31 min) and of PA-DOTA mixed ammonium-potassium salt (retention time=4.55 min), both prepared by the procedure of Example 8, were prepared as 1.6 mM, pH 6.0 0.5M NaOAc buffer. One ml (1.6 μmole) of each of the two solutions was reacted with 0.2 ml (8 μmole) of Y(OAc)₃.4H₂O solution (40 mM in pH 6.0 0.5M NaOAc buffer). Chelate formation was determined by the appearance of a peak at a retention time=3.96 min (confirmed by comparison to a sample from Example 38). Chelate formation results were as follows.

| PA—DOTA Salt | % Complex | Time(min)/Temp. |
| --- | --- | --- |
| PA—DOTA, HCl salt | >90 | <1/room temp. |
| PA—DOTA mixed ammonium-potassium salt | <10 >85 | 15/room temp. 10/90° C. |

Clearly, the method of purification of the BFC has an effect on the rate of chelation.

EXAMPLE 42

Preparation of α-[2-(4-aminophenyl)ethyl]-1,4,7,10-tetraazacyclododecane-1-(R,S)-acetic-4,7,10-tris(methylacetic) acid, samarium(III) complex, ammonium salt; NH₄[Sm(PA-DOTMA)]

A solution of Sm(OAc)₃.3H₂O (13.2 mg in 2 ml of distilled water) was added to a solution of α-[2-(4-aminophenyl)ethyl]-1,4,7,10-tetraazacyclododecane-1-(R,S)-acetic-4,7,10-tris-(methylacetic) acid (30 mg in 2 ml of distilled water), (prepared by the procedure of Example 29, high $R_f$ diastereomer). The pH 6.5 solution was heated on a steam bath and the reaction was monitored by HPLC. After 30 min. of heating the solution was reduced to dryness on a rotary evaporator and dried in a vacuum oven.

Fast atom bombardment mass spectrum, m/e 715 (positive ion, [M+2H⁺]⁺, Sm isotope pattern), 737 (positive ion, [M+H⁺+Na⁺]⁺, Sm isotope pattern) 713 (negative ion, (M⁻), Sm isotope pattern).

In the following examples the complex solutions were passed through an ion exchange column to remove any excess free metal from solution. Labile systems would return to equilibrium and similiar amounts of the free metal would be in solution. Inert systems would not reequilibrate and the amount of non-chelated metal should decrease. Thus even though a complex can be formed in low yield, a purification by passing it through an ion exchange resin could result in a usable stable complex without uncomplexed metal.

EXAMPLE 43

Preparation of α-(2-methoxy-5-aminophenyl)-1,4,7,10-tetraazacyclododecane-1,4,7,10-tetraacetic acid, samarium(III) complex A $3 \times 10^{-2}$M solution of α-(2-methoxy-5-aminophenyl)-1,4,7,10-tetraazacyclododecane-1,4,7,10-tetraacetic acid (prepared by the procedure of Example 12) was prepared by dissolving 5.8 mg in 325 μl NANOpure ™ water. A 10 μl aliquot of this solution was added to 990 μl of $3 \times 10^{-4}$M SmCl₃ (in 0.1N HCl) spiked with Sm-153. The pH was then brought to 7.0 with NaOH. This solution was split into two fractions of 500 μl each, and one fraction was heated for 1 hour at 100° C. Both heated and non-heated samples were tested to determine the percent of metal as a complex by the cation exchange method described previously. The solution was then passed through SP-Sephadex ™ resin. Complexation was again determined as the purified samples. The results are shown in the following table.

| | Heated | | Non-Heated | |
| --- | --- | --- | --- | --- |
| | Purified | Not Purified | Purified | Not Purified |
| % Complex | 96 | 95 | 97 | 89 |

EXAMPLE 44 pH Stability of α-(2-methoxy-5-aminophenyl)-1,4,7,10-tetraazacyclododecane-1,4,7,10-tetraacetic acid, samarium(III) complex The heated and non-heated purified samples from Example 43 were each split into 2×250 μl aliquots. One aliquot was adjusted with HCl and the other with NaOH to give the pH's represented in the table following. After the desired pH was reached the sample was allowed to stand for 10 min and the amount of metal as a complex was determined by the cation exchange method described previously. The results are shown in the following table.

| | % Complex | |
| --- | --- | --- |
| pH | Heated | Not heated |
| 2 | 95 | 94 |
| 3 | 97 | 95 |
| 5 | 98 | 97 |
| 7 | 96 | 97 |
| 9 | 98 | 96 |
| 11 | 97 | 98 |
| 13 | 100 | 99 |

EXAMPLE 45

Preparation of α-(2-methoxy-5-nitrophenyl)-1,4,7,10-tetraazacyclododecane-1,4,7,10-tetraacetic acid, samarium(III) complex A $3 \times 10^{-2}$M solution of α-(2-methoxy-5-nitrophenyl)-1,4,7,10-tetraazacyclododecane-1,4,7,10-tetraacetic acid (prepared by the procedure of Example 11) was prepared by dissolving 7.9 mg in 464 μl NANOpure ™ water. A 10 μl aliquot of this solution was added to 950 of $3 \times 10^{-4}$M SmCl₃ (in 0.1N HCl) spiked with Sm-153. The pH was then brought to 7.0 with NaOH. This solution was split into two fractions of 500 μl each;

and one fraction was heated for 1 hour at 100° C. Both heated and non-heated samples were tested to determine the percent of metal as a complex using the cation exchange method described previously. The solutions were passed through SP-Sephadex ™ resin. Complexation was then determined on the purified samples using the general procedure described hereinbefore. The results are shown in the following table.

|  | Heated | | Non-Heated | |
| --- | --- | --- | --- | --- |
|  | Purified | Not Purified | Purified | Not Purified |
| % Complex | 100 | 72 | 100 | 46 |

EXAMPLE 46 pH Stability of α-(2-methoxy-5-nitrophenyl)-1,4,7,10-tetraazacyclododecane-1,4,7,10-tetraacetic acid, Sm(III) complex The heated and non-heated purified sample from Example 45 were each divided into two aliquots. One aliquot was adjusted with dilute HCl and the other with NaOH to give the pH's represented in the table following. After the desired pH was reached the sample was allowed to stand for 10 min and the amount of metal as a complex was determined by the cation exchange method described previously. The results are shown in the following table:

|  | Purified | |
| --- | --- | --- |
| pH | Heat | No heat |
| 2 | 99 | 99 |
| 4 | 100 | 100 |
| 5 | 100 | 100 |
| 7 | 100 | 100 |
| 9 | 100 | 100 |
| 11 | 100 | 100 |
| 13 | 100 | 100 |

EXAMPLE 47

Preparation of α-(4-nitrophenyl)-1,4,7,10-tetraazacyclododecane-1,4,7-triacetic acid, samarium(III) complex A 0.0219M (100 μl, 2.195 mmole) solution of α-(4-nitrophenyl)-1,4,7,10-tetraazacyclododecane-1,4,7-triacetic acid (prepared by the procedure of Example 4) was contacted with a 0.043M (25 μl, 1.075 mmole) solution of Sm(OAc)$_3$. The reaction mixture was subjected to anion exchange HPLC (Q-Sepharose ™ column, 1 cm×25 cm, flow rate=2 ml/min, eluted with 0–1M NH$_4$OAc gradient over 30 min). After one hour, the complex (retention time=11.1 min) had formed in 77 percent yield (area percent) and was completely resolved from the ligand peak (retention time=15.5 min). Additional evidence that the title complex had formed was obtained on silica gel TLC (Solvent System 4) whereby the ligand has an R$_f$=0. 59 and the complex has an R$_f$=0.00.

EXAMPLE 48

Preparation of α-(4-aminophenyl)-1,4,7,10-tetraazacyclododecane-1,4,7-triacetic acid, samarium(III) complex and α-(4-aminophenyl)-1,4,7,10-tetraazacyclododecane-1,4,10-triacetic acid, samarium(III) complex A solution, 0.022M (100 μl, 2.2 μmole), of the isomers (prepared by the procedure of Example 5) was contacted with a 0.043M (6.4 μl, 0,275 μmole) solution of Sm(OAc)$_3$. The reaction mixture was subjected to anion exchange HPLC (Q-Sepharose ™ column, 1 cm×25 cm, flow rate=2 ml/min, eluted with 0–0.25M NH$_4$OAC gradient over 30 min). After forty minutes, the complex (retention time=9.0 min) had formed in 66 percent yield (area percent) and was completely resolve d from the ligand peak (retention time=18.5 min ).

EXAMPLE 49

Preparation of α-(4-aminophenyl)-1,4,7,10-tetraazacyclododecane-1,4,7-triacetic acid, samarium-153 complex and α-(4-aminophenyl)-1,4,7,10-tetraazacyclododecane-1,4,10-triacetic acid, samarium-153 complex A 3×10$^{-2}$M solution of α-(4-aminophenyl)-1,4,7,10-tetraazacyclododecane-1,4,7-triacetic acid pentahydrochloride and α-(4-aminophenyl)-1,4,7,10-tetraazacyclododecane-1,4,10-triacetic acid pentachloride (prepared by the procedure of Example 5) was prepared by dissolving 4.2 mg in 300 μl NANOpure ™ water. A 10 μl aliquot of this solution was added to 15 μl of 2×10$^{-2}$M SmCl$_3$ (in 0.1N HCl) spiked with Sm-153. The volume was brought to 1 ml by addition of water. The pH was then brought to 7.0 with NaOH. This solution was split into two fractions of 500 μl each, and one fraction was heated for 1 hour at 100° C.

Both heated and non-heated samples were tested to determine the percent of metal as a complex by the cation exchange method described previously. The results showed 89% and 96% of the metal as a complex for the heated and non-heated samples, respectively.

EXAMPLE 50 pH Stability of α-(4-aminophenyl)-1,4,7,10-tetraazacyclododecane-1,4,7-triacetic acid, samarium(III) complex, and α-(4-aminophenyl)-1,4,7,10-tetraazacyclododecane-1,4,10-triacetic acid, samarium(III) complex The heated sample from Example 49 and the non-heated sample were each divided into 2 aliquots. One aliquot was adjusted with HCl and the other with NaOH to give the pH's represented in the table following. Once the desired pH was reached, the samples were allowed to stand for 10 minutes and the percent of metal as complex was determined by the cation exchange method described previously. The results are shown in the following table:

|  | % Complex | |
| --- | --- | --- |
| pH | Heated | Not heated |
| 1 | 86 | 83 |
| 3 | 99 | 99 |
| 5 | 99 | 99 |
| 7 | 89 | 96 |
| 9 | 99 | 98 |
| 11 | 96 | 89 |

-continued

| pH | % Complex | |
|---|---|---|
| | Heated | Not heated |
| 13 | 97 | 97 |

EXAMPLE 51

Preparation of
α-(4-nitrophenyl)-1,4,7,10-tetraazacyclododecane-1,4,7-triacetic acid, samarium(III) complex Thirteen microliters of $2\times10^{-2}$M solution of α-(4-nitrophenyl)-1,4,7,10-tetraazacyclododecane-1,4,7-triacetic acid (prepared by the procedure of Example 4) 15 μl of SmCl$_3$ (0.02M 0.1N HCl) and 2 μl of Sm-153, had the volume brought to 1 ml with NANOpure TM water. The pH was adjusted to 7.0 with NaOH. This solution was split into two fractions of 500 μl each, and one fraction was heated for 1 hour at 100° C. Both heated and non-heated samples were tested to determine the percent of metal as a complex using the cation exchange procedure described previously. The results showed 74% and 42% of the metal as a complex for the heated and non-heated samples, respectively.

EXAMPLE 52 pH Stability of
α-(4-nitrophenyl)-1,4,7,10-tetraazacyclododecane-1,4,7-triacetic acid, samarium(III) complex The heated sample of Example 51 was divided into 2 aliquots. One aliquot was adjusted with HCl and the other with NaOH to give the pH values represented in the following table. After the desired pH was reached the sample was allowed to stand for 10 minutes and the amount of metal as a complex was determined by the cation exchange method described previously. The results are shown in the following table.

| pH | % Complex |
|---|---|
| 1 | 67 |
| 2 | 70 |
| 4 | 70 |
| 5 | 72 |
| 7 | 74 |
| 9 | 76 |
| 10 | 76 |
| 12 | 75 |
| 13 | 76 |

EXAMPLE 53

Preparation of
1-[2-(4-aminophenyl)ethyl]-1,4,7,10-tetraazacyclododecane-4,7,10-triacetic acid, lutetium(III) complex A solution of EA-DO3A (prepared by the procedure of Example 17) was made by dissolving the solid in water. The final concentration was 0.01M.

A lutetium chloride solution was prepared by dissolving lutetium chloride in 0.1N HCl. The resultant concentration was 3.9 mg/ml of lutetium chloride (0.01M Lu). Lutetium-177 was used as the tracer.

A volume of 30 μl of 0.01M Lu solution was added to 2 μl of Lu-177 solution. A volume of 30 μl of ligand was added and HEPES buffer (0.1M, pH=7.6) was added to give a total volume of 1.0 ml. The resultant solution was 0.3 mM in ligand and lutetium.

The amount of Lu as a complex was determined to be 98 percent by the cation exchange method previously described.

EXAMPLE 54

Preparation of
1-[2-(4-aminophenyl)ethyl]-1,4,7,10-tetraazacylcododecane-4,7,10-triacetic acid, yttrium (III) complex; [Y(EA-DO3A)]

The ligand, 1-[2-(4-aminophenyl)ethyl]-1,4,7,10-tetraazacyclododecane-4,7,10-triacetic acid (prepared by the procedure of Example 17) was converted to the mixed protonated-ammonium salt by chromatography on a strong cation exchange resin (SP-Sephadex TM C-25, Pharmacia). The column was in the protonated form and washed with distilled water. A concentrated aqueous solution of the ligand was applied to the column, followed by washing the column with distilled water. The ligand was eluted from the column with 0.5M NH$_4$OH. The eluate was reduced to dryness on a rotary evaporator and dried in a vacuum oven.

A solution of Y(OAc)$_3$.4H$_2$O (0.203 g, 338.101 g/mole, 0.600 mmole) in 10 ml of distilled water was added to a warm solution of the mixed protonated-ammonium salt ligand (0.300 g, 499.615 g/mole, 0.600 mmole) in 10 ml of distilled water. The solution was brought to reflux and the pH was adjusted to about 7.0 with 0.1M NH$_4$OH. After 15 minutes at reflux, the solution was cooled and reduced to dryness on a rotary evaporator. Excess ammonium acetate was removed by heating the white solid in an oil bath at about 105° C. under vacuum. The title product (which contained about one equivalent of ammonium acetate) was provided in a yield of 373 mg (99 percent) and was characterized by:

$^{13}$C NMR (88° C., D$_2$O, 75 MHz) 24.4, 28.4, 51.2, 56.5, 57.2 (2C), 57.7, 67.2, 67.6, 120.5, 132.3, 135.2, 182.1,182.5, 183.0;

Fast atom bombardment mass spectrum, m/e 552 (positive ion, [M+H$^+$]$^+$), m/e 610 (negative ion, [M+OAc$^-$]$^-$).

EXAMPLE 55

Preparation of
1-[2-(4-aminophenyl)ethyl]-1,4,7,10-tetraazacyclodo-decane-4,7,10-triacetic acid, samarium complex; [Sm(EA-DO3A)]

When the procedure of Example 54 was repeated, using Sm(OAc)$_3$.3H$_2$O (0.229 g, 381.531 g/mole, 0.600 mmole) in place of the Y(OAc)$_3$.4H$_2$O, the title product (which contained about one equivalent of ammonium acetate) was prepared in a yield of 408 mg (99 percent) and was characterized by:

$^{13}$C NMR (88° C. D$_2$O 75 MHz) 23.8, 27.9, 51.4, 57.5, 58.1 (3C), 68.7. 73.4, 120.3, 132.2, 134.7, 185.0, 186.8, 192.1;

Fast atom bombardment mass spectrum, m/e 615 (positive ion [M+H$^+$]$^+$, Sm isotope pattern), m/e 673 (negative ion, [M+OAc$^-$]$^-$, Sm isotope pattern).

EXAMPLE 56

Preparation of
1-[2-(4-nitrophenyl)ethyl]-1,4,7,10-tetraazacyclododecane-4,7,10-triacetic acid, samarium(III) complex Ten microliters of 1.48 mg/100 μl (0.03M) solution of 1-[2-(4-nitrophenyl)ethyl]-1,4,7,10-tetraazacyclododecane-4,7,10-tetraacetic acid (prepared by the procedure of Example 20) was added to 15 μl of SmCl₃ solution (0.02M in 0.1N HCl) and spiked with Sm-153. The volume was brought to 1 ml with NANOpure ™ water. This solution was divided into two 500 μl fractions, and one fraction was heated for 1 hour at 100° C. Both heated and non-heated samples were tested to determine the percent of metal as a complex using the cation exchange procedure described hereinbefore. The results showed 81% and 43% of the metal as a complex for the heated and non-heated samples, respectively.

EXAMPLE 57 pH Stability 1-[2-(4-nitrophenyl)ethyl]-1,4,7,10-tetraazacyclododecane-4,7,10-triacetic acid, samarium(III) complex The heated sample of Example 56 was divided into two aliquots. One aliquot was adjusted with HCl and the other with NaOH to give the pH's represented in the following table. After the desired pH was reached the sample was allowed to stand for 10 min and the amount of metal as a complex was determined by the cation exchange method described previously. The results are shown in the following table.

| pH | % Complex |
|----|-----------|
| 1  | 20 |
| 2  | 37 |
| 4  | 49 |
| 5  | 58 |
| 7  | 81 |
| 9  | 62 |
| 10 | 64 |
| 12 | 64 |
| 13 | 54 |

EXAMPLE 58

Preparation of 1-[2-(4-aminophenyl)ethyl]-1,4,7,10-tetraazacyclododecane-4,7,10-triacetic acid, samarium(III) complex Three μl of 4.65 mg/100 ml solution of 1-[2-(4-aminophenyl)ethyl]-1,4,7,10-tetraazacyclododecane-4,7,10-triacetic acid (prepared by the procedure of Example 20) was added to a solution of 15 μl of SmCl₃ (0.02M in 0.1N HCl) previously spiked with Sm-153. The volume was brought to 1 ml with NANOpure ™ water. The pH of the solution was adjusted to 7.3 using NaOH. The solution was divided into two aliquots, and one aliquot was heated at 100° C. for 1 hour. Both heated and non-heated samples were tested to determine the percent of metal as a complex by the cation exchange method described previously. The results showed 96% and 93% of the metal as a complex for the heated and non-heated samples, respectivly.

EXAMPLE 59 pH Stability of 1-[2-(4-aminophenyl)ethyl]-1,4,7,10-tetraazacyclododecane-4,7,10-triacetic acid, samarium (III) complex The heated and non-heated samples of Example 58 were each divided into two aliquots. One aliquot of each sample was adjusted with HCl and the other with NaOH to give the pH's shown in the following table. After the desired pH was reached, the sample was allowed to stand for 10 minutes and the amount of metal as a complex was determined by the cation exchange method described previously. The results are shown in the following table.

| pH | % Complex Heated | Not Heated |
|----|------------------|------------|
| 1  | 44 | 13 |
| 3  | 50 | 42 |
| 5  | 73 | 55 |
| 7  | 96 | 93 |
| 9  | 98 | 98 |
| 11 | 89 | 90 |
| 13 | 28 | 37 |

EXAMPLE 60

Preparation of 1-(2-hydroxy-5-nitrobenzyl)-1,4,7,10-tetraazacyclododecane-4,7,10-triacetic acid, samarium(III) complex A $3 \times 10^{-2}$M solution of 1-(2-methoxy-5-nitrobenzyl)-1,4,7,10-tetraazacyclododecane-4,7,10-triacetic acid (prepared by the procedure of Example 25) was prepared by dissolving 3.9 mg in 260 μl NANOpure ™ water. A 10 μl aliquot of this solution was added to 15 l of $2 \times 10^{-2}$M SmCl₃ (in H₂O) spiked with 10 μl of Sm-153 in 0.1N HCl ($3 \times 10^{-4}$M). The volume was brought to one milliliter by addition of 965 μl DI H₂O. The pH was then brought to 7.0 with NaOH. This solution was split into two fractions of 500 μl each, and one fraction was heated for 1 hour at 100° C. Both heated and non-heated samples were tested to determine the percent of metal as a complex by the previously described cation exchange method. The results showed 71 percent and 74 percent of the metal as a complex for the heated and non-heated samples, respectively.

EXAMPLE 61 pH Stability of 1-(2-hydroxy-5-nitrobenzyl)-1,4,7,10-tetraazacyclododecane-4,7,10-triacetic acid, samarium(III) complex The heated and non-heated sample of Example 60 were each split into two 250 μl aliquots. One aliquot was adjusted with HCl and the other with NaOH to give the pH's represented in the table following. After the desired pH was reached the sample was allowed to stand for 10 minutes and the amount of metal as a complex was determined by the cation exchange method described previously. The results are shown in the following table.

| pH | % Complex Heated | Not heated |
|----|------------------|------------|
| 1  | 65  | 51 |
| 3  | 98  | 93 |
| 5  | 99  | 99 |
| 7  | 100 | 100 |
| 9  | 100 | 99 |
| 11 | 100 | 96 |
| 13 | 100 | 98 |

EXAMPLE 62

Preparation of 1-(2-hydroxy-5-aminobenzyl)-1,4,7,10-tetraazacyclododecane-4,7,10-triacetic acid, samarium(III) complex A $3 \times 10^{-2}$M solution of 1-(2-hydroxy-5-aminobenzyl)-1,4,7,10-tetraazacyclododecane-4,7,10-triacetic acid (prepared by the procedure of Example 26) was prepared by dissolving 3.2 mg in 100 μl NANOpure ™ water. A 10 μl aliquot of this solution (diluted to 20 μl) was added to 15 μl of $2\times10^{-2}$M SmCl$_3$ (in H$_2$O) spiked with Sm-153. The volume was brought to 1 ml by addition of 950 μl DI H$_2$O and 20 μl 0.1N NaOH. This solution was split into two fractions of 500 μl each, and one fraction was heated for 1 hour at 100° C. Both heated and non-heated samples, were tested to determine the percent of metal as a complex by the cation exchange method described previously. When less than 95 percent of the metal was complexed, the solution was passed through SP-Sephadex ™ resin. The percent of metal as a complex was again determined. The results are shown in the following table.

|  | Heated | | Non-Heated | |
| --- | --- | --- | --- | --- |
|  | Purified | Not Purified | Purified | Not Purified |
| % Complex | 99 | 68 | 99 | 21 |

EXAMPLE 63 pH Stability of 1-(2-hydroxy-5-aminobenzyl)-1,4,7,10-tetraazacyclododecane-4,7,10-triacetic acid, samarium(III) complex The heated and non-heated purified chromatographed samples from Example 62 were each split into two 250 μl aliquots. One 250 μl aliquot was adjusted with HCl and the other with NaOH to give the pH's represented in the table following. Once the desired pH was reached, samples were allowed to stand for 10 minutes and the percent of metal as complex was determined by the cation exchange method described previously. The results are as shown in the following table:

|  | % Complex | |
| --- | --- | --- |
| pH | Heated | Not heated |
| 1 | 60 | 56 |
| 2 | 74 | 76 |
| 3 | 84 | 87 |
| 5 | 97 | 98 |
| 7 | 99 | 99 |
| 9 | 99 | 98 |
| 11 | 99 | 99 |
| 13 | 99 | 99 |

Methods of Use-Biology

Bifunctional chelants having within the same molecule a metal chelating group such as DTPA and a reactive linker (the aryl amine) are known to be capable of being covalently attached to various target directed biomolecules having specificity for cancer or tumor cell epitopes or antigens. Radionuclide complexes of such conjugates are useful in diagnostic and/or therapeutic applications as means of conveying the radionuclide to a cancer or tumor cell. [Reference, Meares et al., Anal. Biochem. 142., 68–78 (1984)3 see also discussion on pp. 215–216 of J. Protein Chem., 3(2) (1984) by Meares and Goodwin, more recent references are Meares, U.S. Pat. No. 4,678,677, issued Jul. 7, 1987, Warshawsky et al. U.S. Pat. No. 4,652,519, issued Mar. 24, 1987 and Brechbiel, et al., Inorg. Chem., 25, 2772–2781 (1986)]. Conceivably, the product, employing radioactive or luminescent metals, may also be used for in vitro immunoassays.

Background Information

The utility of the labeled antibodies depends on a number of factors, for example: 1) the specificity of the antibody, 2) the inertness or stability of the complex under use conditions (i.e., serum stability), and 3) the integrity of the antibody, i.e. the specificity and the immunoreactivity of the antibody, is not affected by the labeling process.

Stability or inertness of the complex is of utmost importance to the effectiveness of the radionuclide-antibody conjugate as a diagnostic and/or therapeutic agent. Kinetic lability can lead to instability, e.g. in the serum, and the dissociation of the radionuclide from the complex. Thus it diminishes the diagnostic and therapeutic effectiveness. In addition, it poses a greater potential for general radiation damage to normal tissue. [Cole, et al., J. Nucl. Med., 28, 83–90 (1987)].

Linking of Radionuclide to Antibody

Attachment of radionuclide to antibody can be carried out by either linking the BFC to the antibody via procedures well known in the art, followed by chelation of the radionuclide under conditions compatible with the antibody, or alternatively, conjugation of the antibody to preformed (ambient or elevated temperature) metal - BFC complex. [Meares et al., Acc. Chem. Res. 17, 202–209 (1984)]. Examples are provided.

EXAMPLE ZA (COMPARATIVE)

Conjugation of 1-(4-isothiocyanatobenzyl)diethylenetriaminepentaacetic acid, samarium-153 complex to IgG and F(ab')$_2$ of CC-49; [$^{153}$Sm(SCN-Bz-DTPA)]-IgG and [$^{153}$Sm(SCN-Bz-DTPA)]-F(ab')$_2$ fragment.

The 1-(4-isothiocyanotobenzyl)diethylenetriaminepentaacetic acid, samarium-153 complex [$^{153}$Sm(SCN-Bz-DTPA)] was prepared by mixing 150 μl $^{153}$Sm in 0.1N HCl with 9 μl of 1-(4-isothiocyanatobenzyl)diethylenetriaminepentaacetic acid to which was added HEPES buffer (0.5M, pH 8.9, approximately 30 μl) to bring the pH to about 6. To conjugate, $22.5\times10^{-9}$ moles of IgG or F(ab')$_2$ of CC-49 (about $1\times10^{-4}$M concentration of protein in 50 mmole HEPES, pH 8.5) was mixed with the $^{153}$Sm complex, and the pH was adjusted to 8.9 by addition of a sodium carbonate solution (1.0M, 12–15 μl). Conjugation was carried out at room temperature (about 25° C.) for about 3 hours. The $^{153}$Sm complex labeled IgG or F(ab')$_2$ was isolated and characterized similarly as described in Example XII.

Experimental for Biology

EXAMPLES I, & II AND COMPARATIVE EXAMPLES A–D

In Vivo Screening of Bifunctional Chelates

The stability of certain rare earth chelates has been examined by in vivo testing in animals. For example, Rosoff, et al. in the International Journal of Applied Radiation and Isotopes 14, 129–135 (1963) report on the distribution of radioactive rare earth chelates in mice for certain aminocarboxylic acids. It was found that in vivo "the competition between the chelating agent and body constituents (inorganic and organic) for the rare-earth ions, determines its deposition and excretion." The strong rare-earth chelates of this invention are believed to dissociate very little and be excreted, while the weak and intermediate strength chelates known in the art dissociate more readily and thus are deposited in organs such as the liver. However, concentration of radionuclide in the liver is not always due to weak complex formation, but in some cases is due to the affinity that the metal chelate has for the liver. Chelates have, in fact, been prepared and utilized for the evaluation of liver function [Fritzberg, Alan R., *Radiopharmaceuticals: Progress and Clinical Perspectives*, Vol. 1, 1986; U.S. Pat. Nos. 4,088,747 and 4,091,088].

The biodistribution of the yttrium and samarium chelates of the compound of Example 3, an example of a strong rare-earth chelate, were determined and the percent dose in the liver was used as an in vivo screening procedure to qualitatively estimate the stability of the chelates. Chelates of NTA and EDTA are included for comparison. Also samarium was injected as samarium chloride in unchelated form as a control.

Sprague-Dawley rats weighing from 150 to 200 g were purchased from Charles River Laboratories. These animals were placed in cages and fed water and food ad libitum. The animals were acclimated for at least five days before use. Prior to injection of complex, the animals were placed under a heat lamp (15 to 30 minutes) to dilate the tail vein. The animal was then placed in a restraining cage, the tail cleaned with an alcohol swipe, and the animal injected (50 to 200 $\mu$l) via the tail vein. After injection, the animal was placed in another cage for two hours after which time the animal was sacrificed by cervical dislocation. The animal was then dissected, the parts rinsed with deionized H$_2$O, patted dry, and weighed into a tared counting vial. At least three standards of the same material as injected were prepared and counted with the animal tissues. Percent of dose is the number of counts in the organ divided by the number of counts in the standard multiplied by 100 (see the following Table).

| | Biodistribution Data | | |
|---|---|---|---|
| Example No. | Ligand of Ex.* | Metal | % Injected Dose in Liver |
| I | 3 | Y | 0.17 |
| II | 3 | Sm | 0.29 |
| (A) | EDTA | Sm | 8.4 |
| (B) | EDTA | Sm | 4.4 |
| (C) | NTA | Sm | 8.6 |
| (D) | SmCl$_3$ | Sm | 39 |

*Complexes were prepared at ligand/metal ratios of 1:1 for Examples I and II; at 5:1 for Example A; and at about 300:1 for Examples B and C.

EXAMPLES III and E

The 1:1 complexes of yttrium (spiked with a tracer amount of $^{90}$Y) with the ligand of Example 3, which is BA-DOTA, and EDTA (Comparative E) were prepared by methods described previously. Several 100 $\mu$L aliquots were then transferred to separate centrifuge tubes. Excess Y(III) was added such that the total volume change is minimized and the time noted. One-half hour after metal addition, the percent complex was determined by the cation exchange method described previously and this was compared to the original amount of complex. The percent complex versus added metal gives an indication as to the lability of the ligand-metal complex. The results are given in the Table.

| | Complex Study | |
|---|---|---|
| Metal/Ligand Molar Ratio | % Complex | |
| | BA—DOTA | EDTA |
| 1 | 80 | 98 |
| 10 | — | 86 |
| 100 | — | 78 |
| 250 | 88 | 48 |
| 500 | 80 | 16 |

EXAMPLE IV

Preparation of 1-[2-(4-isothiocyanatophenyl)ethyl]-1,4,7,10-tetraazacyclododecane-4,7,10-triacetic acid, samarium-153 complex; [$^{153}$Sm(SCN-EA-DO3A)] complex To 100 $\mu$l of $^{153}$Sm in 0.1N HCl was added 5 $\mu$l of SCN-EA-DO3A (5 mM in 50 mM HEPES, pH 8.2) (prepared in Example 18). This was mixed on a vortex mixer, and HEPES buffer (0.5M, pH 8.9) was added gradually (about 25 $\mu$l total) to adjust the pH to around 7. The progress of the chelation was monitored by HPLC on GF-250 column (HPLC System I). Yields around 50% were obtained.

EXAMPLE V

Preparation of $\alpha$-[2-(4-aminophenyl)ethyl]-1,4,7,10-tetraazacyclododecane-1,4,7,10-tetraacetic acid, samarium-153 complex; [$^{153}$Sm(PA-DOTA)] complex To 150 microliters ($\mu$l) of $^{153}$Sm solution in 0.1N HCl (approximately 4.6 mCi) were added 1 $\mu$l of sodium acetate (2.0M) and 9 $\mu$l of $\alpha$-[2-(4-aminophenyl)ethyl]-1,4,7,10-tetraazacyclododecane-1,4,7,10-tetraacetic acid mixed ammonium, potassium salt (5 mmole in 50 mmole HEPES, pH 8.5, prepared by the procedure of Example 9). The mixture was mechanically shaken and titrated gradually with a HEPES buffer (0.5M, pH 8.9; approximately 31 $\mu$l added) to pH 7. This was then heated at 98° C. in a sand bath for 1 hour. Upon termination, 5 $\mu$l of the mixture was used for analysis on a Mono-Q ™ column on HPLC System II, eluted with a gradient solvent system (0–15 minutes, from 0 to 100% B; where A=water, and B=1.0M ammonium acetate and 0.1 mmole EDTA). Yields of 85–95% based on $^{153}$Sm were obtained. The a-[2-(4-aminophenyl)ethyl]-1,4,7,10-tetraazacyclododecane-1,4,7,10-tetraacetic acid, samarium-153 complex thus prepared was characterized by comparison with the identical non-radioactive sample, by their respective chromatographic behavior on Mono-Q ™ and GF-250 columns. Further evidence of the presence of the radioactive complex was determined by the conversion to the isothiocyanato derivative and its subsequent conjugation to antibody. The complex has also been prepared without heating (at ambient temperature) by incubation for 6 to 18 hours to result in 70–80% yield.

EXAMPLE VI

Preparation of $\alpha$-[2-(4-isothiocyanatophenyl)ethyl]-1,4,7,10-tetraazacyclododecane-1,4,7,10-tetraacetic acid, samarium-153 complex; [$^{153}$Sm(SCN-PA-DOTA)] complex To the reaction mixture obtained in Example V was added 2 $\mu$l of HEPES buffer (0.5M, pH 8.9), 2 $\mu$l of thiophosgene and 0.2 ml of chloroform. The mixture was mechanically shaken vigorously 2 or 3 times for a few seconds each time. The chloroform layer was discarded and the aqueous layer which contained mainly the desired product was saved and further purified. The yield of α-[2-(4-isothiocyanatophenyl)ethyl]-1,4,7,10-tetraazacyclododecane- 1,4,7,10-tetraacetic acid, samarium-153 complex, based on $^{153}$Sm activity measurement by HPLC on GF-250 column using HPLC System I, was 85–90%. To purify, the aqueous layer was passed through a Sep-Pak TM C-18 cartridge and eluted with 90% acetonitrile in water. The first 300 μl of effluent was discarded, and the SCN-derivative which came off in the next 900 μl was characterized by HPLC on GF-250. The recovery of the $^{153}$Sm activity was better than 90%. The bulk of the solvent was then evaporated over a period of 1.5 to 2 hours, and the residue was used for conjugation to antibody.

EXAMPLE VII

Preparation of
α-(4-aminophenyl)-1,4,7,10-tetraazacyclododecane-1,4,7,10-tetraacetic acid, samarium-153 complex; [$^{153}$Sm (BA-DOTA)] complex To 200 μl of $^{153}$Sm solution in 0.1N HCl were added 1 μl of sodium acetate (2.0M) and 12 μl of α-(4-aminophenyl)-1,4,7,10-tetraazacyclododecane-1,4,7,10-tetraacetic acid (5 mmole in 50 mmole HEPES, pH 8.5) (prepared by the procedure of Example 3). The mixture was mechanically shaken and titrated gradually with a HEPES buffer (0.5M, pH 8.9; approximately 38 μl added) to pH 7. This was then heated at 98° C. in a sand bath for 1 hour. Upon termination, 5 μl of the mixture was used for analysis on a Mono-Q TM column (HPLC System II, eluted with a gradient solvent system: 0–15 minutes, from 0 to 100% B; where A=water, and B=1.0M ammonium acetate and 0.1 mmole EDTA). In general, yields of 85–95% based on $^{153}$Sm were obtained. The complex has also been prepared by incubation of the mixture at room temperature for 12–18 hours which resulted in a yield of the title product of 80–90%. The α-(4-aminophenyl)-1,4,7,10-tetraazacyclododecane-1,4,7,10-tetraacetic acid, samarium-153 complex thus prepared was characterized by comparison with an authentic sample by their chromatographic behavior on the Mono-Q TM column, conversion to the isothiocyanato derivative and its subsequent conjugation to antibody.

EXAMPLE VIII

Preparation of
α-(4-isothiocyanatophenyl)-1,4,7,10-tetraazacyclododecane-1,4,7,10-tetraacetic acid, samarium-153 complex; [$^{153}$Sm(SCN-BA-DOTA)] complex.

To the reaction mixture obtained in Example VII were added 2 μl of HEPES buffer (0.5M, pH 8.9), 2 μl of thiophosgene and 0.2 ml of chloroform. It was mechanically shaken vigorously 2 or 3 times for a few seconds each time. The chloroform layer was discarded and the aqueous layer which contained mainly the desired product was saved and further purified. The yield of α-(4-isothiocyanatophenyl)-1,4,7,10-tetraazacyclododecane-1,4,7,10-tetraacetic acid, samarium-153 complex, as analyzed by HPLC on GF-250 column based on the $^{153}$Sm activity using the HPLC System I was over 90%. To purify, the aqueous layer was passed through a Sep-Pak TM C-18 cartridge and eluted with 90 percent acetonitrile in water. The first 0.3 ml of effluent was discarded, and the desired product came off in the next 1.2 ml, with 86–93% recovery. The bulk of the solvent was then evaporated over a period of about 2 hours, and the residue was used for conjugation to antibody.

EXAMPLE IX

Conjugation of
1-[2-(4-isothiocyantophenyl)ethyl]-1,4,7,10-tetraazacyclododecane-4,7,10-triacetic acid, samariuim-153 complex to antibody; [$^{153}$Sm(SCN-EA-DO3A)]IgG conjugate The antibody used was CC-49, a murine monoclonal IgG that binds to an epitope of TAG-72, a tumor associated antigen. To conjugate, 187 μl of the antibody solution (1.20×10$^{-4}$M in 50 mM HEPES, pH 8.5) was mixed with 4.5×10$^{-8}$ moles of $^{153}$Sm(SCN-EA-DO3A) prepared as described in Example IV followed by addition of a sodium carbonate solution (1.0M) to raise the pH to 8.9. The reaction was allowed to continue for 2 hours at room temperature. Upon termination, the $^{153}$Sm labeled IgG was isolated by centrifugal gel filtration on Sephadex G-25 (2.2 ml) disposable columns, and further purified by HPLC on GF-250 column, eluted with a citrate buffer (0.25M, pH 7.4). The fractions contained the labeled IgG were pooled, concentrated and exchanged (3×) into PBS by use Centricon TM concentrators. The specific activity of $^{153}$Sm labeled IgG thus prepared was about 0.16 μCi/μg of protein. The integrity of the [$^{153}$Sm(EA-DO3A)]-IgG preparation was verified by HPLC (Sivakoff, S. I., *BioChrom.* 1(1), 42–48 (1986)] and standard biochemical procedures, e.g. sodium dodecyl sulfate:polyacrylamide gel electrophoresis and autoradiography, and solid phase radioimmunoassay (RIA). [See David Colcher et al., *Cancer Res.* 43, 736–742 (1983).]

EXAMPLE X

Conjugation of
1-[2-(4-isothiocyanatophenyl)ethyl]-1,4,7,10-tetraazacyclododecane-4,7,10-triacetic acid, samarium-153 complex to Fragment F(ab')$_2$of CC-49; [$^{153}$Sm(SCN-EA-DO3A)]-Fragment F(ab')$_2$ of CC-49

The F(ab')$_2$ fragment of CC-49, prepared by enzymatic digestion according to the procedure described by Lamoyi and Nisonoff [E. Lamoyi and A Nisonoff, *J. Immunol. Methods*, 56, 235–243 (1983)], (225 μl of 1×10$^{-4}$M in 50 mM HEPES, pH 8.5) was mixed with 2.9×10$^{-8}$ moles of $^{153}$Sm(SCN-EA-DO3A) prepared as described in Example IV. Sodium carbonate (1.0M, about 5 μl) was added to bring the pH to 8.9, and the reaction was continued for about 2.5 hours. Upon termination, the $^{153}$Sm labeled fragment was isolated and characterized as described in Example IX.

EXAMPLE XI (A AND B)

Figure 2:
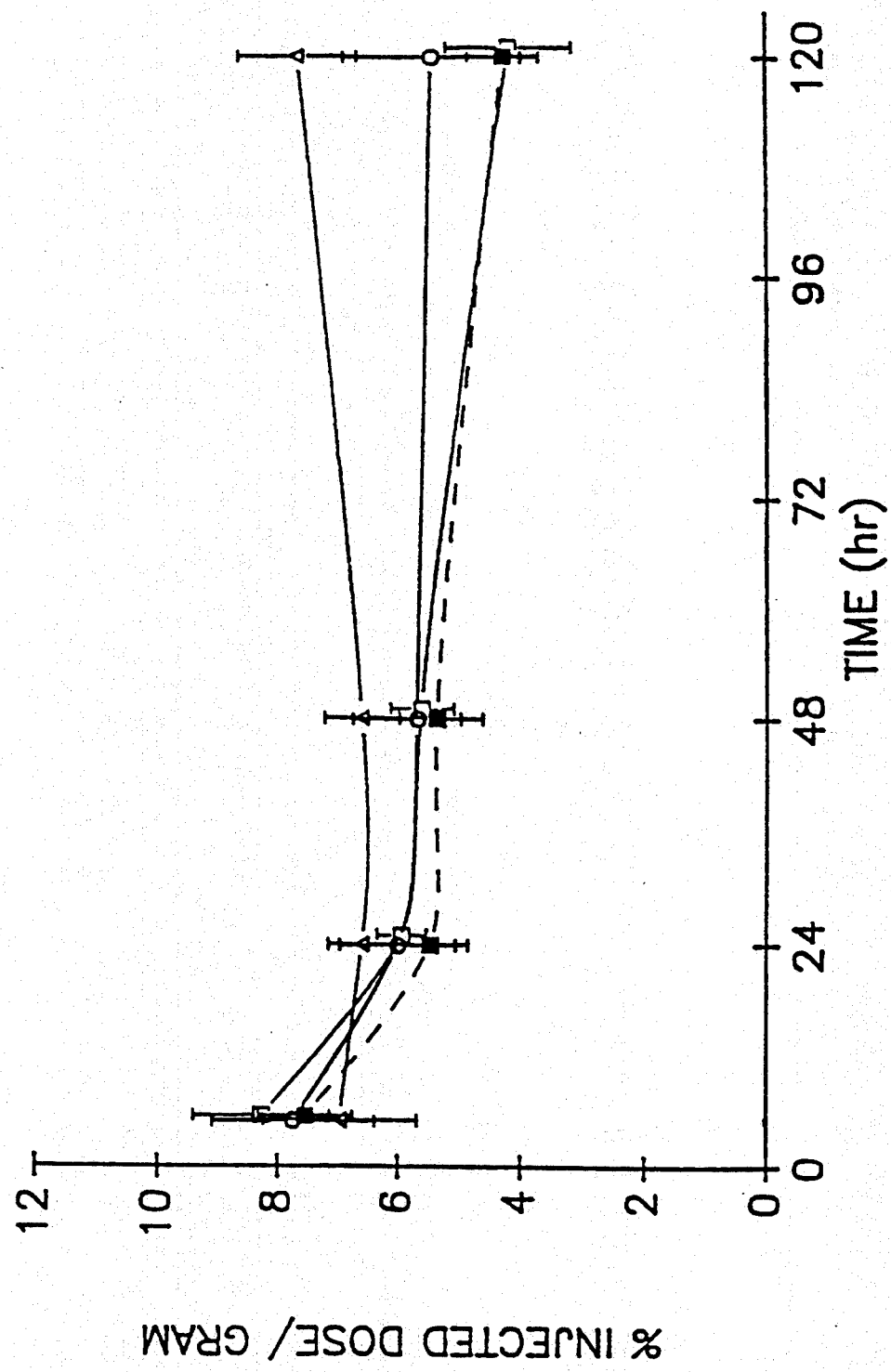
Figure 3:
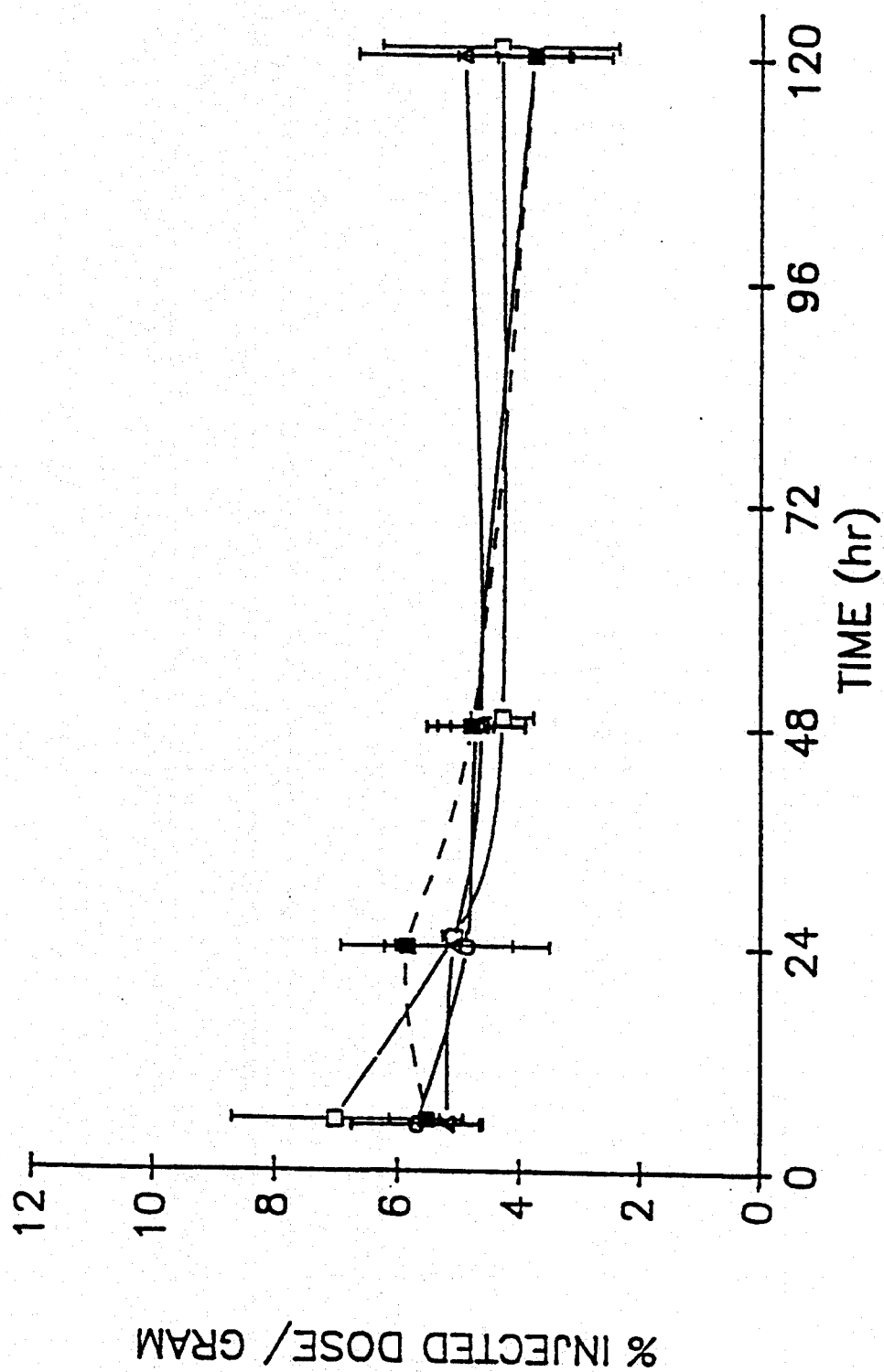
Figure 4:
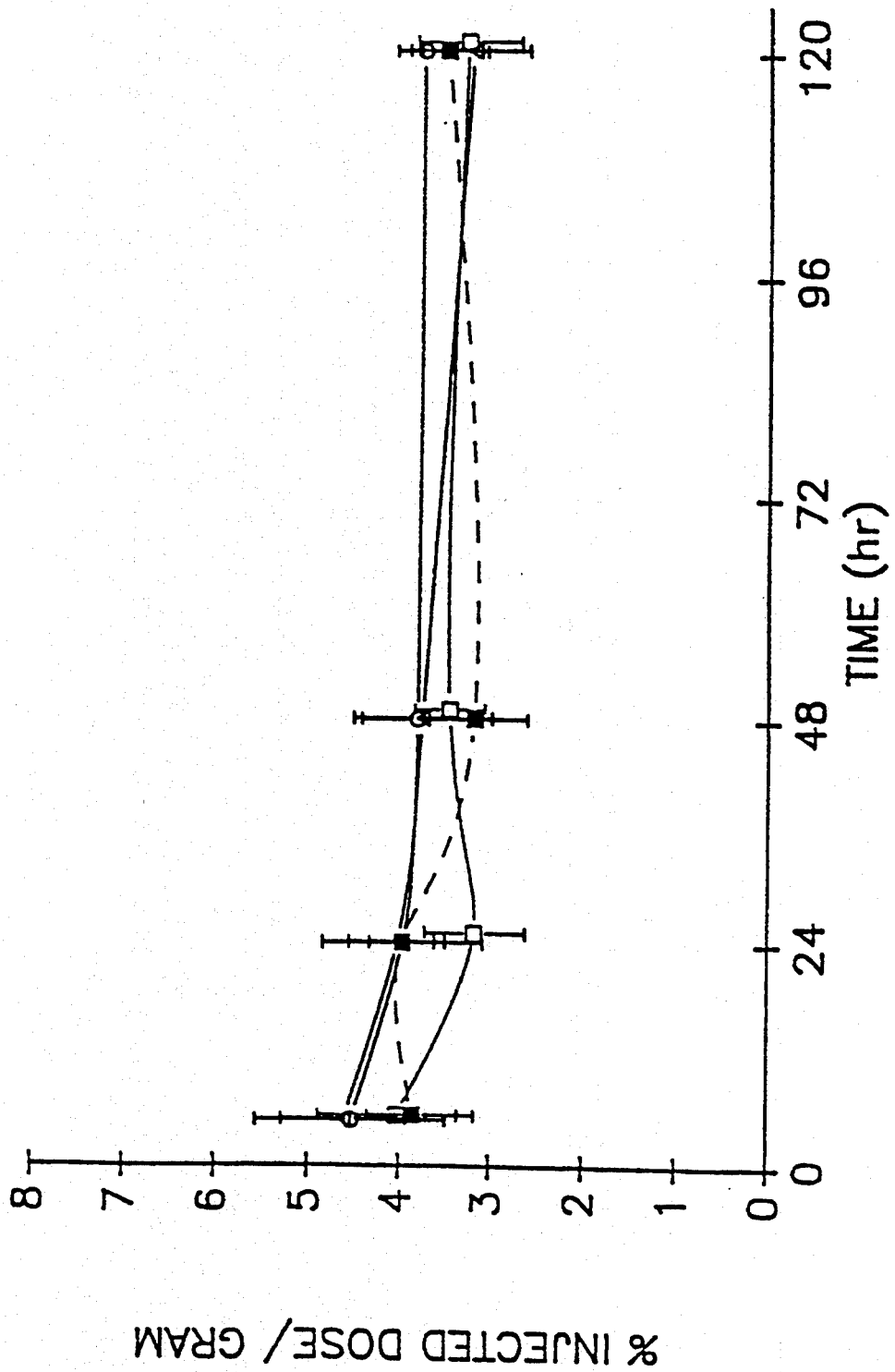
Figure 5:
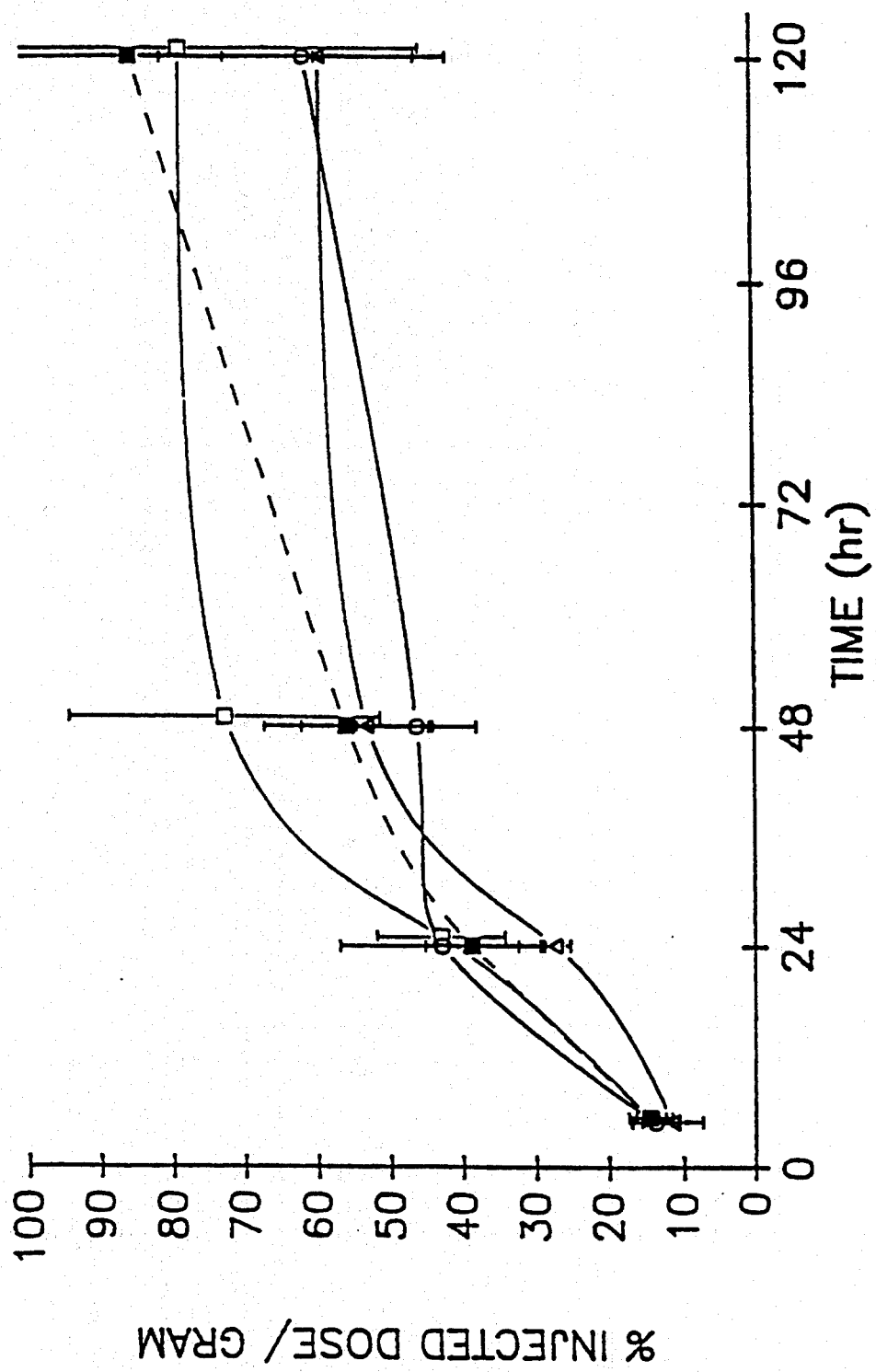
Figure 6:
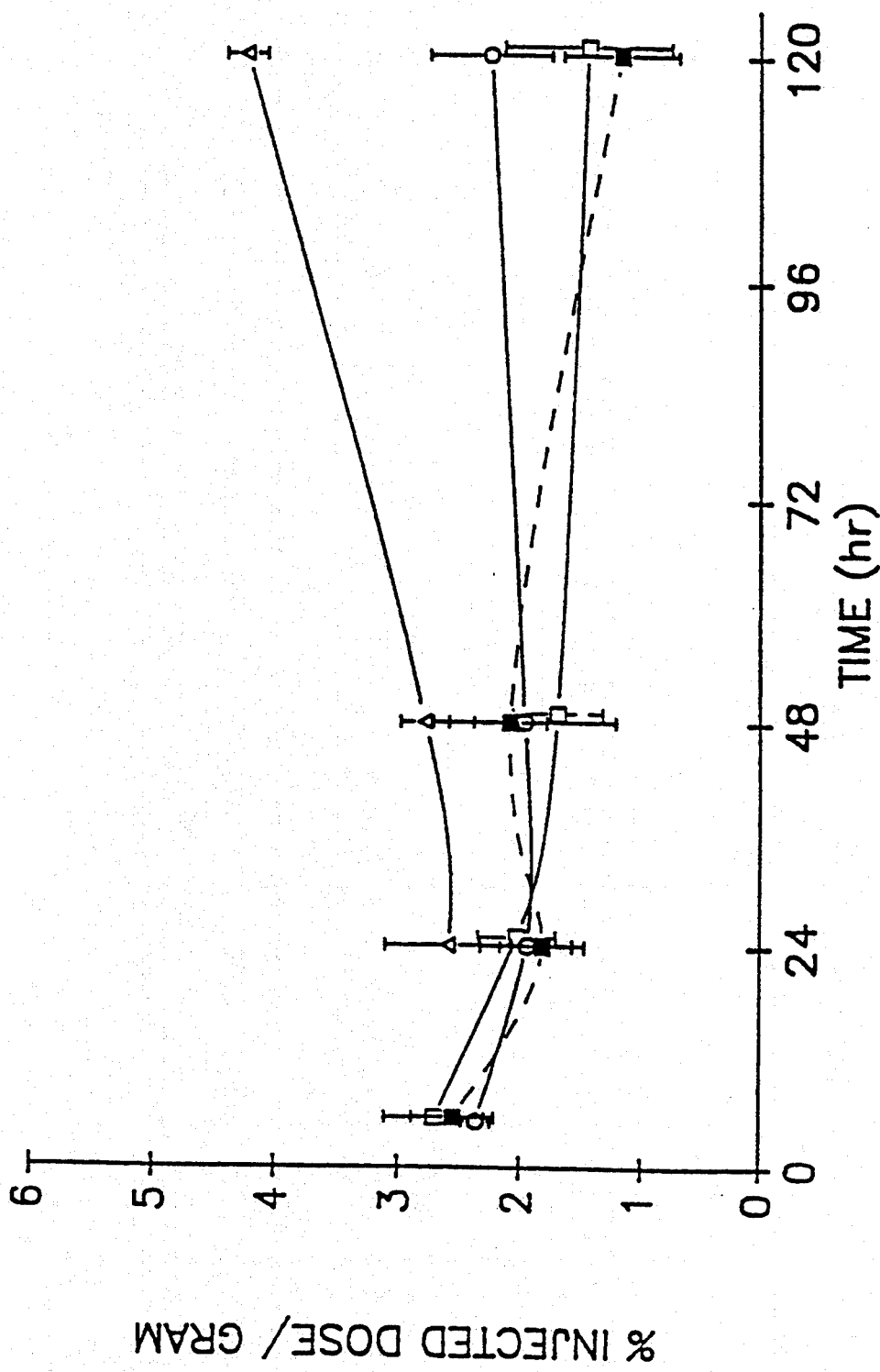
Figure 7:
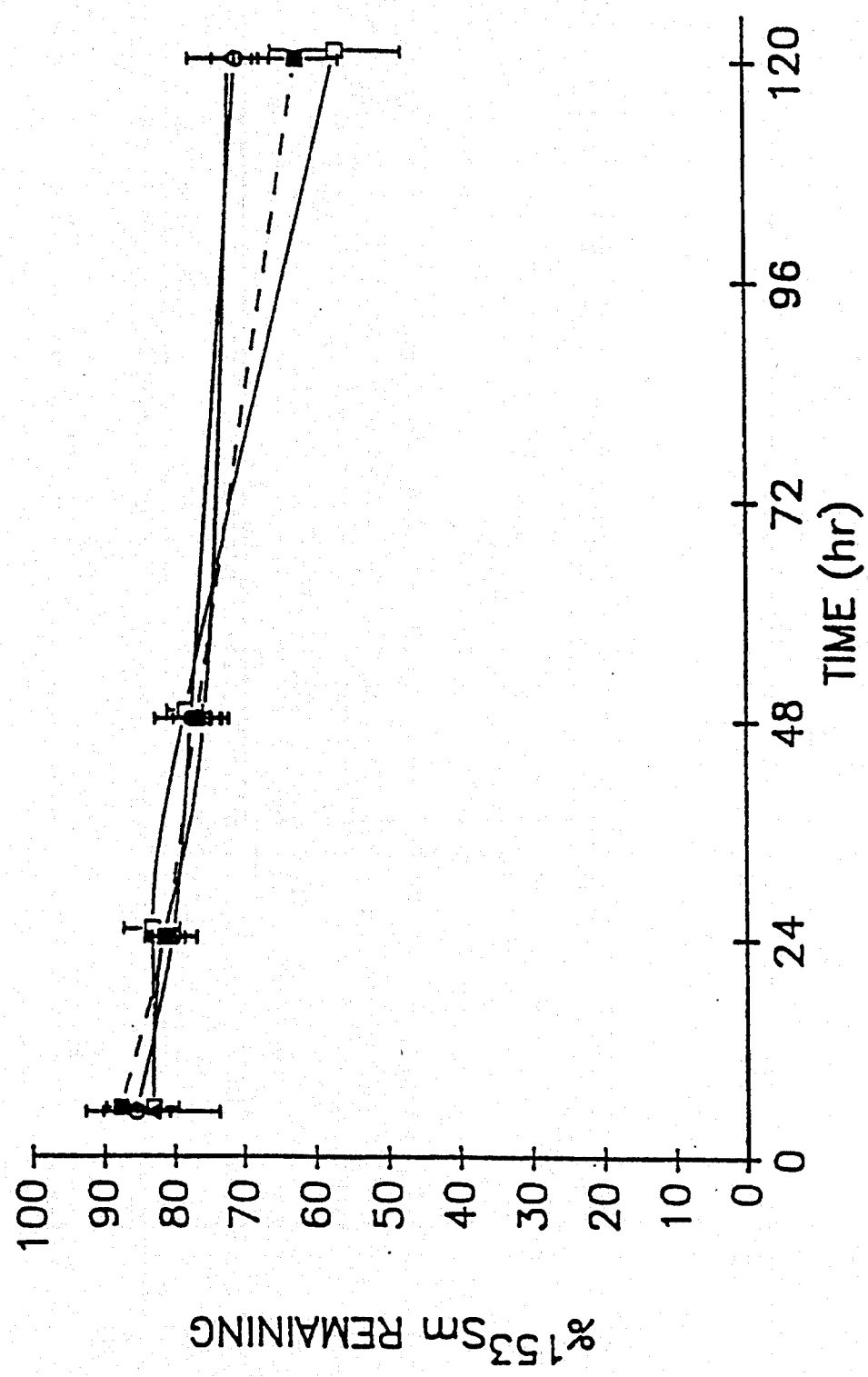
Figure 8:
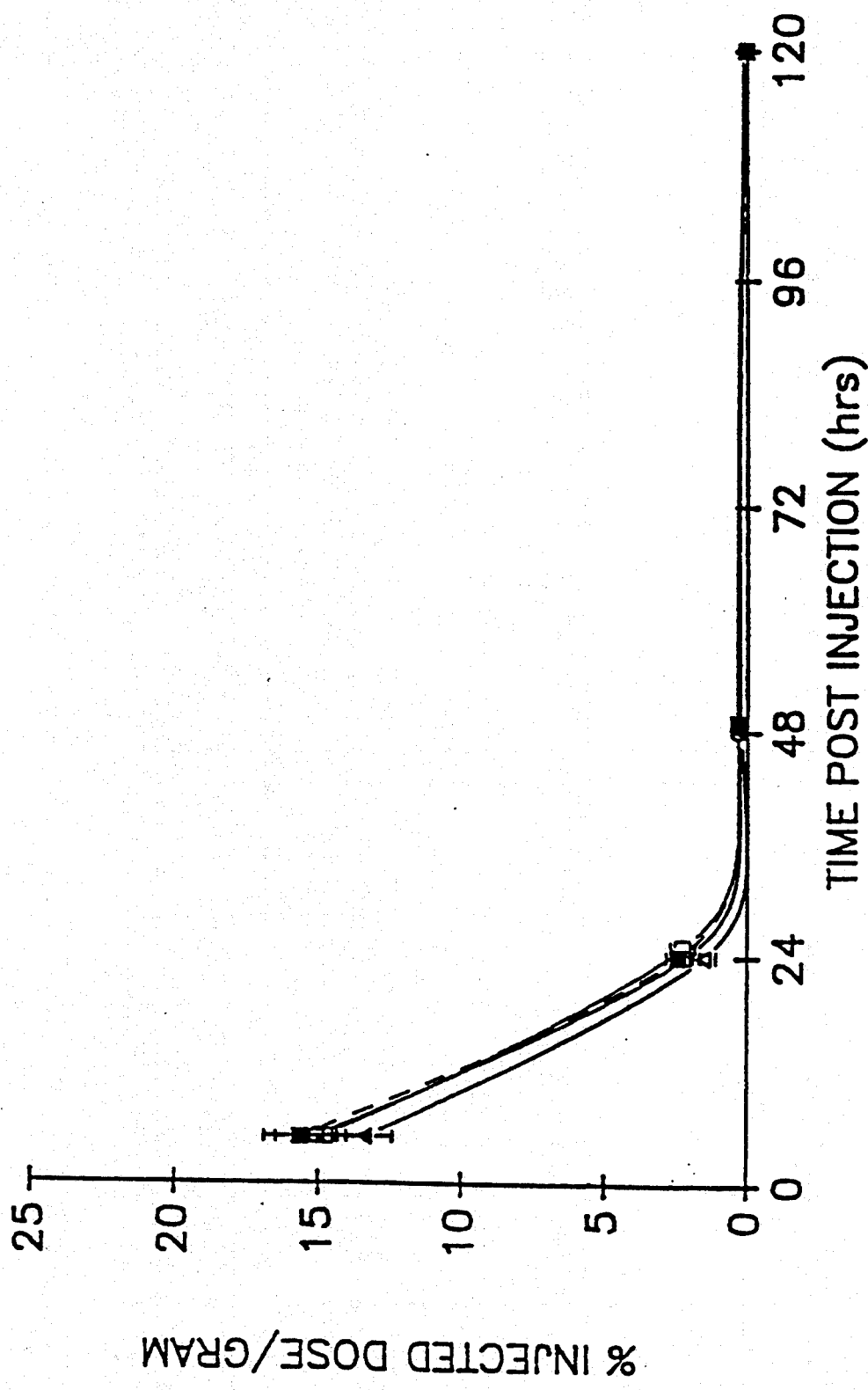
FIGS. 8–14 and 22–28 show the biodistribution of $^{153}$Sm as administered as a conjugate containing $^{153}$Sm of the present invention. The conjugate of the present invention used CC$_{49}$-F(ab')$_2$ as the antibody fragment. The biodistribution was determined in nude mice bearing LS 174-T tumor.
Figure 9:
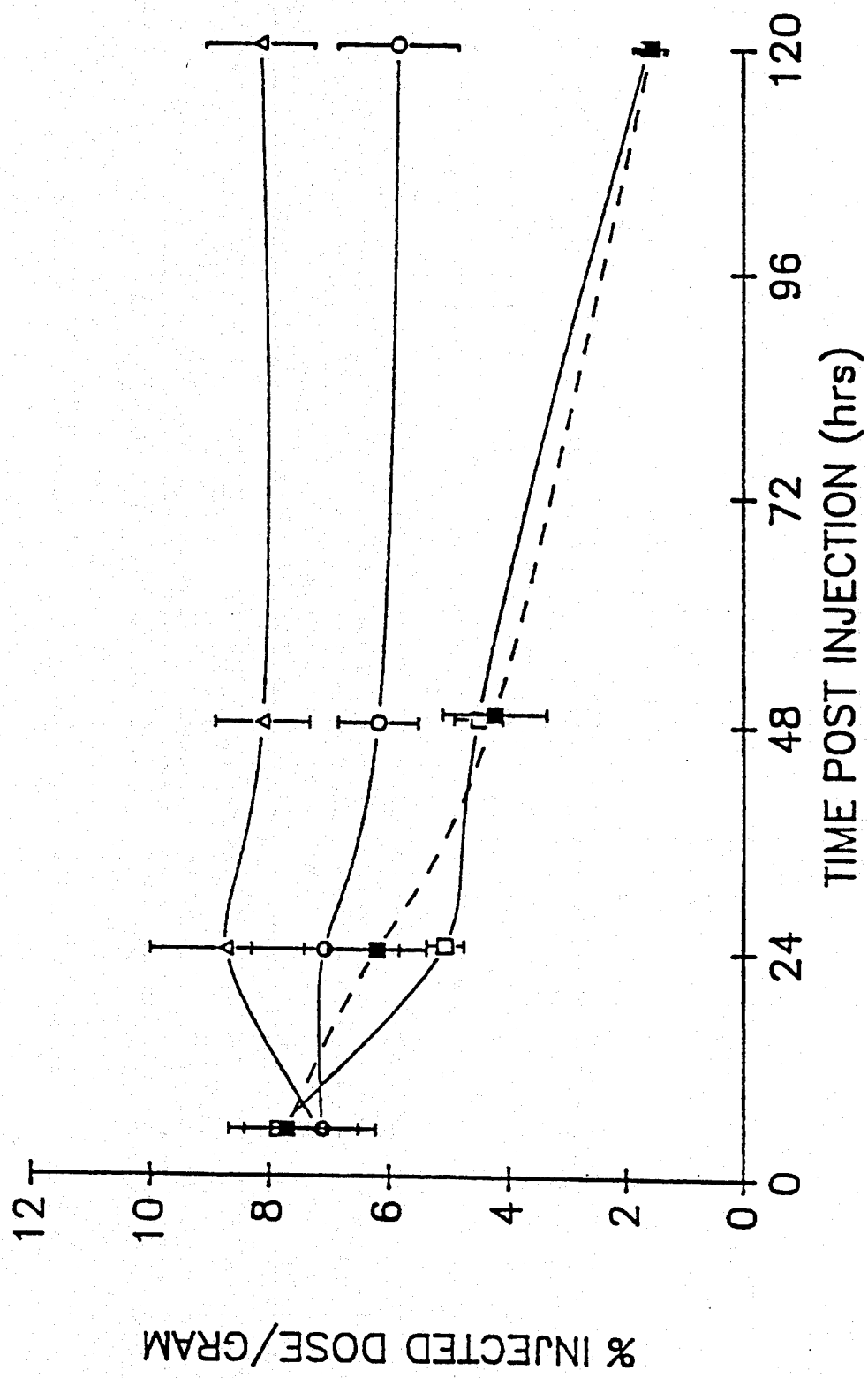
Figure 10:
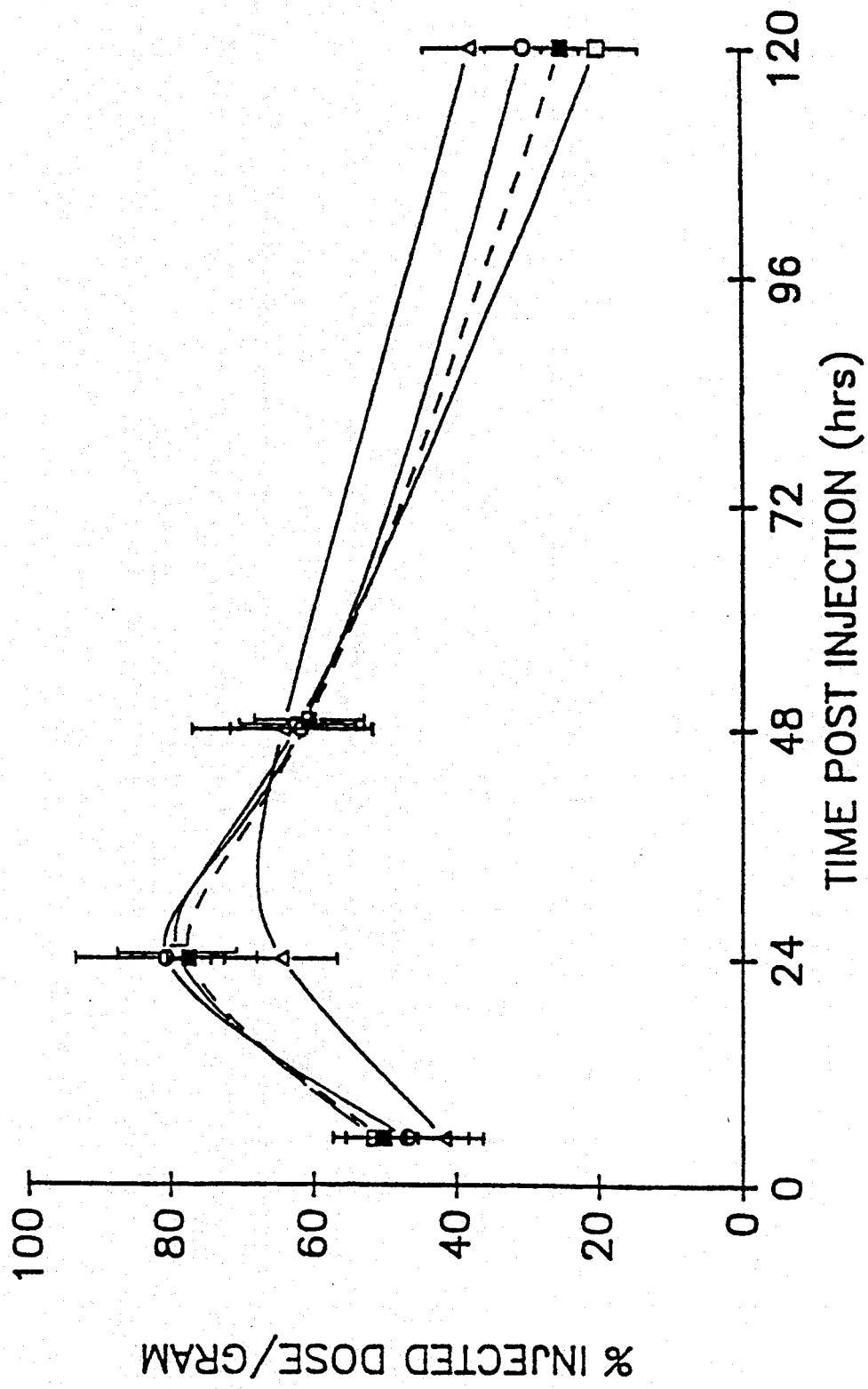
Figure 11:
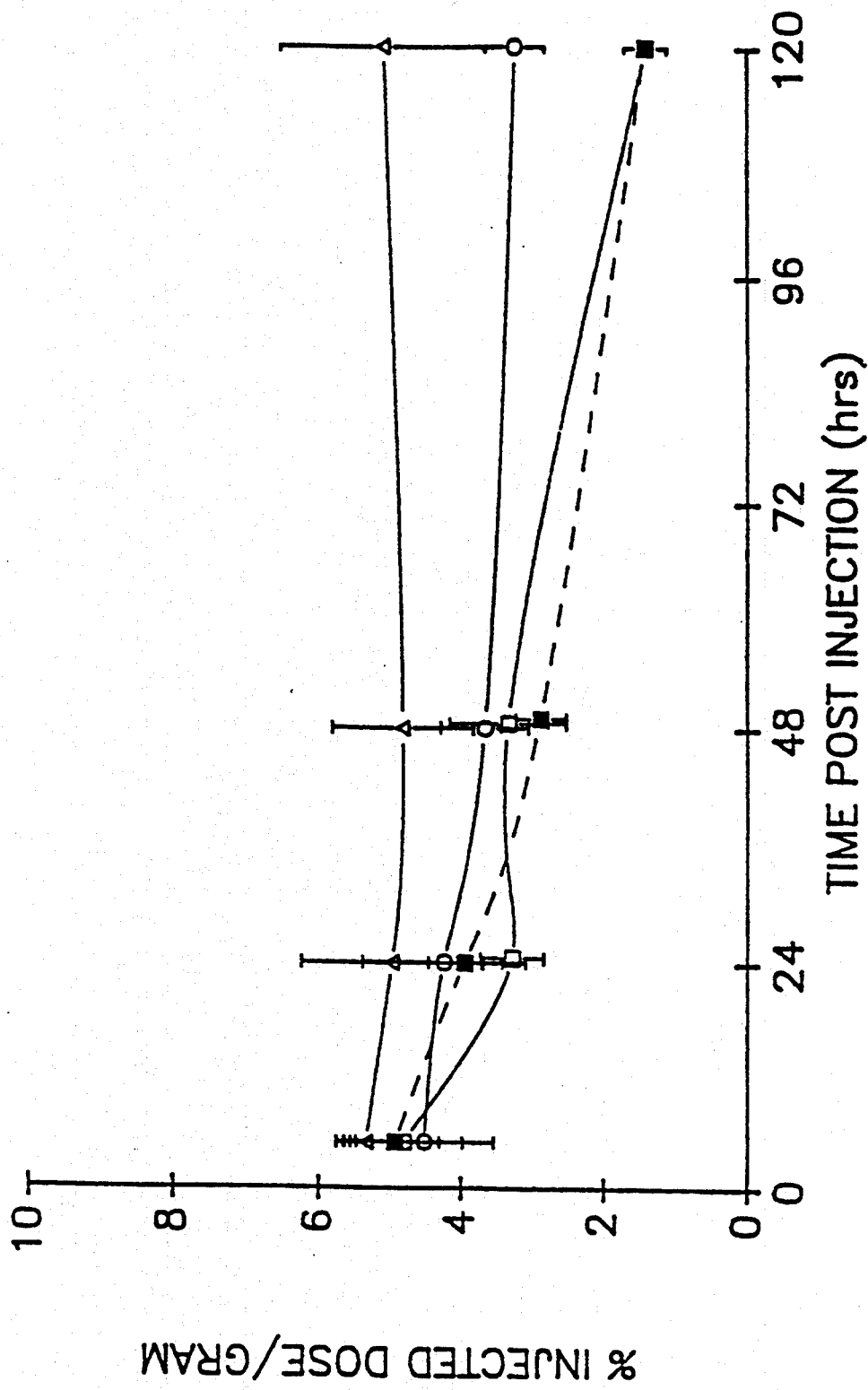
Figure 12:
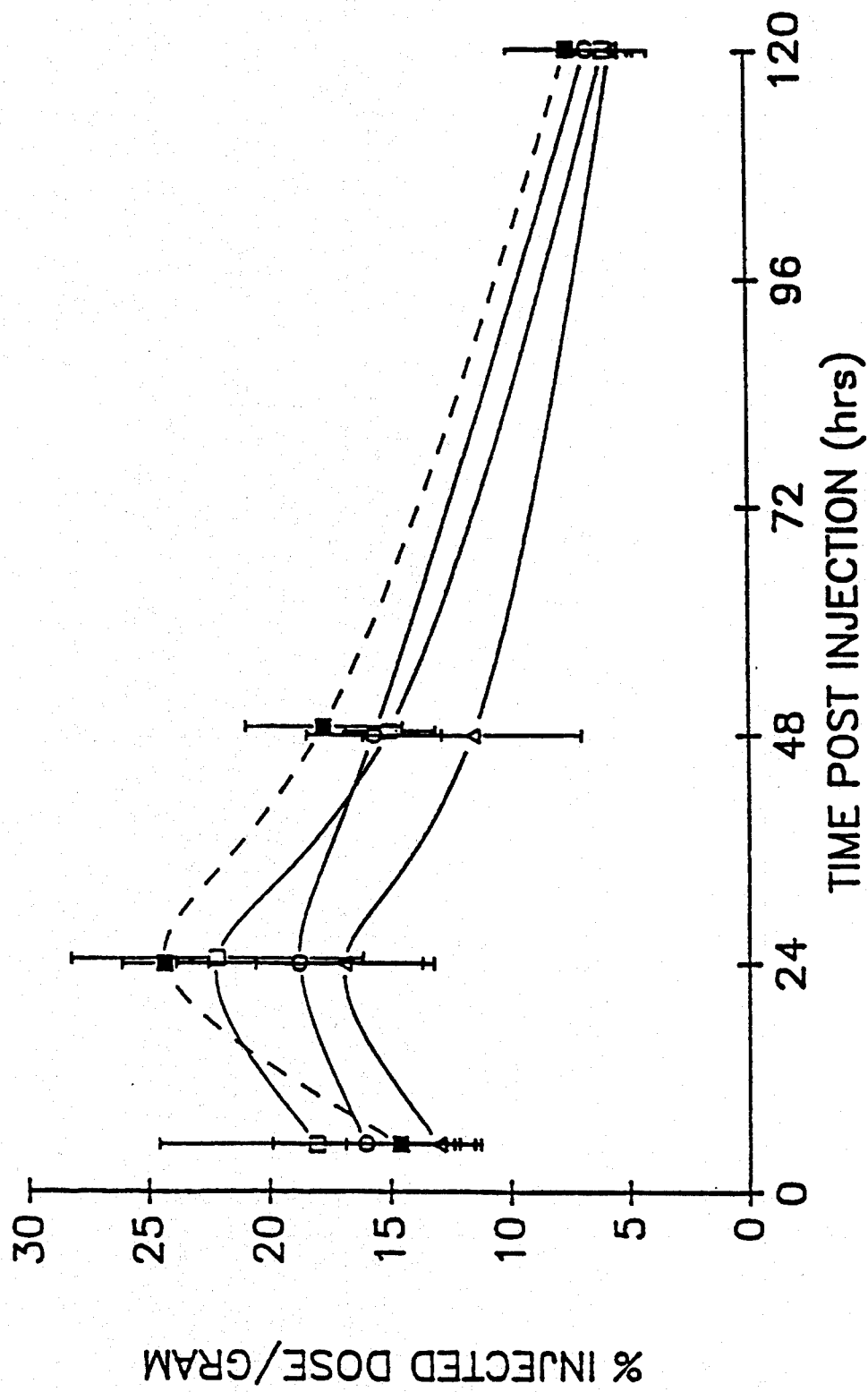
Figure 13:
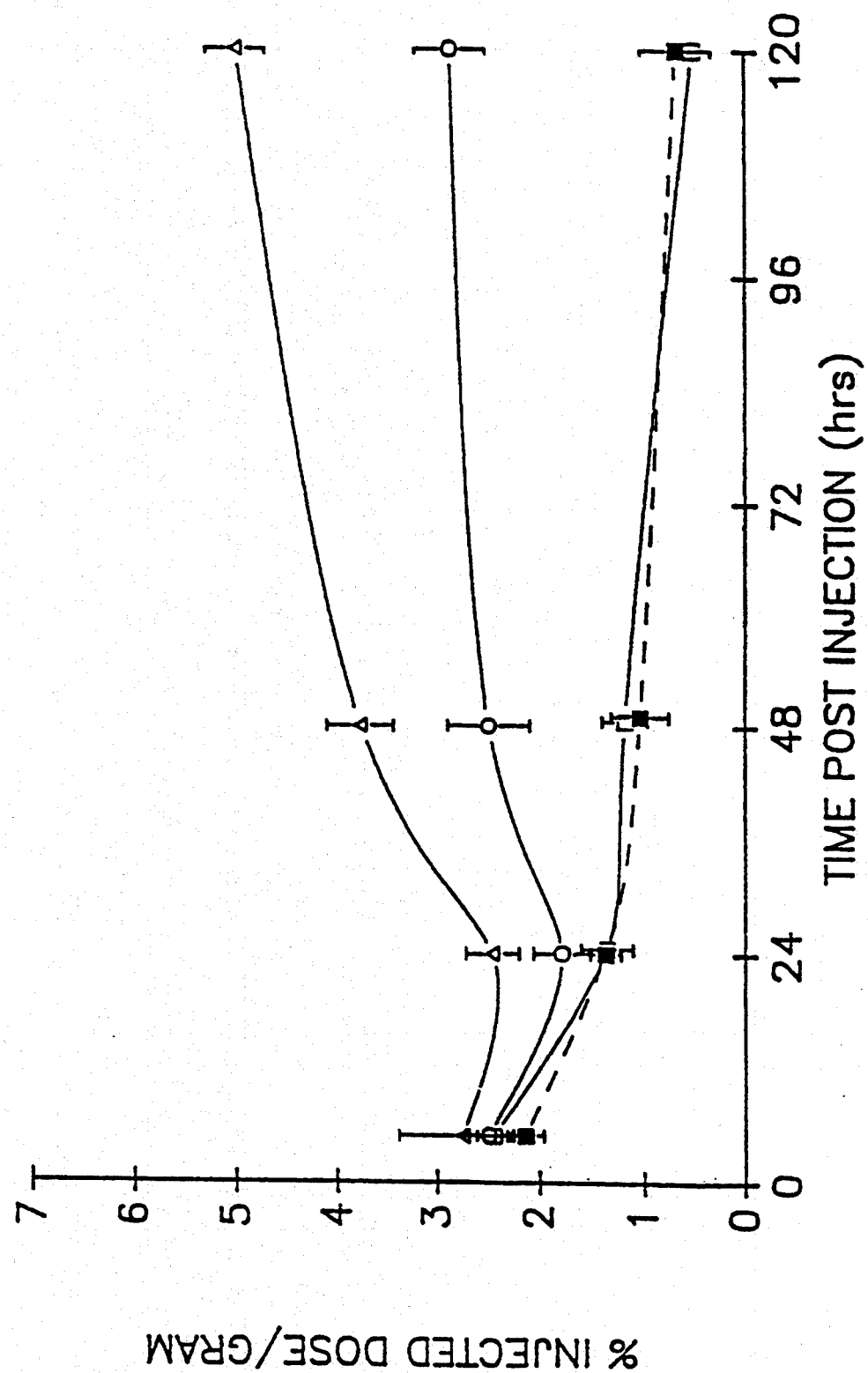
Figure 14:
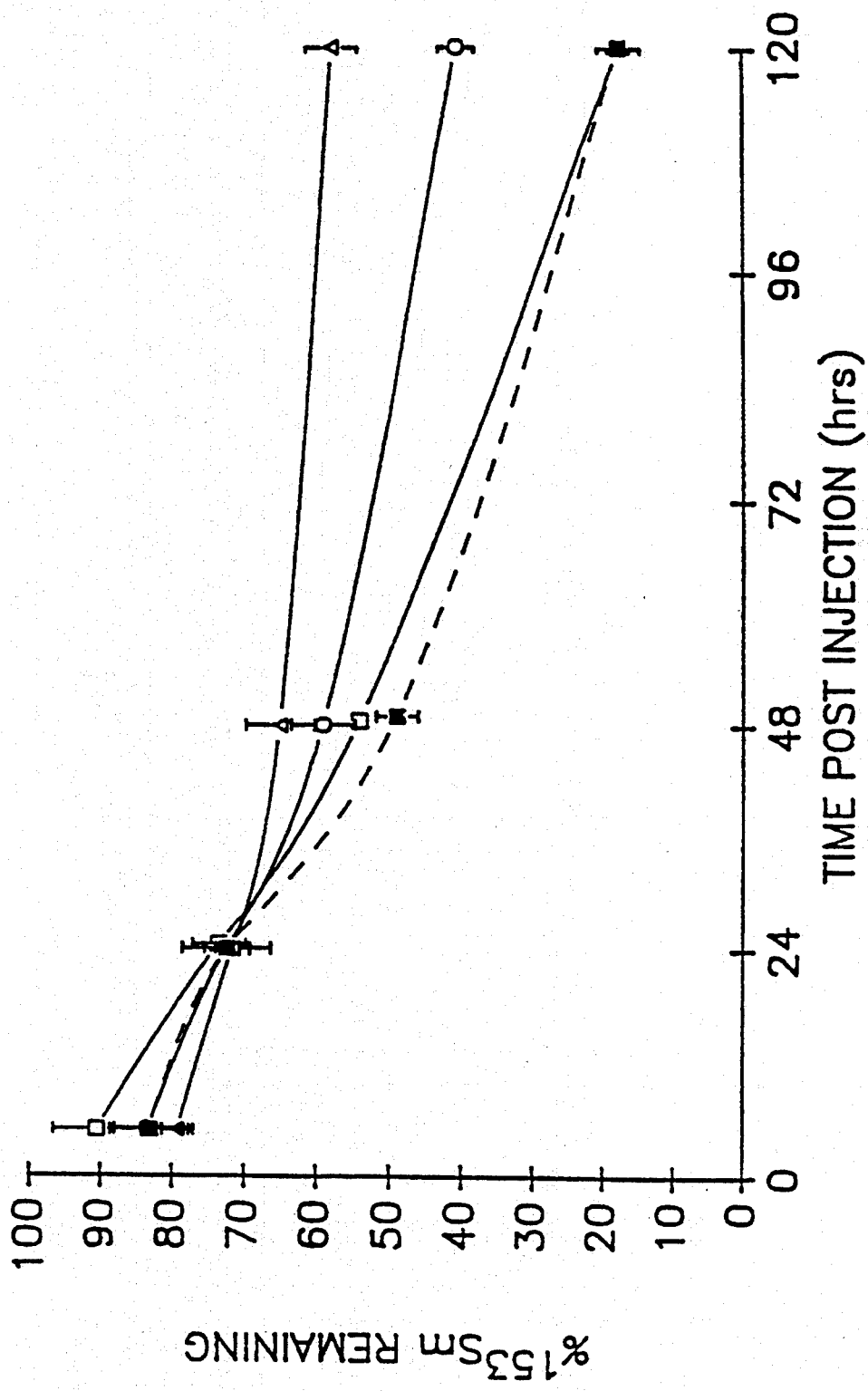

In vivo localization of [$^{153}$Sm(EA-DO3A)]-IgG and [$^{153}$Sm(EA-DO3A)]-F(ab')$_2$ The utility of the $^{153}$Sm(EA-DO3A) labeled IgG (from Example IX) and F(ab')$_2$ of CC-49 (from Example X) was demonstrated by the uptake of the labeled materials by human tumor xenograft in athymic mice. Thus female athymic (Nu/Nu, CD1 background) mice were inoculated subcutaneously (S.C.) (0.1 ml/source) with the human colon carcinoma cell line, LS-174 T (approximately 1×10$^6$ cells/animal). Approximately 2 weeks after inoculation, each animal was injected via the tail vein with about 2 μCi (15–30 μg) of $^{153}$Sm labeled antibody in PBS. The mice were sacrificed at various time intervals. After exsanguination, the tumor and selected tissues were excised and weighed, and radioactivity was measured in a gamma counter. The counts per minute (CPM) of $^{153}$Sm in each tissue was determined and expressed as CPM per gram of tissue per injected dose multiplied by 100 (% injected dose/gram). Results are shown in FIGS. 1–14 and Tables IA and IB. The $^{153}$Sm(SCN-Bz-DTPA) labeled IgG and F(ab')$_2$ of CC-49 (from Example ZA) were included in the study for comparison. Results are shown in Table IC and ID.

EXAMPLE XII

Conjugation of
α-[2-(4-isothiocyanatophenyl)ethyl]-1,4,7,10-tetraazacyclododecane-1,4,7,10-tetraacetic acid, samarium-153 complex to antibody;
[$^{153}$Sm(SCN-PA-DOTA)]-IgG conjugate.

The antibody used was CC-49, a murine monoclonal IgG that binds to an epitope of TAG-72, a tumor associated antigen. To conjugate, 178 μl of the antibody solution (1.26×10$^{-4}$M in 50 mmole HEPES, pH 8.5) was mixed with 3.4×10$^{-8}$ moles of α-[2-(4-isothiocyanatophenyl)ethyl]-1,4,7,10-tetraazacyclododecane-1,4,7,10-tetraacetic acid, samarium complex (prepared as described in Example VI), followed by addition of a sodium carbonate solution (1.0M, about 17 μl) to raise the pH to about 8.9. The reaction was allowed to continue for 2 hours at room temperature. Upon termination, the $^{153}$Sm labeled IgG was isolated by centrifugal gel filtration on Sephadex TM G-25 (2.2 ml) disposable columns, and further purified by HPLC on GF-250 column, eluted with a titrate buffer (0.25M, pH 7.4). The fractions which contained the labeled IgG were pooled, concentrated and exchanged (3 times) into PBS by use of Centricon TM concentrators. The specific activity of the $^{153}$Sm labeled IgG thus prepared was about 0.16 μci/μg of protein. The homogeneity and integrity of the α-[2-(4-isothiocyanatophenyl)-ethyl]-1,4,7,10-tetraazacyclododecane- 1,4,7,10-tetraacetic acid, samarium-153 complex-IgG preparation was verified by HPLC and standard biochemical procedures as Example IX.

The following Example is an alternative for making labeled antibody conjugates, which involves first conjugation of the BFC to the antibody, and the subsequent chelation to yield the radionuclide-BFC labeled Ab.

EXAMPLE XIIA

Preparation of
α-[2-(4-aminophenyl)ethyl]-1,4,7,10-tetraazacyclododecane-1,4,7,10-tetraacetic acid—Ab CC49 conjugate
(IgG CC$_{49}$-PA-DOTA); and the sebsequent chelation with $^{153}$Sm to form $^{153}$Sm-labeled antibody (IgG CC$_{49}$-PA-DOTA-$^{153}$Sm)

The $^{153}$Sm(PA-DOTA) labeled antibody can be prepared by first coupling the BFC, e.g. α-[2-(4-isothiocyanatophenyl)ethyl]-1,4,7,10-tetraazacyclododecane-1,4,7,10-tetraacetic acid (SCN-PA-DOTA), to an antibody at pH 8–9, followed by chelation with $^{153}$Sm at pH 6 at room temperature for several hours.

In a typical experiment, IgG CC-49 was concentrated and exchanged three times into a carbonate buffer (50 mM, Ph 9.1) in a Centricon TM Concentrator (30 K molecular weight cut off) to leave a solution with antibody concentration greater than 1.5×10$^{-4}$M. To form the conjugate, 161 μl of the antibody solution, containing 25×10$^{-9}$ mole of IgG CC-49, was mixed with 5 μl of the SCN-PA-DOTA (5mM concentration in the same carbonate buffer, prepared by the procedure of Example 18). The mixture was allowed to stand at room temperature for 5 hours, and terminated by filtration through the 30 K membrane in the Centricon TM Concentrator at 5000 rpm on the Sorvall RT centrifuge. The antibody conjugate was further washed with 2 ml of a 0.25M DTPA solution in PBS at pH 7.4 and five times (2 ml each time) with MES buffer (20 mM, pH 5.8); centrifuged for 30 min. after each wash. At the end, the PA-DOTA-IgG conjugate was concentrated to a minimum volume (about 100 μl) and its integrity checked by HPLC analysis on a GF-250 column. To the purified conjugate was added a mixture of $^{153}$Sm in 0.1N HCl (50 μl) and 20 μl of a MES buffer (1.0M, pH 6), mixed on a vortex mixer, and allowed to stand at room temperature overnight. Upon termination by centrifugal gel filtration, the amount of $^{153}$Sm incorporated, estimated by HPLC analysis, was 0.22 BFC-Sm/antibody. That $^{153}$Sm was associated with the antibody through chelation with the BFC, which was linked covalently to the antibody, and not due to non-specific binding was demonstrated by comparsion with results from the control experiment. In the control experiment, IgG CC-49 solution was mixed with $^{153}$Sm mixture under identical conditions. The antibody isolated in a similar manner, had no appreciable amount of $^{153}$Sm associated with it. Thus it indicated that non-specific binding of Sm-153 by the antibody did not take place under these conditions.

EXAMPLE XIII

Conjugation of
α-[2-(4-isothiocyanatophenyl)ethyl]-1,4,7,10-tetraazacyclododecane-1,4,7,10-tetraacetic acid,
samarium-153 complex to fragment F(ab')$_2$ of CC-49;
$^{153}$Sm(SCN-PA-DOTA)]-F(ab')$_2$ fragment The F(ab')$_2$ fragment of CC-49 [prepared by enzymatic digestion according to the procedure described by (E. Lamoyi et al., J. Immunol. Methods 56, 235–243 (1983)], (225 μl of 1×10$^{-4}$M in 50 mmole HEPES, pH 8.5) was mixed with 2.9×10$^{-8}$ moles of α-[2-(4-isothiocyanatophenyl)ethyl] -1,4,7,10-tetraazacyclododecane-1,4,7,10-tetraacetic acid, samarium-153 complex prepared as described in Example VI. Sodium carbonate (1.0M, about 9 μl) was added to bring the pH to around 8.9, and the reaction was continued for about 2.5 hours. The $^{153}$Sm labeled fragment was isolated and characterized as described in Example IX. The specific activity was around 0.4 μCi/μg.

EXAMPLE XIV (A AND B)

In vivo localization of the conjugate of α-[2-(4-isothiocyanatophenyl)ethyl]-1,4,7,10-tetraazacyclododecane-1,4,7,10-tetraacetic acid, samarium-153 complex labeled IgG and F(ab')$_2$; [$^{153}$Sm(SCN-PA-DOTA]-IgG and [$^{153}$Sm(SCN-PA-DOTA)]-F(ab')$_2$ The utility of the conjugate of α-[2-(4-isothiocyanatophenyl)ethyl]-1,4,7,10-tetraazacyclododecane-1,4,7,10-tetraacetic acid, samarium-153 complex labeled IgG and F(ab')$_2$ of CC-49 (from Example XII and XIII) was demonstrated by the uptake of the labeled materials by human tumor xenograft in athymic mice. The biolocalization was determined using the procedure described in Example XI. Results are shown in FIGS. 1 to 7 for IgG and FIGS. 8 to 14 for F(ab')$_2$, also Tables IIA and IIB.

The conjugate of $^{153}$Sm(SCN-Bz-DTPA) with IgG and F(ab')$_2$ labeled materials (prepared from Example ZA) were included in the study for comparison. (See Tables IC and ID.)

EXAMPLE XV

Conjugation of
α-(4-isothiocyanatophenyl)-1,4,7,10-tetraazacyclododecane-1,4,7,10-tetraacetic acid, samarium-153 complex to Antibody; [$^{153}$Sm(SCN-BA-DOTA)]IgG.

Whole IgG of CC-49 (174 μl of 1.2×10$^{-4}$M in 0.25M HEPES, pH 8.7) was mixed with 2.0×10$^{-8}$ moles of α-(4-isothiocyanatophenyl)-1,4,7,10-tetraazacyclododecane-1,4,7,10-tetraacetic acid, samarium-153 (2.8 mCi) prepared per Example VIII, followed by addition of a sodium carbonate solution (1.0M, about 2 μl) to maintain the pH about 8.7. The reaction was allowed to continue for 2.5 hours at room temperature. Upon termination, the $^{153}$Sm labeled IgG was isolated by centrifugal gel filtration on Sephadex TM G-25 (2.2 ml) disposable columns, and further purified by HPLC on GF-250 column, eluted with a citrate buffer (0.025M, pH 7.4). The fractions which contained the labeled IgG were pooled, concentrated and exchanged (3 times) into PBS by use of Centricon TM concentrators. Homogeneity and integrity of the samarium-153 labled IgG preparation was verified by HPLC and standard biochemical procedures as described in Example IX.

EXAMPLE XVI

Conjugation of
α-(4-isothiocyanatophenyl)-1,4,7,10-tetraazacyclododecane-1,4,7,10-tetraacetic acid, samarium-153 complex to Fragment F(ab')$_2$ of CC-49;
[$^{153}$Sm(SCN-BA-DOTA)]-fragment F(ab')$_2$ of CC-49

The F(ab')$_2$ of CC-49 (84 μl of 2.4×10$^{-4}$M in 0.25M HEPES buffer, pH 8.7), prepared by enzymatic digestion according to the procedure described by Lamoyi et al. was mixed with 2.1×10$^{-8}$ moles of α-(4 -isothiocyanophenyl)-1,4,7,10-tetraazacyclododecane-1,4,7,10-tetraacetic acid, samarium-153 complex (prepared by the procedure of Example VIII). Sodium carbonate (1.0M, about 2 μl) was added to bring the pH to 8.7, and the reaction was continued for about 2 hours. Upon termination, the $^{153}$Sm labeled fragment was isolated and characterized as described in Example IX.

EXAMPLE XVII (A AND B)

In vivo localization of α-(4-isothiocyanatophenyl)-1,4,7,10-tetraazacyclododecane-1,4,7,10-tetraacetic acid, samarium-153 complex labeled IgG (Example XV) and F(ab')$_2$ (Example XVI); [$^{153}$Sm(BA-DOTA)]-IgG and [$^{153}$Sm(BA-DOTA]-F(ab')$_2$ The in vivo study was conducted according to the protocol described in Example XI, and results are shown in FIGS. 1 to 14 and Tables IIIA and IIIB.

EXAMPLE XVIII (A AND B)

In vivo localization of α-[2-(4-isothiocyanatophenyl)ethyl]-1,4,7,10-tetraazacyclododecane-1,4,7,10-tetraacetic acid $^{177}$Lu-complex labeled IgG and F(ab')$_2$; [$^{177}$Lu(PA-DOTA)]-IgG and [$^{177}$Lu(PA-DOTA)]-F(ab')$_2$ The title compounds were prepared and in vivo studies were conducted according to protocol described in Examples V, VI, XI, XII and XIII and results are shown in Tables IVA and IVB.

EXAMPLE XIX (A AND B)

In vivo localization of α-[2-(4-isothiocyanatophenyl)ethyl]-1,4,7,10-tetraazacyclododecane-1,4,7,10-tetraacetic acid, yttrium-90 complex labeled IgG and F(ab')$_2$; [$^{90}$Y(PA-DOTA)]-IgG and [$^{90}$Y(PA-DOTA)]-F(ab')$_2$ The titled compounds were prepared and in vivo studies were conducted according to protocol described in Example XI with the exception that tissues were digested and counted by liquid scintillation and results are shown in Tables VA and VB.

EXAMPLE XX

In vitro pH stability of [$^{153}$Sm(BFC)]-CC-49-IgG and [$^{177}$Lu(BFC)]-CC-49-IgG The [$^{153}$Sm(BFC)]-CC-49-IgG or [$^{177}$Lu(BFC)]-CC-49-IgG was allowed to stand in a 0.2M NaOAc buffer at pH 6.0, 4.0 and 2.8, at room temperature, at a protein concentration of about 5×10$^{-6}$M with about 0.5 complex/antibody. Samples were withdrawn at certain time intervals and analyzed by HPLC (GF-250 column) for the dissociation of $^{153}$Sm or $^{177}$Lu activity from the protein. In general, the study was carried out for five days or until 90% of the radioisotopes have become dissociated. Results are expressed as the initial rate of loss of the radioisotope per day. The results demonstrated the superior stability of $^{153}$Sm(PA-DOTA), $^{177}$Lu(PA-DOTA, $^{153}$Sm(BA-DOTA), $^{153}$Sm(PA-DOTMA) and $^{153}$Sm(MeO-BA-DOTA), as compared with the standard [$^{153}$Sm(Bz-DTPA)] complex at acidic pH. Results are shown in the table below.

Figure 15:
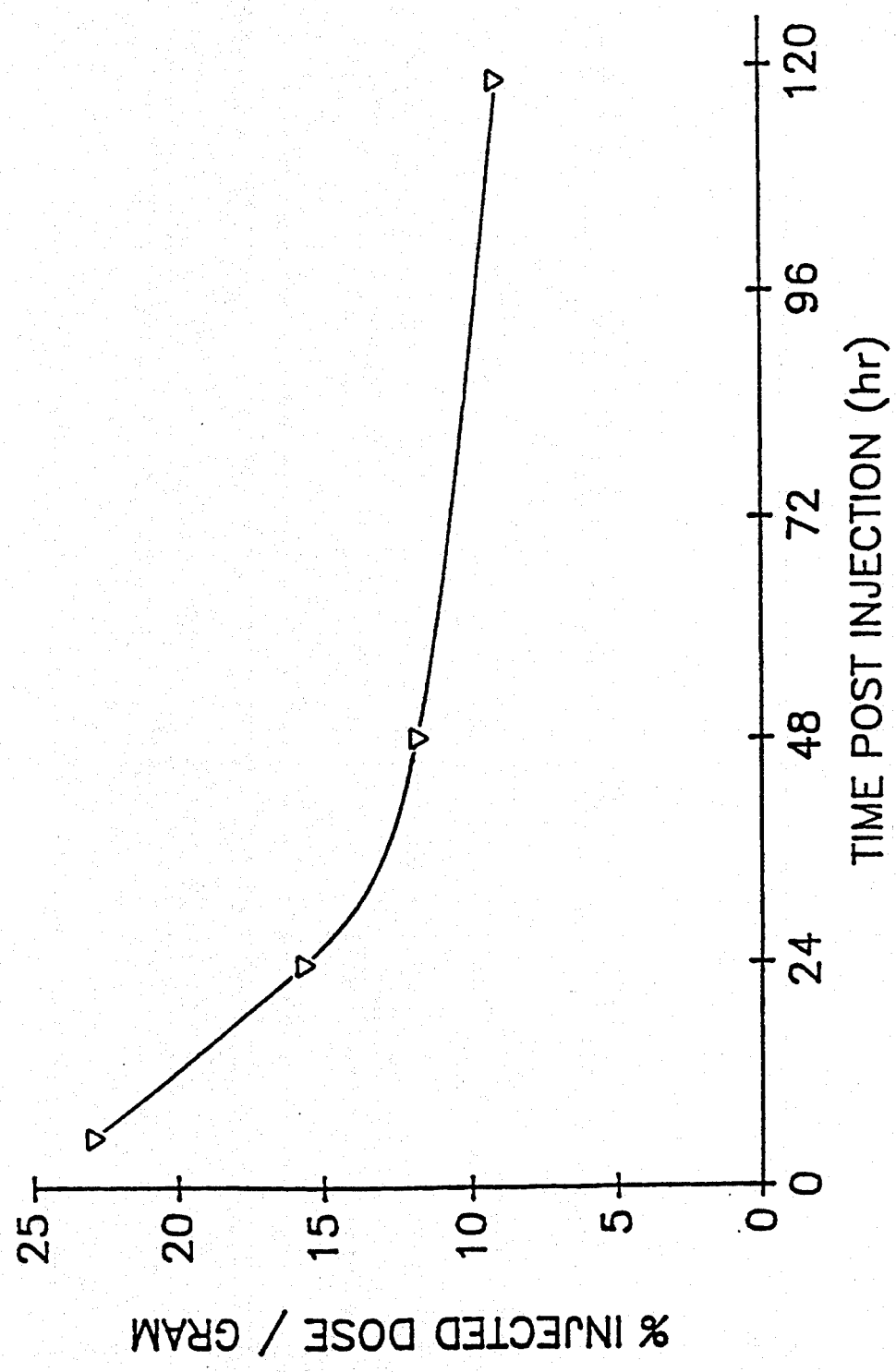
Figure 16:
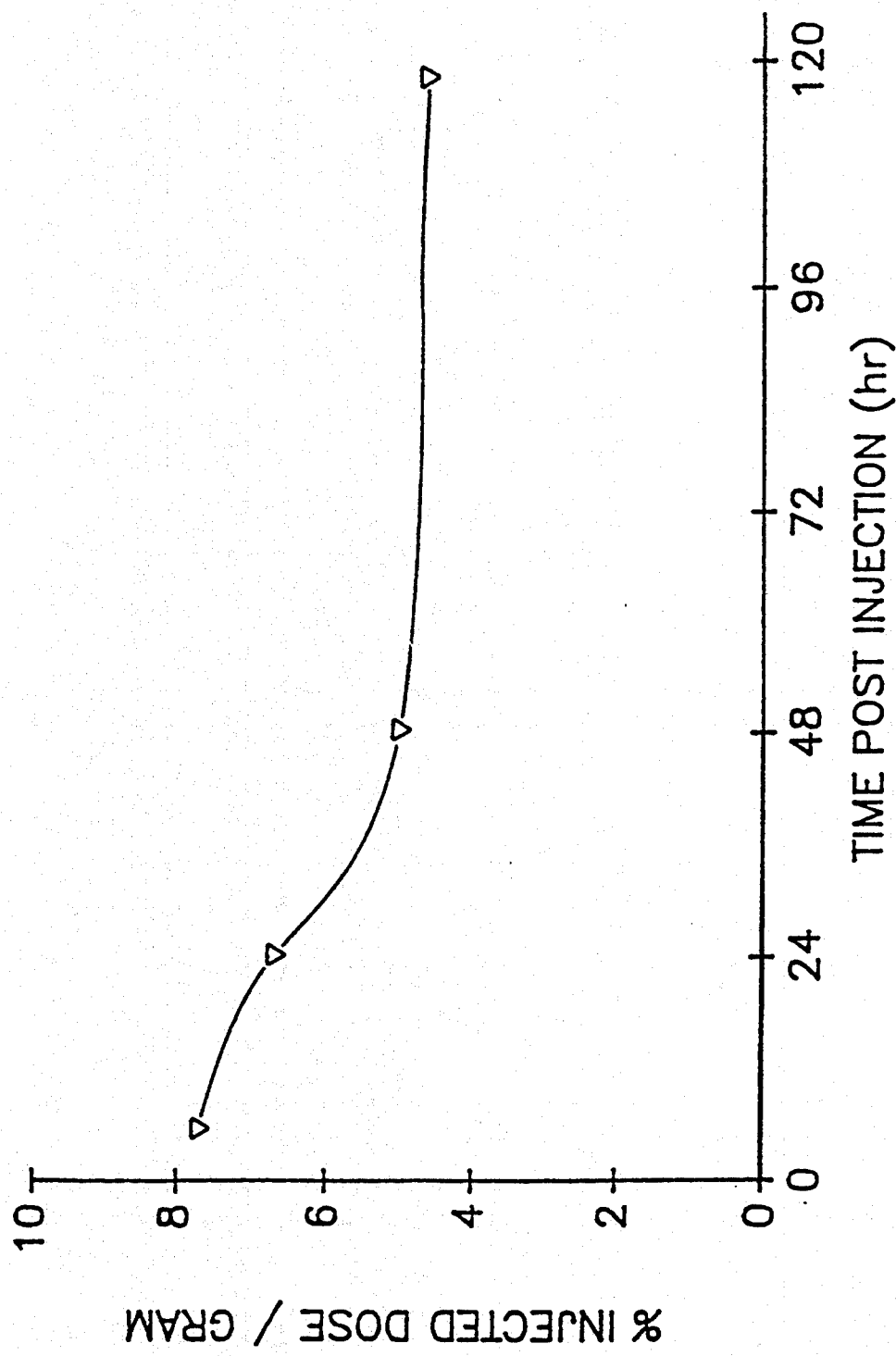
Figure 17:
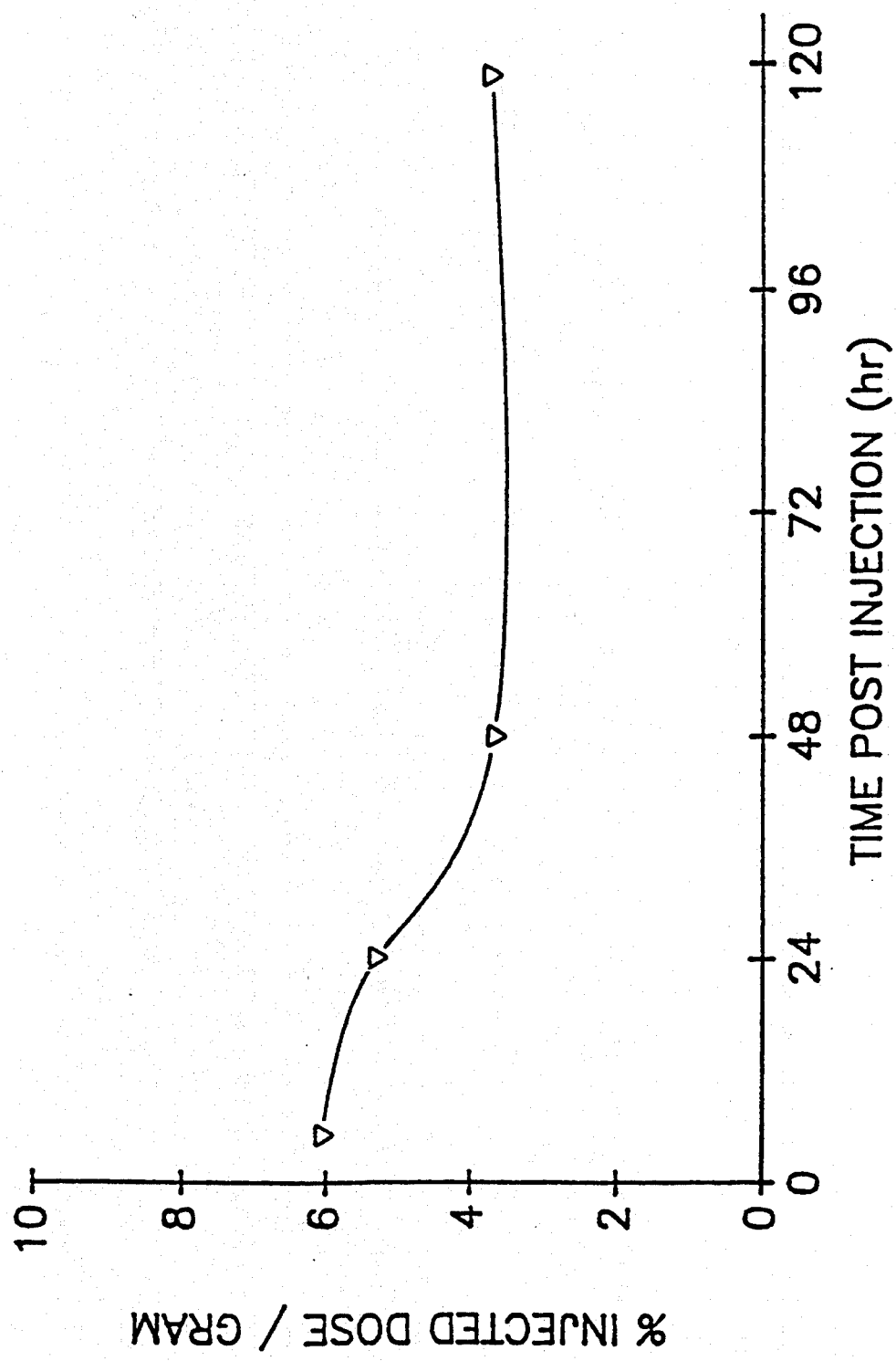
Figure 18:
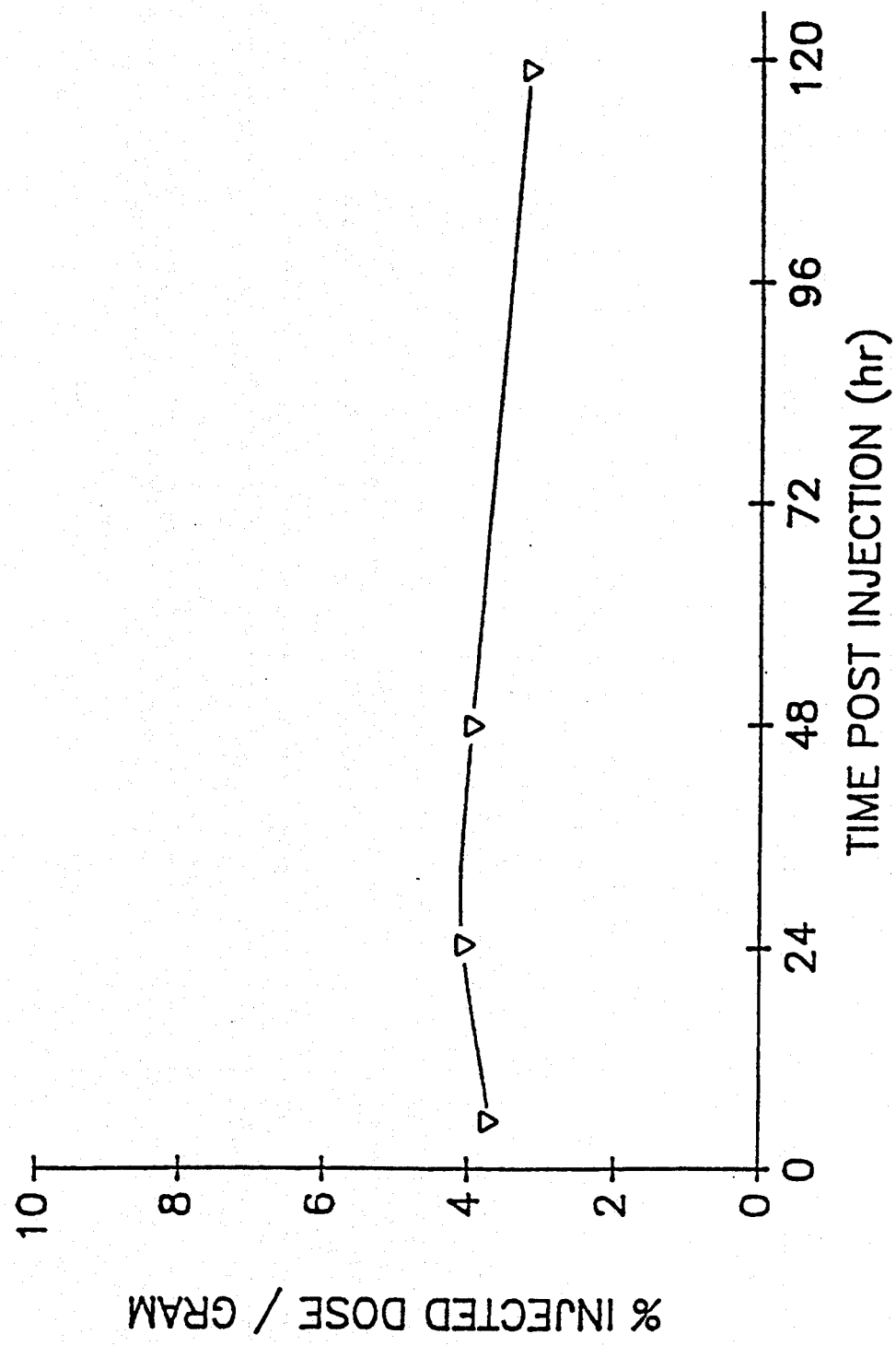
Figure 19:
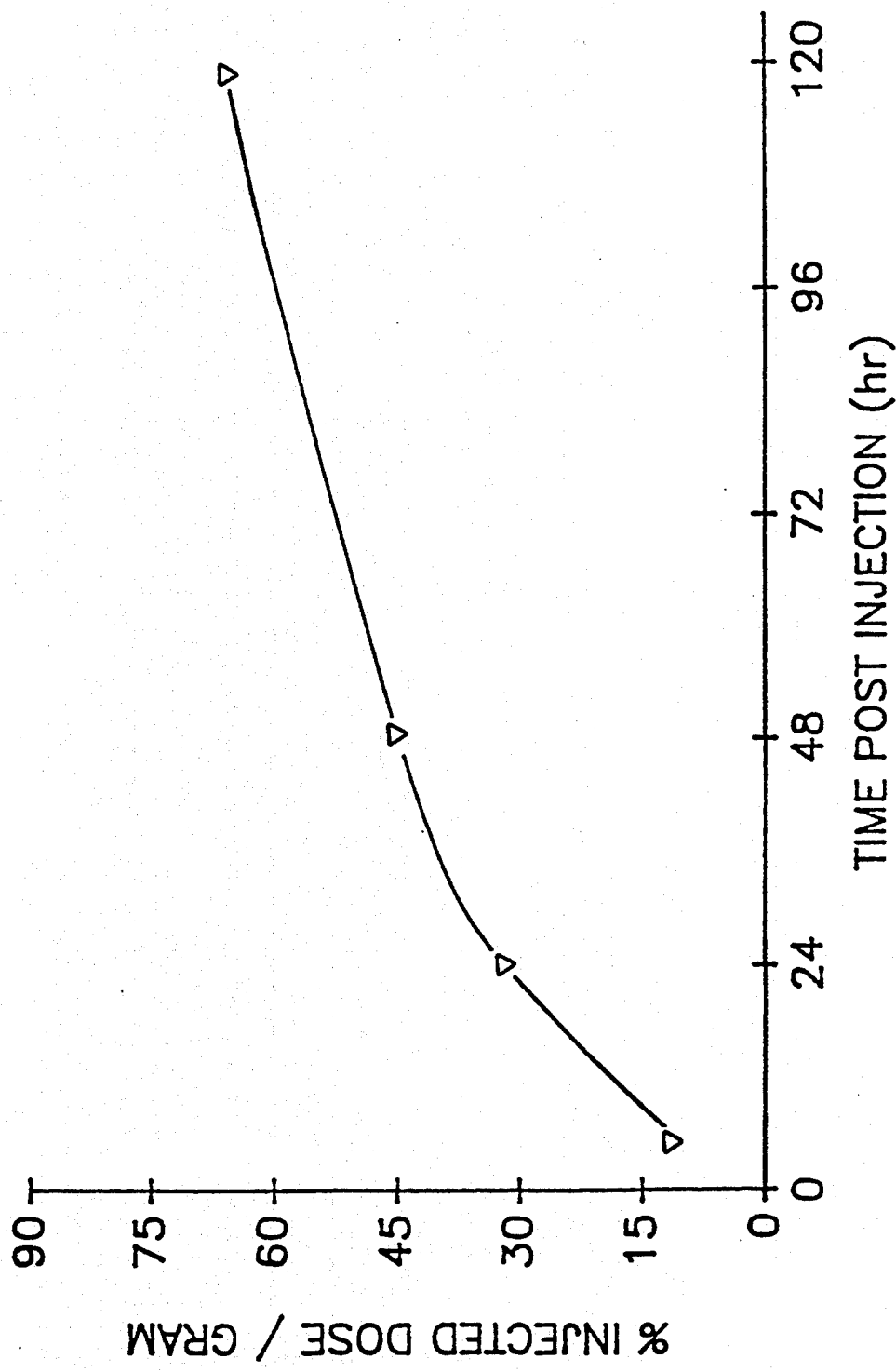
Figure 20:
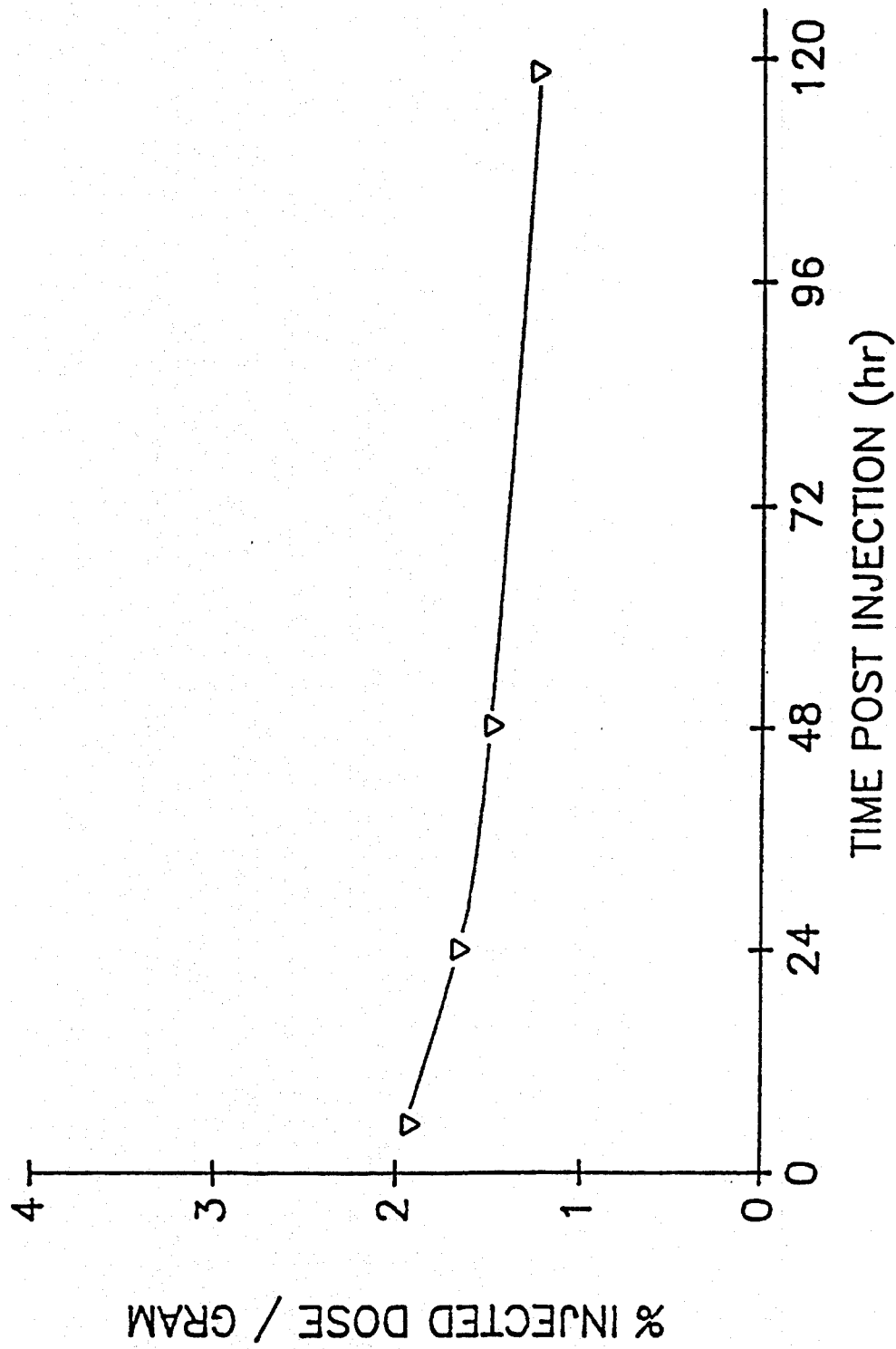
Figure 21:
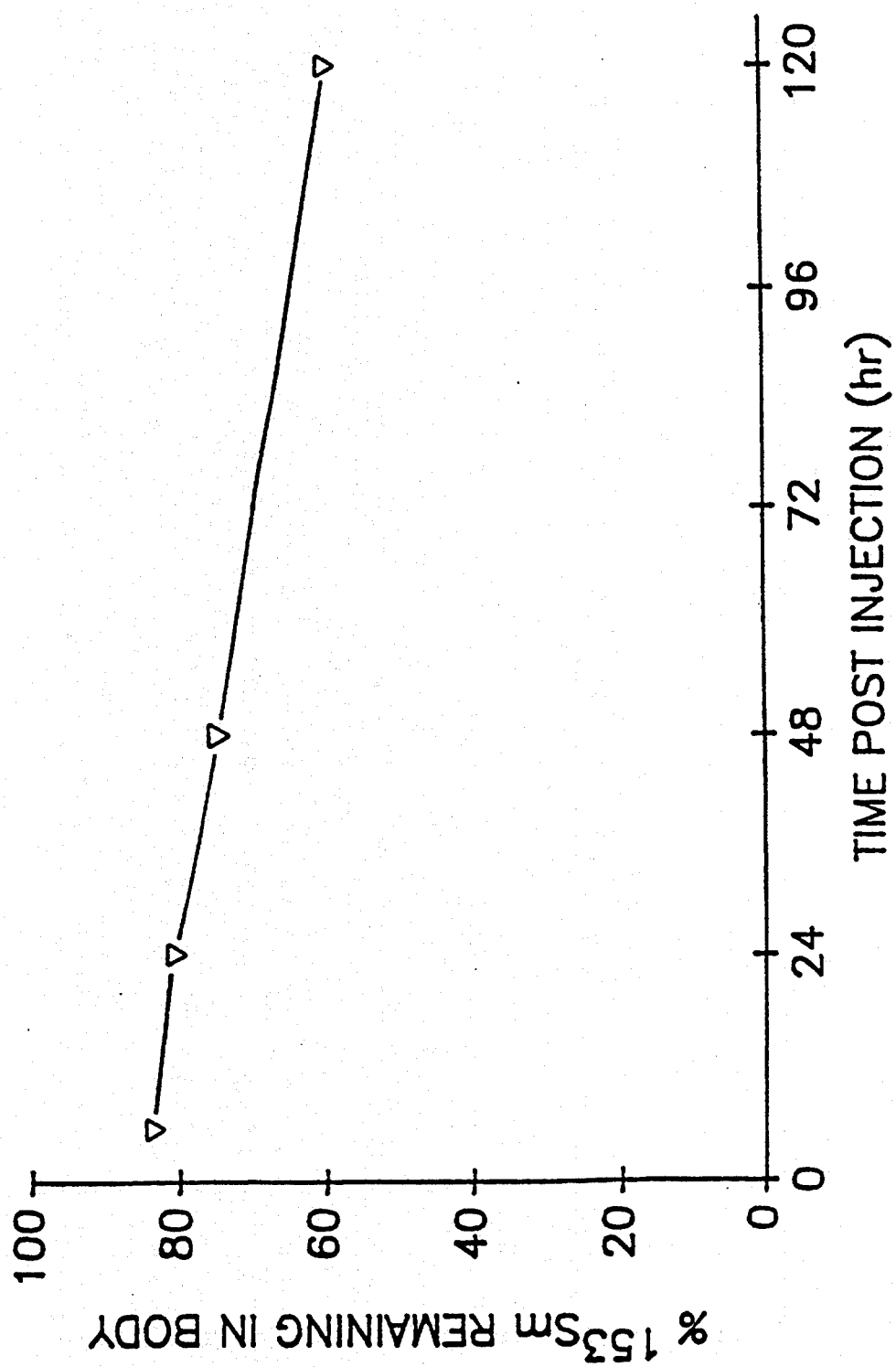
Figure 22:
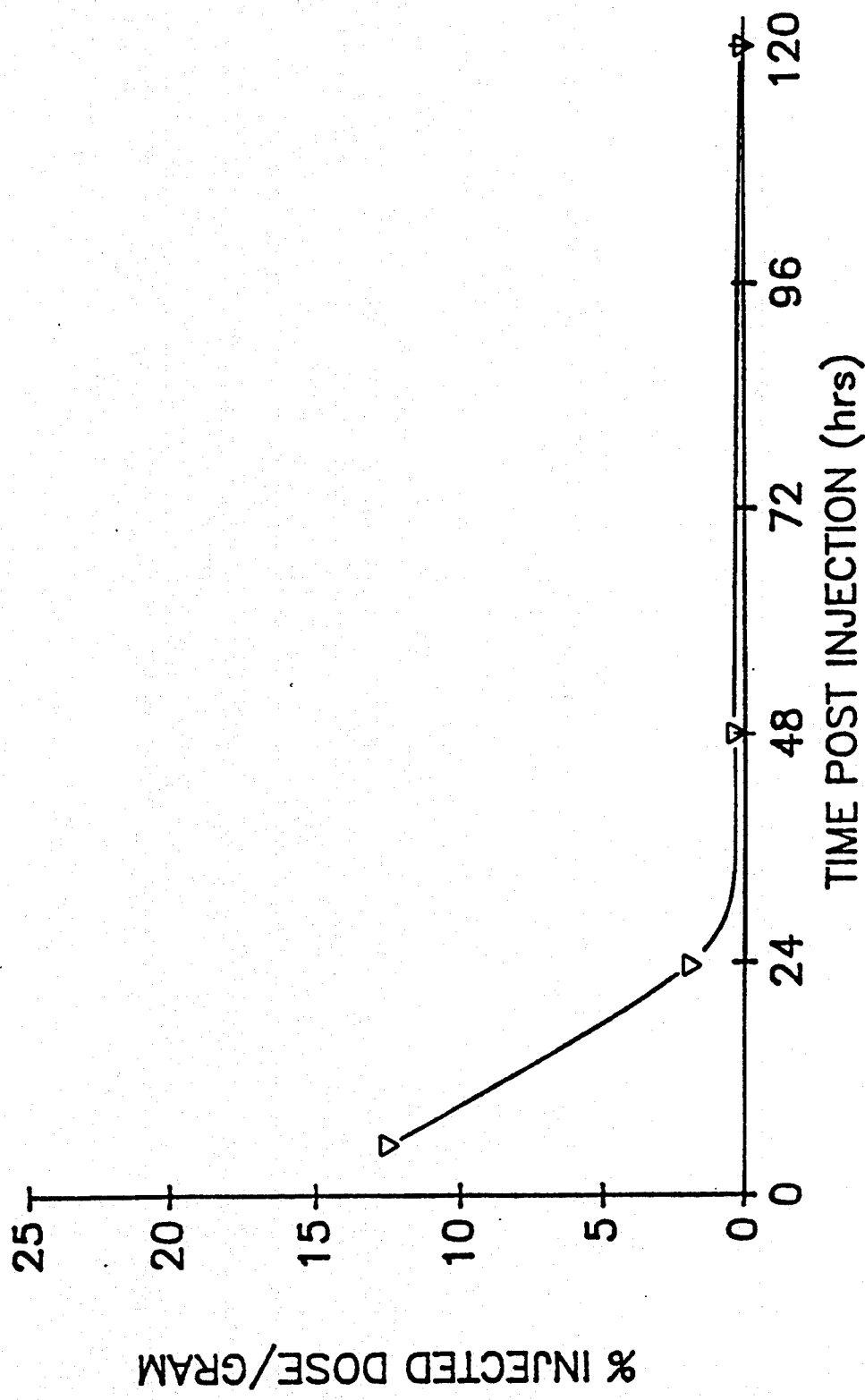
Figure 23:
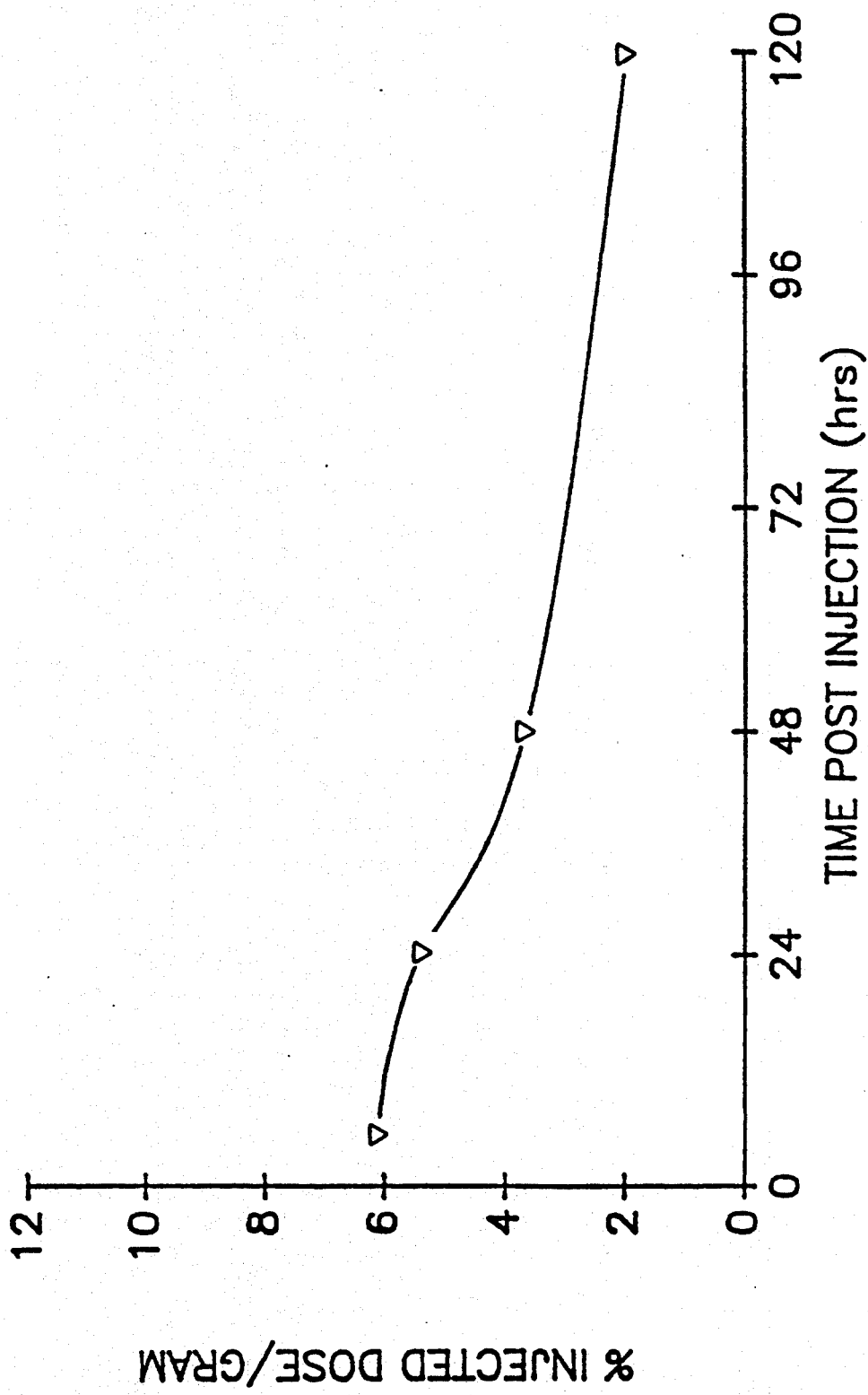
Figure 24:
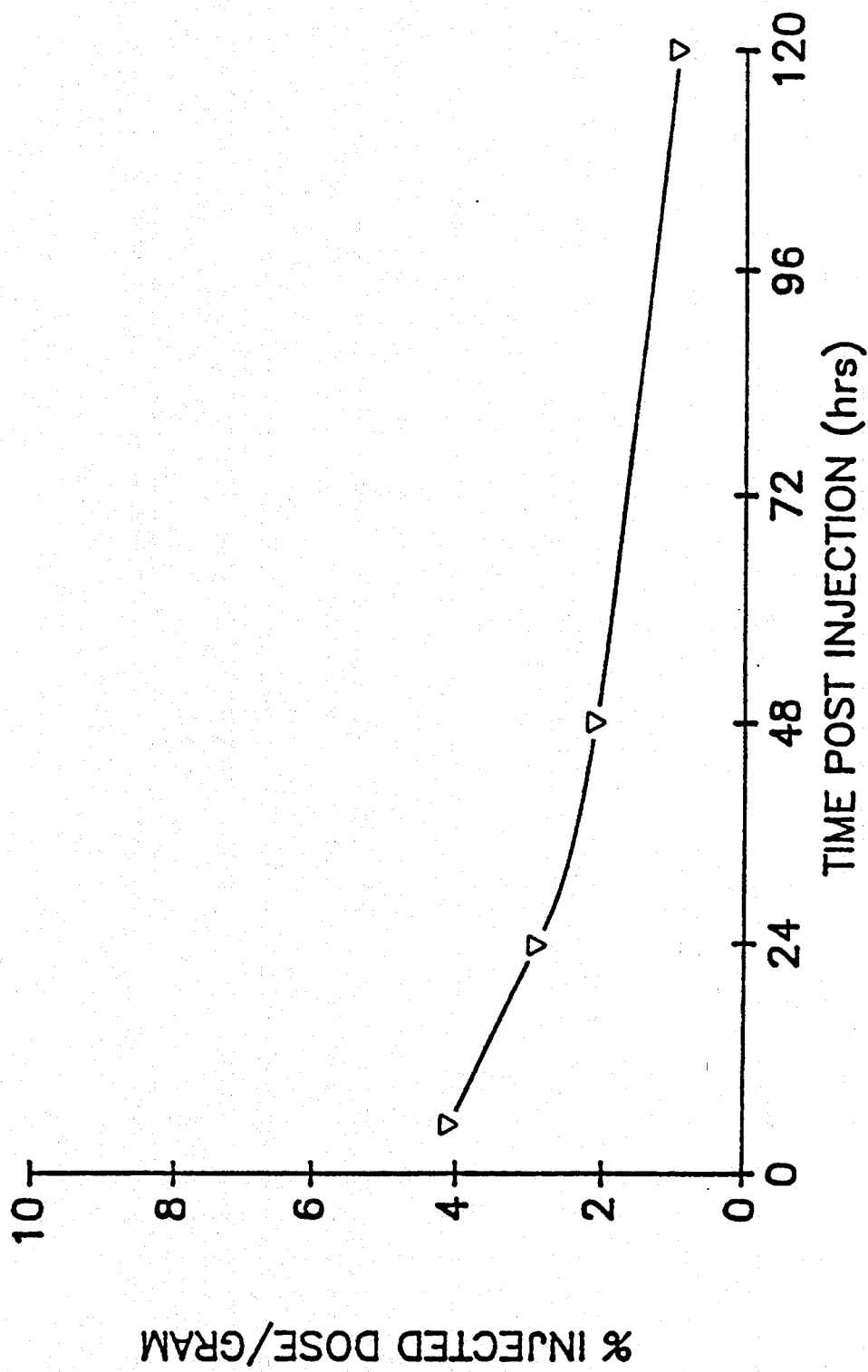
Figure 25:
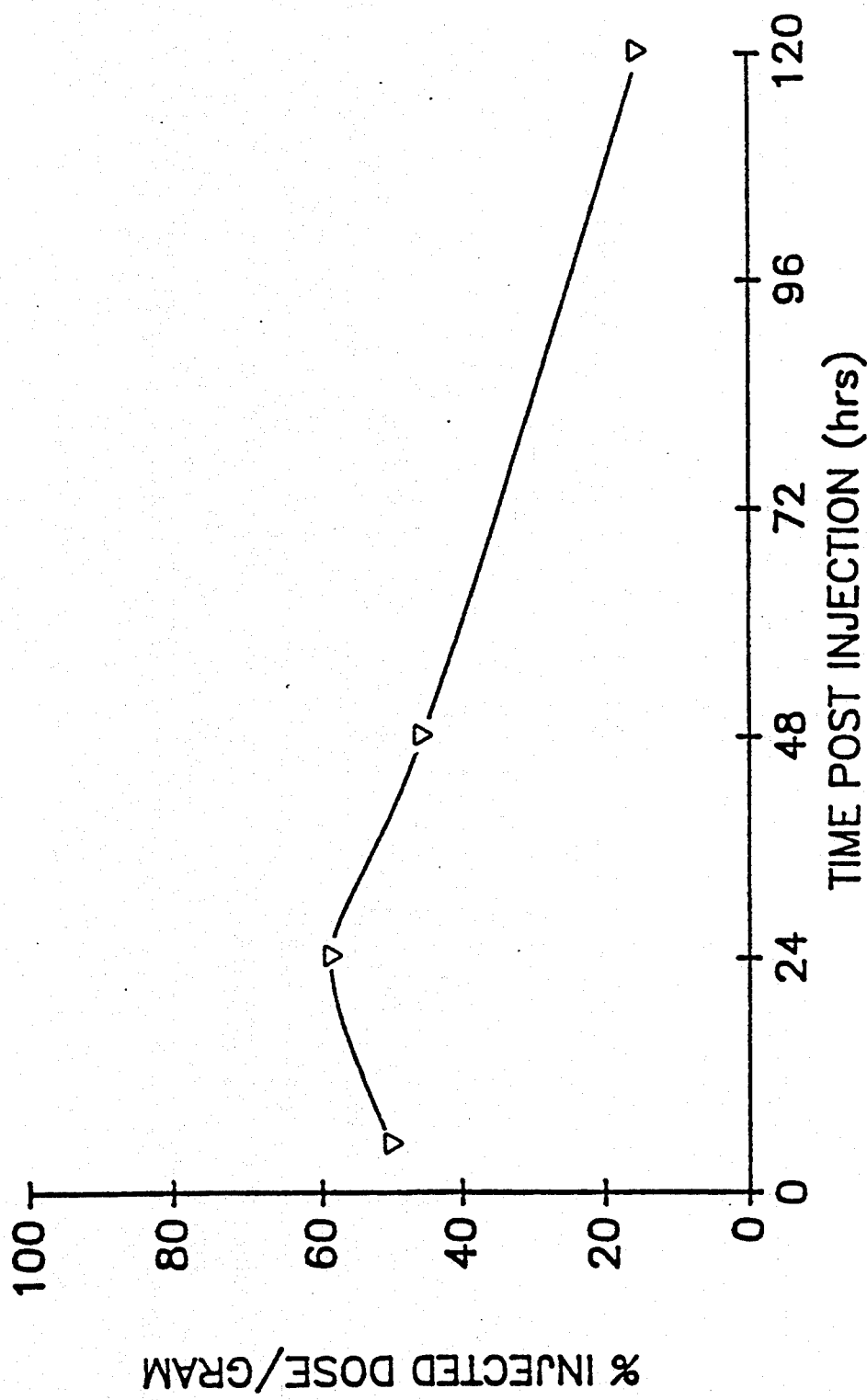
Figure 26:
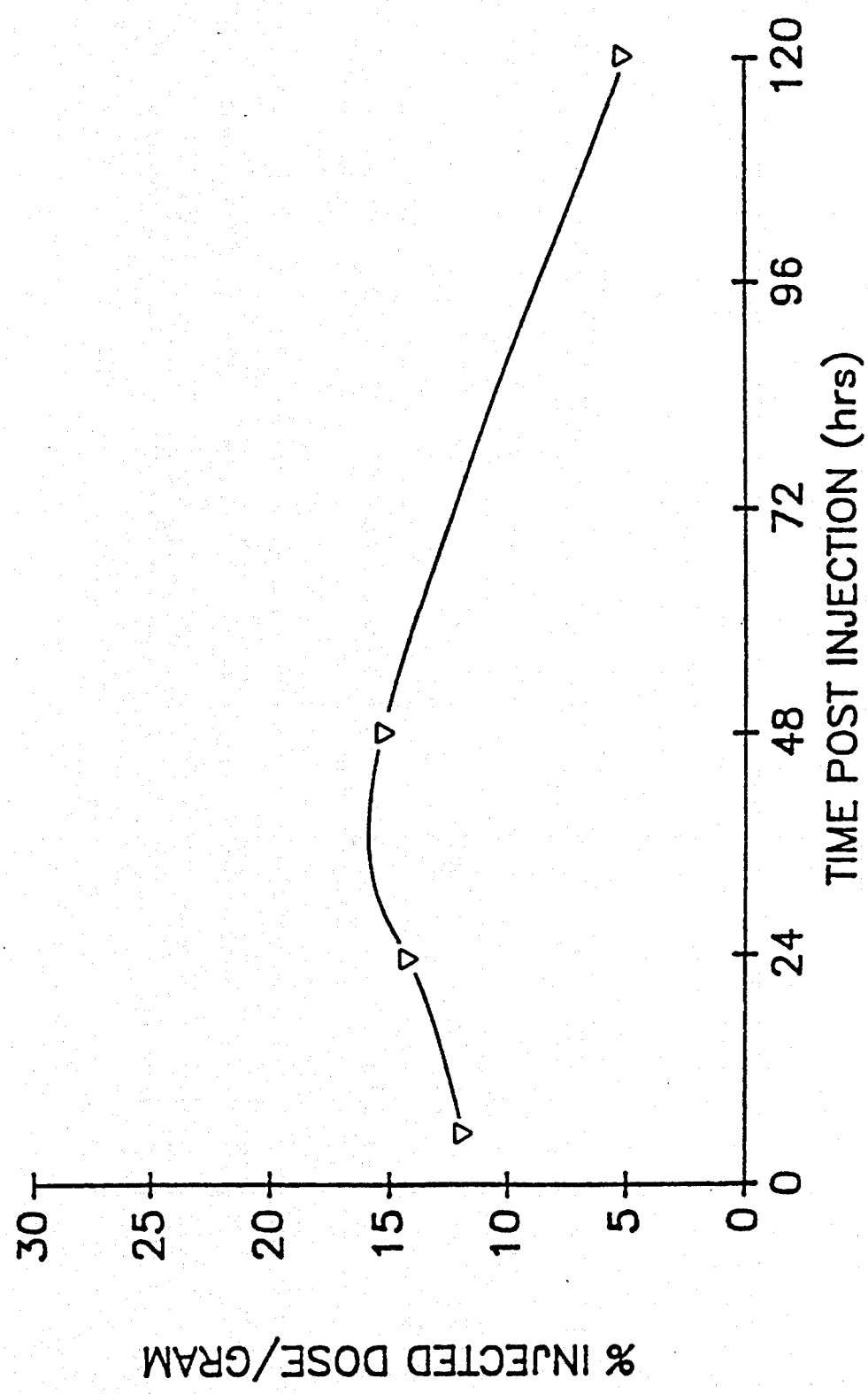
Figure 27:
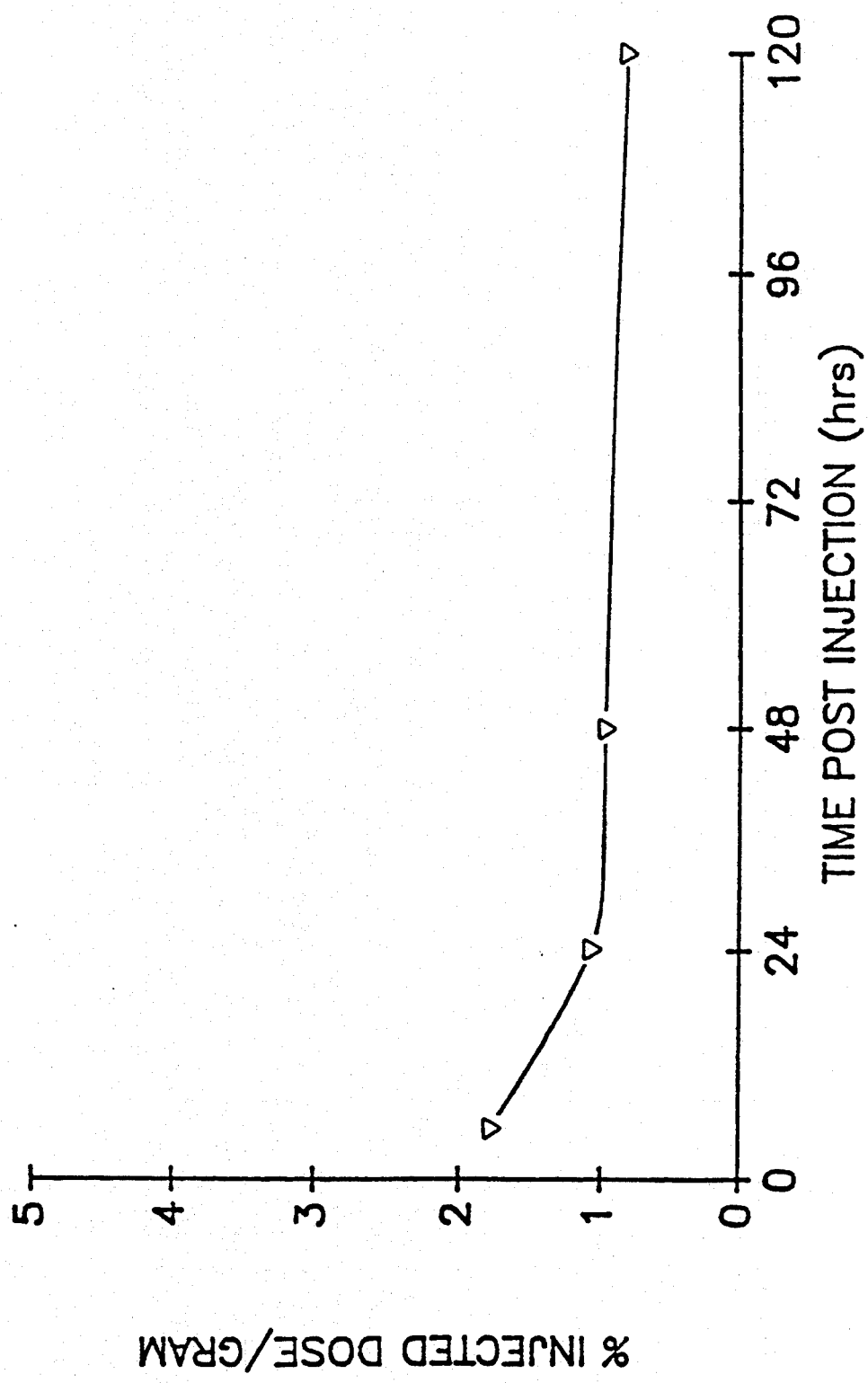
Figure 28:
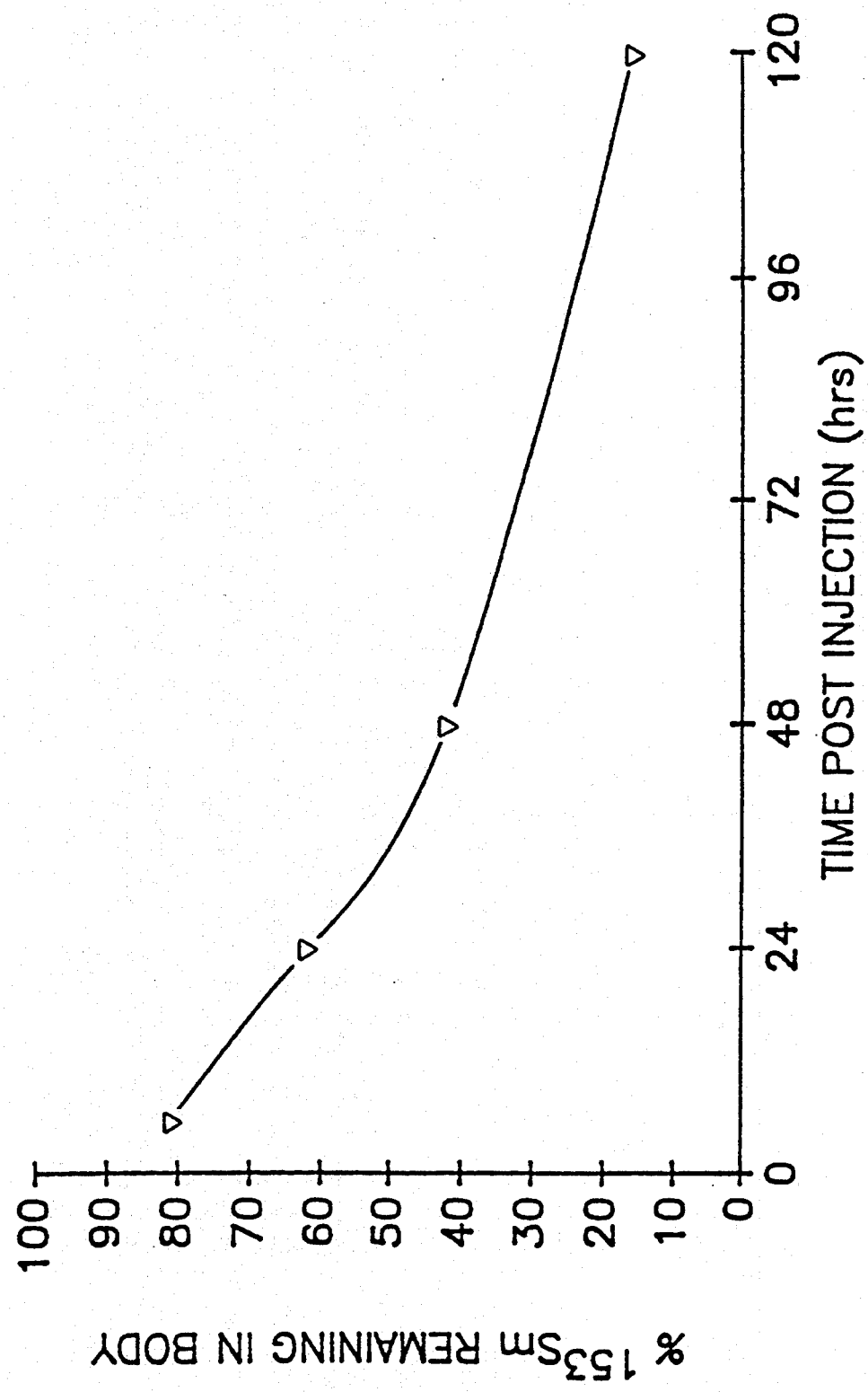
Figure 29:
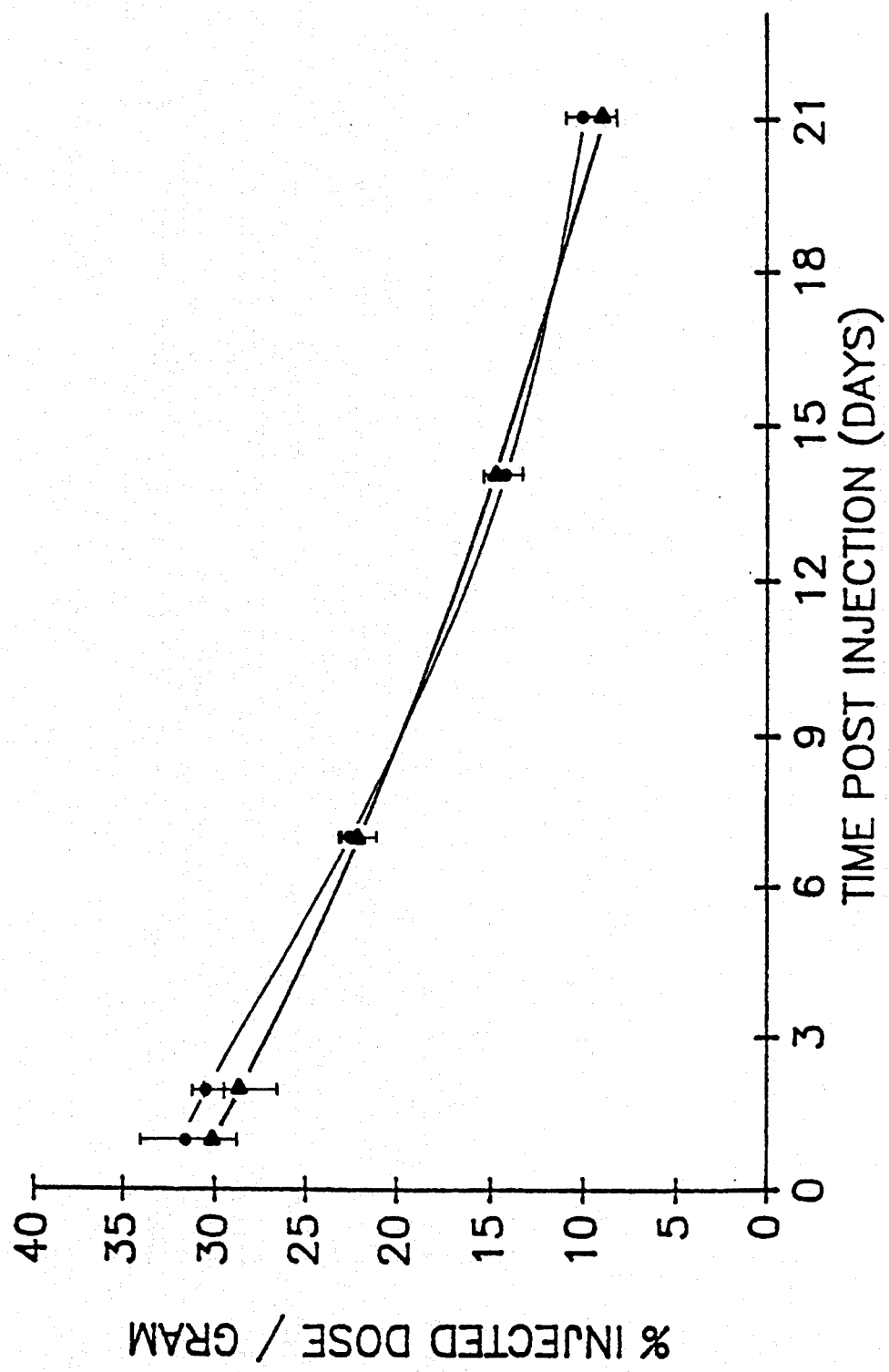
FIGS. 29–34 show the biodistribution of $^{177}$Lu as a conjugate containing $^{177}$Lu(PA-DOTMA) or $^{177}$Lu(PA-DOTA). The conjugate used CC$_{49}$-IgG as the antibody. The biodistribution was determined in (balb/C) mice bearing LS 174-T tumor.
Figure 30:
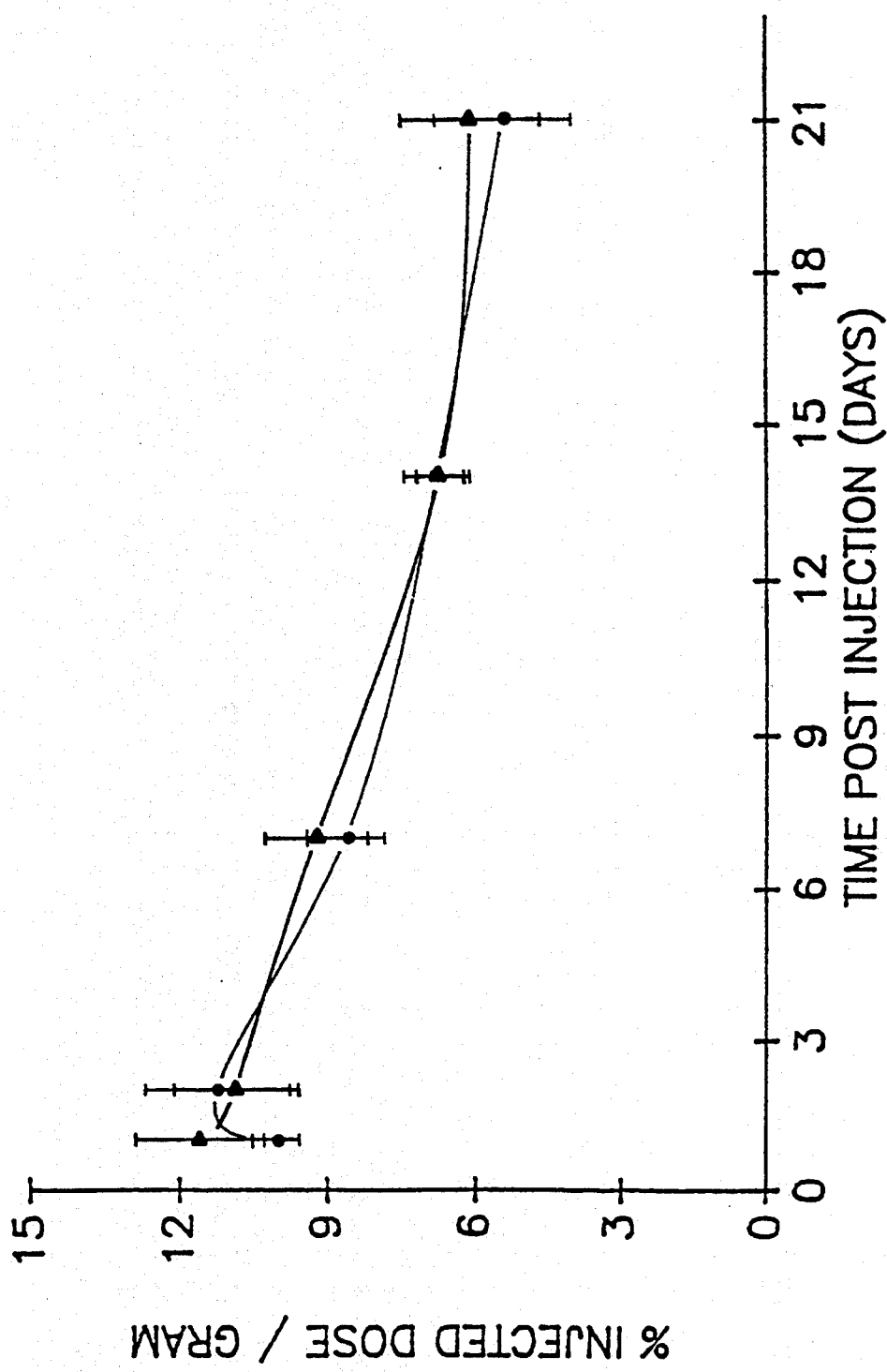
Figure 31:
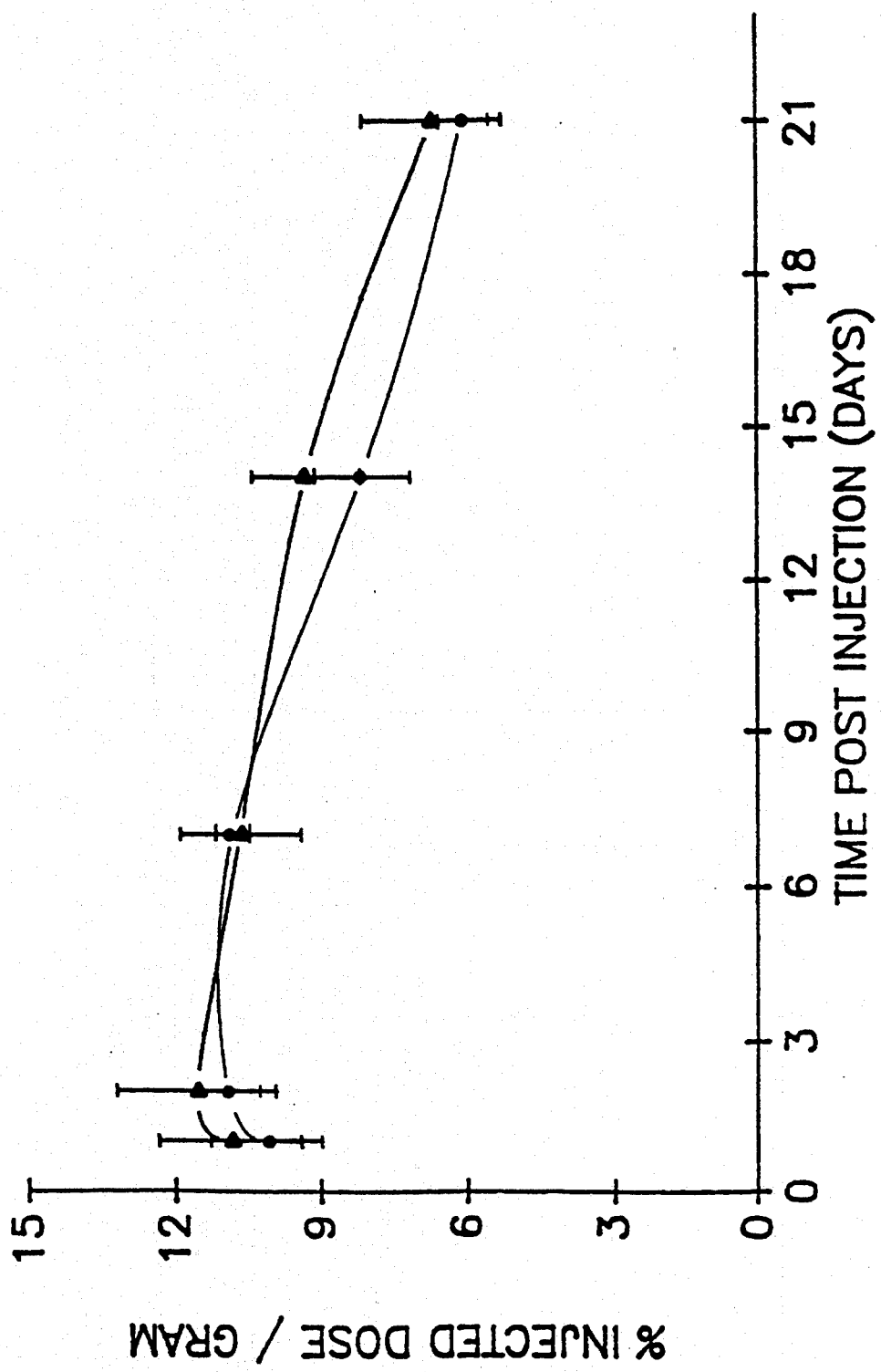
Figure 32:
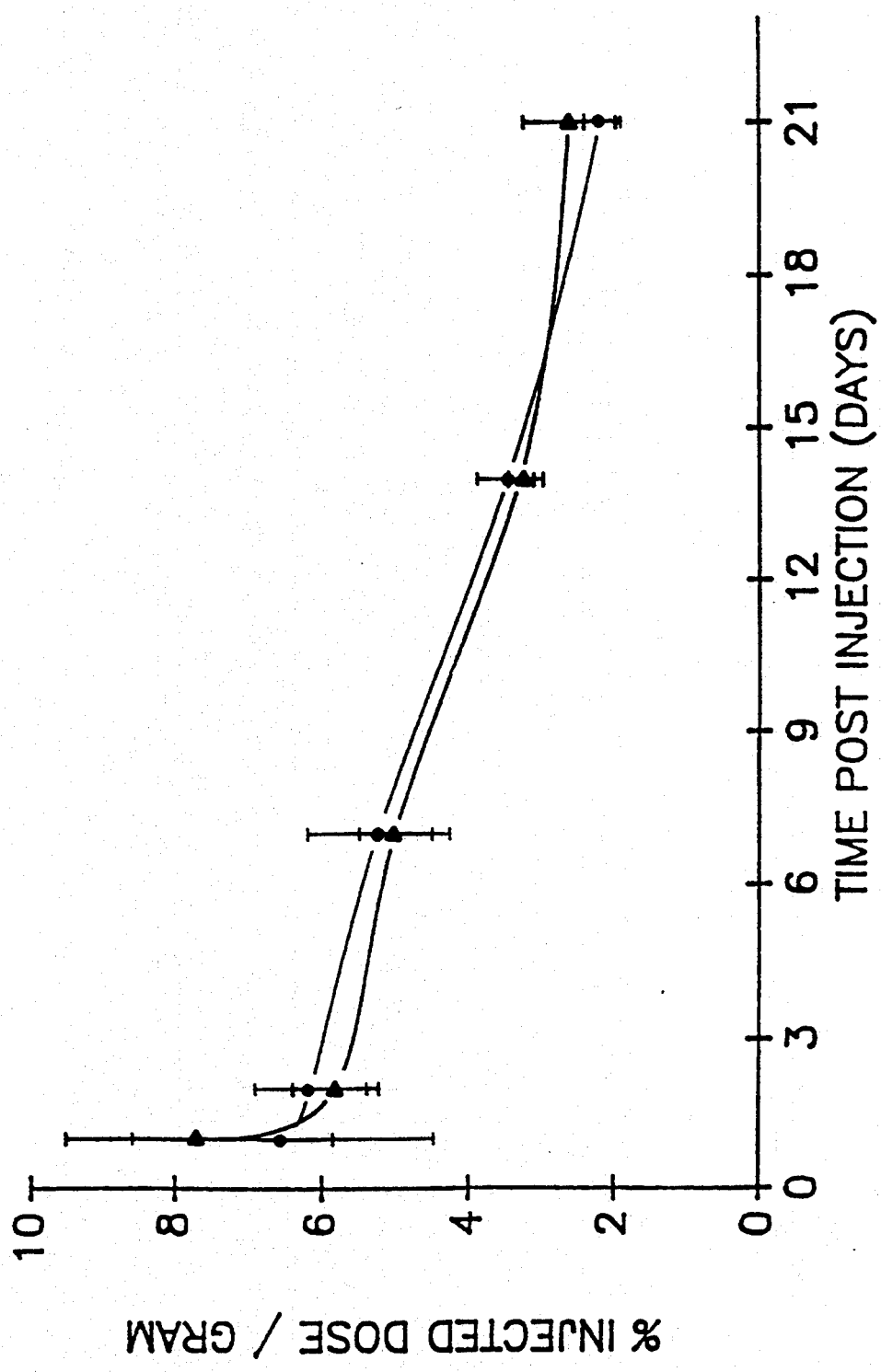
Figure 33:
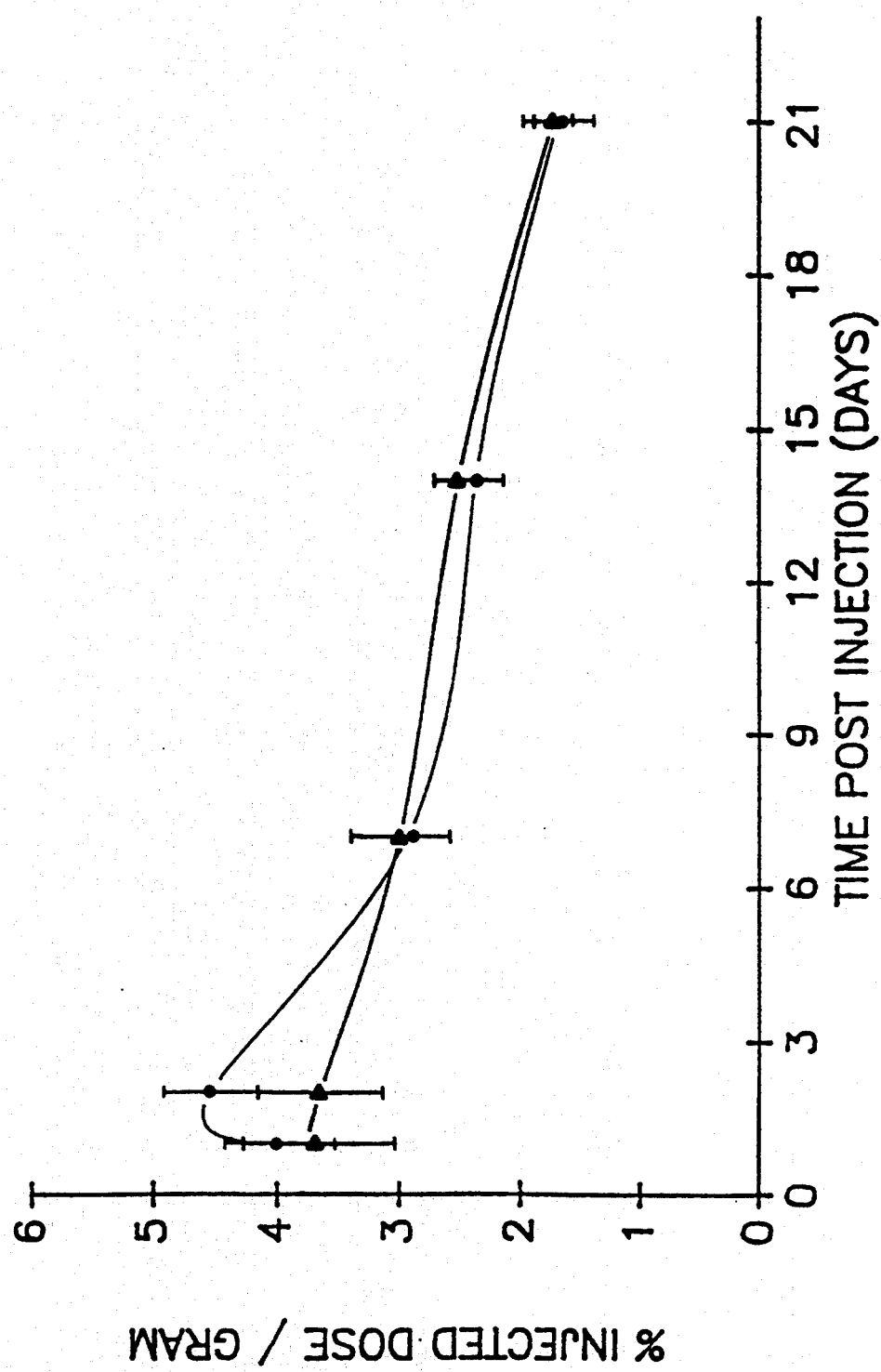
Figure 34:
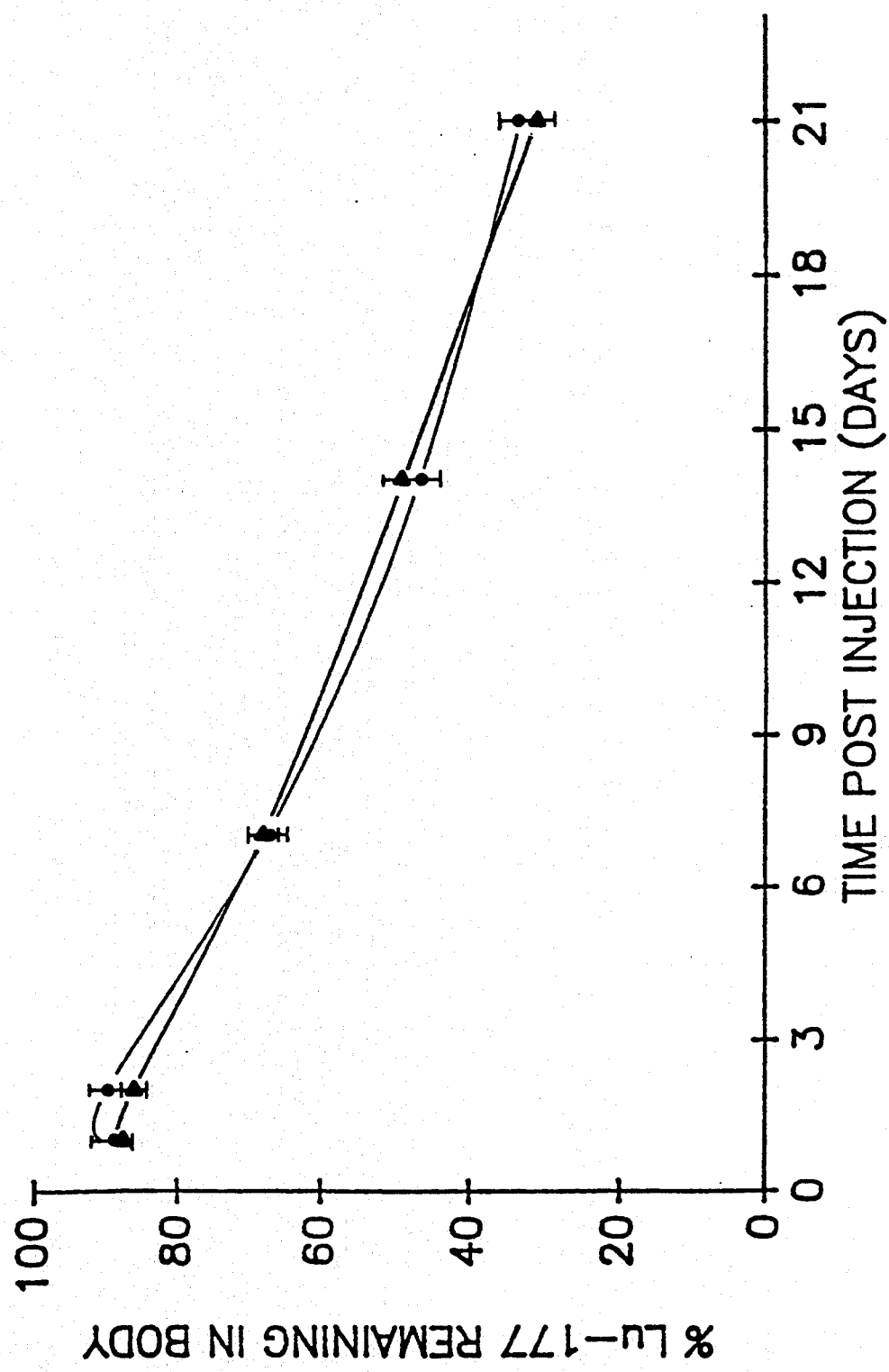

This greater stability of the complexes in vitro also correlates well with the more rapid clearance of Sm and $^{177}$Lu from the body and non-target tissue (e.g. kidney, liver); see FIGS. 1–34.

| BFC | Isotope | % Loss of Isotope/Day pH | | |
| --- | --- | --- | --- | --- |
| | | 6.0 | 4.0 | 2.8 |
| Bz—DTPA | $^{153}$Sm | <2 | 35 | 35 |
| PA—DOTA | $^{153}$Sm | <2 | <2 | <2 |
| BA—DOTA | $^{153}$Sm | <2 | <2 | <2 |
| PA—DOTA | $^{177}$Lu | <2 | <2 | <2 |
| MeOBA—DOTA | $^{153}$Sm | <2 | <2 | <2 |
| EA—DO3A | $^{153}$Sm | <2 | 90 | 95 |
| PA—DOTMA | $^{153}$Sm | <2 | <2 | — |

EXAMPLE XXI (A AND B)

In vivo localization of
α-(2-methoxy-5-aminophenyl)-1,4,7,10-tetraazacyclododecane-1,4,7,10-tetraacetic acid, samarium-153 complex labeled IgG and F(ab')$_2$;
[$^{153}$Sm(MeO-BA-DOTA)]-IgG and
[$^{153}$Sm(MeO-BA-DOTA)]-F(ab')$_2$ The titled compounds were prepared according to the procedures described in Examples V, VI, XII and XIII, and the in vivo studies were conducted by the procedures of Example XI. Results are shown in Tables VIA and VIB.

EXAMPLE XXII

Preparation of $^{153}$Sm(PA-DOTMA) Complex

To 100 microliters (μl) of $^{153}$Sm (0.3×10$^{-3}$M in 0.01N HCl; 5 mCi) were added 6 μl of PA-DOTMA (high R$_f$ diastereomer prepared by the procedure of Example 29; 5 mM in Milli-Q TM water), 20 μl of a MES buffer (1.0M, pH 6) and 1 μl of a HEPES buffer (0.5M, pH 8.7). This solution was mixed on a vortex mixer and the final pH of the mixture was about 6. After heating the mixture at 90° C. for 30 min, it was analyzed by HPLC on GF-250 column for degree of complexation, and yields of 90 percent or better, were generally obtained. Characterization of the $^{153}$Sm-PA-DOTMA complex was provided by comparison with the non-radioactive-Sm complex, which had been synthesized and characterized independently as described in Example 42.

EXAMPLE XXIII

Preparation of $^{153}$Sm(SCN-PA-DOTMA)

To the $^{153}$SmPA-DOTMA complex prepared in Example XXII and having been cooled for 20 min. at room temperature was added 10 μl of a 1 percent thiophosgene solution in 90 percent acetonitrile-water medium. The mixture was mixed vigorously on a vortex mixer, and allowed to stand at room temperature for between 5 to 20 min. The reaction took place instaneously as monitored by HPLC anaylsis. To purified the activated $^{153}$Sm complex, it was extracted 3 times (200 μl each) with chloroform and the aqueous layer was passed throught a PRP cartridge (PRP cartridge=Miniclean TM cartridge from Alltech Associates, Deerfield, Ill.) pretreated with 5 ml of methanol and 5 ml of a MES buffer (20 mM, pH 5.8). After being washed with 5 ml of the MES buffer and 5 ml of Milli-Q TM water, it was extracted with 900 μl of 90 percent acetontrile to recover approximately 90 percent of the $^{153}$Sm activity, with the first 100 μl discarded. The mixture was evaporated to dryness under reduced pressure at temperatures below 40° C., and the residue which contained mostly the title product was used for conjugation to the antibody.

EXAMPLE XXIV (A AND B)

Conjugation of $^{153}$Sm(SCN-PA-DOTMA) to IgG and F(ab')$_2$ CC$_{49}$

In general, the antibody was concentrated and exchanged into a carbonate buffer (pH 9.1 or 9.5, 50 mM) in a Centricon TM concentrator (30 K molecular weight cut off) to result in a protein concentration of $1.5 \times 10^{-4}$M or greater. To conjugate, a small volume of the carbonate buffer, that which is required to bring the final protein concentration to $1.5 \times 10^{-4}$M, is added to the isothiocyanato derivative of $^{153}$Sm(PA-DOTMA) (prepared in Example XXIII), followed by the concentrated antibody, of equimolar to the BFC-$^{153}$Sm complex. It was mixed on a vortex mixer and allowed to react at room temperature for 1 hour or until 40 to 50 percent of $^{153}$Sm become bound to the antibody, as shown by HPLC analysis on a GF-250 column. The labeled antibody was isolated by two consecutive centrifugal gel filtration on Sephadex TM G-25 columns (2.2 ml). The homgeneity, integrity and immunoreactivity of the labeled antibody was analyzed by HPLC analysis and standard biochemical techniques described previously.

EXAMPLE XXV (A AND B)

Biodistribution Studies of $^{153}$Sm(PA-DOTMA) labeled IgG and F(ab')$_2$ CC$_{49}$ The studies were conducted in the similar fashion as described in Example XI. Results are shown in Tables VIIA and VIIB. See FIGS. 15-28.

EXAMPLE XXVI

Preparation of $^{177}$Lu (PA-DOTMA) Complex

To 30 μl of $^{177}$Lu ($6 \times 10^{-3}$M in 1.1N HCl; 4 mCi) was added 36 μl of PA-DOTMA (prepared by the procedure of Example 29); 5 mM solution in milli-Q TM water). The solution was mixed on a vortex mixer, and 115 μl of a MES buffer (1.0M, pH 6.0) was added to neutralize the solution to about pH 5.5 to 6. This was heated at 90° C. for 30 minutes to result in better than 90% chelation. The mixture was passed through a PRP cartridge pretreated with 5 ml of methanol and 5 ml of a MES buffer (20 mM, pH 5.8). It was washed with 5 ml of milli-Q TM waste. The complex extracted in 1000 μl of 90% acetonitrile accounted for 78% of the starting $^{177}$Lu activity (discarding the first 100 μl of the extract).

EXAMPLE XXVII

Preparation of $^{177}$Lu(SCN-PA-DOTMA)

To the $^{177}$Lu(PA-DOTMA) complex in 90% acetonitrile obtained in Example XXVI was added 6 μl of a 10% thiophosgen in 90% acetonitrile. This solution was mixed on a vortex mixer, and after 20 minutes, analyzed for the formation of the isothiocyanate derivative by HPLC. The reaction is, in general, quantitative. Removal of the solvent and the excess thiophosgene was accomplished by evaporation under reduced pressure at temperatures below 40° C. for 1 to 2 hours. The residue was used for conjugation with the antibody.

EXAMPLE XXVIII

Conjugation of $^{177}$Lu(PA-DOTMA) to IgG CC49

The antibody IgG CC49 in a carbonate buffer (50 mM, pH 9.1) was mixed with an equimolar quantity of the isothiocyanato derivative (prepared by the procedure of from Example XXVII) in the same buffer. The reaction was continued for 70 min at an antibody concentration of $1.5 \times 10^{-4}$M, and the labeled antibody was isolated and characterized according to procedures described in Example IX.

EXAMPLE XXIX

Long Term Biodistribution Studies of $^{177}$Lu(PA-DOTMA) and $^{177}$Lu(PA-DOTA)Labeled IgG CC49

The long term animal test was conducted with the $^{177}$Lu labeled antibody, taking advantage of its long half-life time (161 hours). It was carried out in Balb/c mice over a three week period, according to protocols described in Example XI. Results are shown in Table VIIIA. See FIGS. 29-34.

In the Figures, which plot the data from the following tables, the symbols used were:

| Conjugates | Symbol | Table | FIGS. | Bio. Example |
|---|---|---|---|---|
| [$^{153}$Sm(EA—DO3A)]—IgG—CC-49 | Δ | IA | 1-7 | IX |
| [$^{153}$Sm(EA—DO3A)]—F(ab'2)—CC-49 | Δ | IB | 8-14 | X |

| Conjugates | Symbol | Table | FIGS. | Bio. Example |
|---|---|---|---|---|
| [$^{153}$Sm(Bz—DTPA)]—IgG—CC-49 | ○ | IC | 1–7 | ZA |
| [$^{153}$Sm(Bz—DTPA)]—F(ab'2)—CC-49 | ○ | ID | 8–14 | ZA |
| [$^{153}$Sm(PA—DOTA)]—IgG—CC-49 | □ | IIA | 1–7 | XII |
| [$^{153}$Sm(PA—DOTA)]—F(ab'2)—CC-49 | □ | IIB | 8–14 | XIII |
| [$^{153}$Sm(BA—DOTA)]—IgG—CC-49 | | IIIA | 1–7 | XV |
| [$^{153}$Sm(BA—DOTA)]—F(ab'2)—CC-49 | | IIIB | 8–14 | XVI |
| [$^{153}$Sm(PA—DOTMA)]—IgG—CC-49 | ▽ | VIIA | 15–21 | XXIV |
| [$^{153}$Sm(PA—DOTMA)]—F(ab'2)—CC-49 | ▽ | VIIB | 22–28 | XXV |
| [$^{177}$Lu(PA—DOTMA)]—IgG—CC-49 | | VIIIA | 29–34 | XXIX |
| [$^{177}$Lu(PA—DOTA)]—IgG—CC-49 | | VIIIA | 29–34 | XXIX |

In the accompanying Figures the data represents the following:

| FIGURE | ORGAN | TITLE |
|---|---|---|
| 1 | Blood | Biodistribution of $^{153}$Sm—BFC* |
| 2 | Liver | Biodistribution of $^{153}$Sm—BFC* |
| 3 | Spleen | Biodistribution of $^{153}$Sm—BFC* |
| 4 | Kidney | Biodistribution of $^{153}$Sm—BFC* |
| 5 | Tumor | Biodistribution of $^{153}$Sm—BFC* |
| 6 | Femur | Biodistribution of $^{153}$Sm—BFC* |
| 7 | Whole Body Retention | Biodistribution of $^{153}$Sm—BFC* |
| 8 | Blood | Biodistribution of $^{153}$Sm—BFC* |
| 9 | Liver | Biodistribution of $^{153}$Sm—BFC* |
| 10 | Kidney | Biodistribution of $^{153}$Sm—BFC* |
| 11 | Spleen | Biodistribution of $^{153}$Sm—BFC* |
| 12 | Tumor | Biodistribution of $^{153}$Sm—BFC* |
| 13 | Femur | Biodistribution of $^{153}$Sm—BFC* |
| 14 | Whole Body Retention | Biodistribution of $^{153}$Sm—BFC* |
| 15 | Blood | Biodistribution of $^{153}$Sm—BFC* |
| 16 | Liver | Biodistribution of $^{153}$Sm—BFC* |
| 17 | Spleen | Biodistribution of $^{153}$Sm—BFC* |
| 18 | Kidney | Biodistribution of $^{153}$Sm—BFC* |
| 19 | Tumor | Biodistribution of $^{153}$Sm—BFC* |
| 20 | Femur | Biodistribution of $^{153}$Sm—BFC* |
| 21 | Whole Body Retention | Biodistribution of $^{153}$Sm—BFC* |
| 22 | Blood | Biodistribution of $^{153}$Sm—BFC** |
| 23 | Liver | Biodistribution of $^{153}$Sm—BFC** |
| 24 | Spleen | Biodistribution of $^{153}$Sm—BFC** |
| 25 | Kidney | Biodistribution of $^{153}$Sm—BFC** |
| 26 | Tumor | Biodistribution of $^{153}$Sm—BFC** |
| 27 | Femur | Biodistribution of $^{153}$Sm—BFC** |
| 28 | Whole Body Retention | Biodistribution of $^{153}$Sm—BFC** |
| 29 | Blood | Biodistribution of $^{177}$Lu—BFC*** |
| 30 | Liver | Biodistribution of $^{177}$Lu—BFC*** |
| 31 | Spleen | Biodistribution of $^{177}$Lu—BFC*** |
| 32 | Kidney | Biodistribution of $^{177}$Lu—BFC*** |
| 33 | Femur | Biodistribution of $^{177}$Lu—BFC*** |
| 34 | Whole Body Retention | Biodistribution of $^{177}$Lu—BFC*** |

*CC49-IgG in nude mice bearing LS174-T tumor
**CC49-F(ab')$_2$ in nude mice bearing LS174-T tumor
***CC49-IgG in balb/c mice

TABLE IA

BIODISTRIBUTION OF $^{153}$Sm INJECTED AS
[$^{153}$Sm(EA—DO3A)]—IgG—CC-49
% INJECTED DOSE/GRAM
(n = 5)

| Organ | 5 hr | | 24 hr | | 48 hr | | 120 hr | |
|---|---|---|---|---|---|---|---|---|
| | AVG | STD | AVG | STD | AVG | STD | AVG | STD |
| Blood | 23.08 | 2.36 | 17.25 | 2.40 | 11.32 | *1.06 | 5.78 | *1.69 |
| Liver | 6.95 | 1.28 | 6.58 | 0.56 | 6.58 | 0.62 | 7.62 | 0.98 |
| Spleen | 5.17 | 0.59 | 5.06 | 0.96 | 4.62 | 0.72 | 4.92 | 1.72 |
| Kidney | 4.59 | 0.68 | 4.01 | 0.53 | 3.74 | 0.76 | 3.20 | 0.59 |
| Tumor | 11.44 | 4.13 | 27.19 | 2.12 | 53.01 | 9.10 | 59.01 | 13.23 |
| Femur | — | — | 2.58 | 0.52 | 2.78 | 0.20 | 4.22 | 0.17 |
| Tumor Wt. g | 0.16 | 0.09 | 0.20 | 0.09 | 0.30 | 0.17 | 0.52 | 0.34 |

*n = 4

TABLE IB

BIODISTRIBUTION OF $^{153}$Sm INJECTED AS [$^{153}$Sm(EA—DO3A)]—F(ab')$_2$
CC-49 % INJECTED DOSE/GRAM
(n = 5)

| Organ | 5 hr | | 24 hr | | 48 hr | | 120 hr | |
|---|---|---|---|---|---|---|---|---|
| | AVG | STD | AVG | STD | AVG | STD | AVG | STD |
| Blood | 13.36 | 0.97 | 1.52 | 0.42 | 0.20 | 0.06 | 0.05 | 0.01 |
| Liver | 7.13 | 0.65 | 8.69 | 1.3 | 8.08 | 0.8 | 8.11 | 0.92 |
| Spleen | 5.94 | 1.24 | 4.96 | 1.27 | 4.81 | 0.99 | 5.08 | 1.43 |
| Kidney | 41.60 | 5.60 | 64.32 | 7.88 | 64.12 | *12.59 | 37.63 | 6.57 |
| Tumor | 12.95 | 1.73 | 16.84 | 3.71 | 11.50 | 4.56 | 5.53 | 1.46 |
| Femur | 2.74 | 0.65 | 2.45 | 0.26 | 3.41 | 0.75 | 4.99 | 0.29 |
| Tumor Wt. g | 0.25 | 0.20 | 0.34 | 0.25 | 0.28 | 0.14 | 0.44 | 0.27 |

*n = 4

TABLE IC

BIODISTRIBUTION OF $^{153}$Sm INJECTED AS [$^{153}$Sm(Bz—DTPA)]—IgG—CC-49
% INJECTED DOSE/GRAM
(n = 10)

| Organ | 5 hr AVG | 5 hr STD | 24 hr AVG | 24 hr STD | 48 hr AVG | 48 hr STD | 120 hr AVG | 120 hr STD |
|---|---|---|---|---|---|---|---|---|
| Blood | 24.97 | 3.07 | 16.05 | 2.45 | 12.81 | 2.69 | 5.84 | 1.76 |
| Liver | 7.74 | 1.35 | 6.01 | 0.95 | 5.68 | 1.07 | 5.43 | 1.45 |
| Spleen | 5.69 | 1.04 | 4.86 | 1.36 | 4.72 | 0.81 | 3.78 | 0.63 |
| Kidney | 4.52 | 1.04 | 3.96 | 0.88 | 3.81 | 0.61 | 3.76 | 0.31 |
| Tumor | 13.90 | 3.18 | 42.86 | 14.03 | 46.33 | 8.30 | 61.32 | 19.80 |
| Femur | 2.36 | 0.12 | 1.95 | 0.38 | 1.97 | 0.75 | 2.25 | 0.50 |
| Whole Body Retention | 85.45 | 4.74 | 80.16 | 3.58 | 77.36 | 5.32 | 70.60 | 3.32 |

TABLE ID

BIODISTRIBUTION OF $^{153}$Sm INJECTED AS [$^{153}$Sm(Bz—DTPA)]—F(ab')$_2$—CC-49
% INJECTED DOSE/GRAM
(n = 10)

| Organ | 5 hr AVG | 5 hr STD | 24 hr AVG | 24 hr STD | 48 hr AVG | 48 hr STD | 120 hr AVG | 120 hr STD |
|---|---|---|---|---|---|---|---|---|
| Blood | 15.03 | 1.84 | 2.13 | 0.48 | 0.29 | 0.08 | 0.04 | 0.02 |
| Liver | 7.07 | 0.88 | 7.03 | 1.24 | 6.14 | 0.67 | 5.80 | 1.0 |
| Spleen | 4.50 | 0.97 | 4.22 | 1.15 | 3.65 | 0.62 | 3.24 | 0.42 |
| Kidney | 46.74 | 8.69 | 80.37 | 12.76 | 61.42 | 9.85 | 30.17 | 5.17 |
| Tumor | 15.95 | 3.88 | 18.68 | 5.10 | 15.55 | 2.80 | 6.54 | 1.14 |
| Femur | 2.48 | 0.24 | 1.77 | 0.28 | 2.48 | 0.40 | 2.85 | 0.35 |
| Whole Body Retention | 83.23 | 4.64 | 72.12 | 6.20 | 58.89 | 4.40 | 40.53 | 2.48 |

TABLE IIA

BIODISTRIBUTION OF $^{153}$Sm INJECTED AS [$^{153}$Sm(PA—DOTA)]—IgG—CC-49
% INJECTED DOSE/GRAM
(n = 5)

| Organ | 5.5 hr AVG | 5.5 hr STD | 25 hr AVG | 25 hr STD | 49 hr AVG | 49 hr STD | 121 hr AVG | 121 hr STD |
|---|---|---|---|---|---|---|---|---|
| Blood | 24.65 | 2.89 | 16.18 | 2.10 | 13.22 | 1.08 | 7.34 | 4.23 |
| Liver | 8.25 | 1.14 | 5.92 | 0.41 | 5.59 | 0.52 | 4.16 | 1.03 |
| Spleen | 6.98 | 1.70 | 5.05 | 0.20 | 4.27 | 0.52 | 4.31 | 1.95 |
| Kidney | 4.01 | 0.86 | 3.16 | 0.55 | 3.44 | 0.39 | 3.26 | 0.57 |
| Tumor | 14.31 | *2.00 | 42.81 | 8.83 | 72.59 | 21.53 | 78.36 | 33.29 |
| Femur | 2.69 | 0.41 | 2.02 | 0.32 | 1.69 | 0.37 | 1.44 | 0.69 |
| Tumor Wt. g | 0.27 | 0.29 | 0.34 | 0.26 | 0.16 | 0.13 | 0.28 | 0.15 |

*n = 4

TABLE IIB

BIODISTRIBUTION OF $^{153}$Sm INJECTED AS [$^{153}$Sm(PA—DOTA)]—F(ab')$_2$—CC-49
% INJECTED DOSE/GRAM
(n = 5)

| Organ | 5 hr AVG | 5 hr STD | 24 hr AVG | 24 hr STD | 48 hr AVG | 48 hr STD | 120 hr AVG | 120 hr STD |
|---|---|---|---|---|---|---|---|---|
| Blood | 14.74 | 0.76 | 2.25 | 0.45 | 0.33 | 0.08 | 0.02 | *0.01 |
| Liver | 7.83 | 0.82 | 5.04 | *0.32 | 4.48 | 0.41 | 1.61 | 0.26 |
| Spleen | 4.80 | 0.84 | 3.27 | 0.45 | 3.33 | 0.82 | 1.41 | 0.10 |
| Kidney | 51.28 | 5.83 | 78.78 | 8.40 | 61.91 | 8.17 | 19.79 | 5.75 |
| Tumor | 17.99 | 6.53 | 22.09 | 6.07 | 14.93 | 1.91 | 5.81 | 1.21 |
| Femur | 2.43 | 0.17 | 1.34 | 0.25 | 1.17 | 0.22 | 0.51 | 0.18 |
| Tumor Wt. g | 0.20 | 0.08 | 0.19 | 0.13 | 0.29 | 0.10 | 0.45 | 0.23 |

*n = 4

TABLE IIIA

BIODISTRIBUTION OF $^{153}$Sm INJECTED AS [$^{153}$Sm(BA—DOTA)]—IgG—CC-49
% INJECTED DOSE/GRAM
(n = 5)

| Organ | 5.5 hr AVG | STD | 24 hr AVG | STD | 48 hr AVG | STD | 120 hr AVG | STD |
|---|---|---|---|---|---|---|---|---|
| Blood | 24.89 | 1.29 | 17.53 | 1.79 | 13.61 | 0.53 | 8.68 | 2.94 |
| Liver | 7.53 | 0.79 | 5.46 | *0.62 | 5.35 | *0.40 | 4.26 | *0.58 |
| Spleen | 5.52 | 0.61 | 5.83 | 1.07 | 4.78 | 0.35 | 3.76 | 1.28 |
| Kidney | 3.84 | 0.50 | 3.96 | *0.36 | 3.17 | *0.57 | 3.49 | *0.43 |
| Tumor | 14.41 | 2.96 | 38.65 | 6.45 | 55.84 | 11.43 | 85.26 | 25.70 |
| Femur | 2.54 | 0.34 | 1.81 | 0.35 | 2.08 | 0.30 | 1.17 | 0.48 |
| Tumor Wt. g | 0.34 | 0.22 | 0.13 | 0.04 | 0.20 | 0.06 | 0.20 | 0.15 |

*n = 4

TABLE IIIB

BIODISTRIBUTION OF $^{153}$Sm INJECTED AS [$^{153}$Sm(BA—DOTA)]—F(ab')$_2$—CC-49
% INJECTED DOSE/GRAM
(n = 5)

| Organ | 5 hr AVG | STD | 24 hr AVG | STD | 49 hr AVG | STD | 120 hr AVG | STD |
|---|---|---|---|---|---|---|---|---|
| Blood | 15.62 | *0.86 | 2.42 | 0.42 | 0.28 | 0.08 | 0.03 | 0.01 |
| Liver | 7.69 | 0.71 | 6.18 | 0.82 | 4.22 | 0.88 | 1.56 | 0.25 |
| Spleen | 4.93 | 0.63 | 3.94 | 0.52 | 2.88 | *0.36 | 1.43 | *0.30 |
| Kidney | 50.29 | 4.99 | 77.19 | *3.22 | 60.44 | 7.71 | 24.98 | 2.67 |
| Tumor | 14.58 | 2.24 | 24.28 | 1.81 | 17.65 | 3.25 | 7.39 | 2.54 |
| Femur | 2.13 | 0.18 | 1.36 | 0.15 | 1.03 | 0.28 | 0.68 | 0.35 |
| Tumor Wt. g | 0.17 | 0.02 | 0.12 | 0.07 | 0.17 | 0.06 | 0.12 | 0.10 |

*n = 4

TABLE IVA

BIODISTRIBUTION OF $^{177}$LU INJECTED AS [$^{177}$Lu(PA—DOTA)]—IgG—CC-49
% INJECTED DOSE/GRAM
(n = 5)

| Organ | 5 hr AVG | STD | 24 hr AVG | STD | 48 hr AVG | STD | 121 hr AVG | STD |
|---|---|---|---|---|---|---|---|---|
| Blood | 26.50 | 4.32 | *19.43 | *1.59 | 14.89 | 1.72 | 11.73 | 3.14 |
| Liver | 7.47 | 1.34 | *6.74 | *0.31 | 5.11 | 0.41 | 4.71 | 0.63 |
| Spleen | 6.29 | 1.56 | *5.47 | *1.24 | 4.43 | 0.31 | 5.35 | 1.82 |
| Kidney | 3.86 | *0.85 | *4.13 | *0.45 | 3.13 | *0.30 | 3.57 | 1.15 |
| Tumor | 11.94 | 3.39 | *49.03 | *3.21 | 56.36 | *4.24 | 92.05 | *15.32 |
| Femur | 2.79 | 1.08 | *2.15 | *0.30 | 2.11 | 0.39 | 1.32 | *0.19 |
| Tumor Wt. g | 0.13 | 0.09 | *0.09 | *0.02 | 0.08 | *0.02 | 0.10 | *0.04 |

*n = 4

TABLE IVB

BIODISTRIBUTION OF $^{177}$LU INJECTED AS [$^{177}$Lu(PA—DOTA)]—F(ab')$_2$—CC-49
% INJECTED DOSE/GRAM
(n = 5)

| Organ | 5 hr AVG | STD | 24 hr AVG | STD | 48 hr AVG | STD | 121 hr AVG | STD |
|---|---|---|---|---|---|---|---|---|
| Blood | 12.65 | *0.87 | *2.40 | *0.08 | 0.47 | 0.08 | 0.04 | *0.02 |
| Liver | 5.39 | *0.27 | *5.54 | *0.31 | 3.25 | 0.45 | 1.30 | *0.24 |
| Spleen | 4.21 | 0.95 | *3.60 | *0.55 | 2.60 | 0.74 | 1.33 | 0.27 |
| Kidney | 38.82 | 6.42 | *74.40 | *6.13 | 48.45 | 6.47 | 15.88 | 2.13 |
| Tumor | 10.79 | 2.69 | *19.10 | *2.08 | 15.44 | 2.35 | 4.69 | 0.78 |
| Femur | 2.13 | 0.83 | *1.45 | *0.33 | 0.95 | 0.43 | 0.41 | *0.25 |
| Tumor Wt. g | 0.10 | 0.03 | *0.10 | *0.03 | 0.07 | 0.06 | 0.19 | 0.13 |

*n = 4

TABLE VA

BIODISTRIBUTION OF $^{90}$Y INJECTED AS [$^{90}$Y(PA—DOTA)]—IgG—CC-49
% INJECTED DOSE/GRAM

| Organ | n = 3 5 hr AVG | STD | n = 5 24 hr AVG | STD | n = 5 48 hr AVG | STD | n = 5 120 hr AVG | STD |
|---|---|---|---|---|---|---|---|---|
| Blood | 25.15 | 1.96 | 18.22 | 2.69 | 15.85 | *0.81 | 6.62 | 2.94 |

TABLE VA-continued

BIODISTRIBUTION OF $^{90}$Y INJECTED AS [$^{90}$Y(PA—DOTA)]—IgG—CC-49
% INJECTED DOSE/GRAM

| Organ | n = 3 5 hr AVG | STD | n = 5 24 hr AVG | STD | n = 5 48 hr AVG | STD | n = 5 120 hr AVG | STD |
|---|---|---|---|---|---|---|---|---|
| Liver | 8.25 | 0.42 | 7.61 | 0.77 | 6.52 | 0.96 | 5.68 | 1.26 |
| Spleen | 5.13 | 0.26 | 5.50 | 0.72 | 5.66 | *0.38 | 4.19 | 0.88 |
| Kidney | 3.04 | 0.58 | 4.35 | 1.06 | 3.66 | 0.60 | 2.47 | 0.33 |
| Tumor | 12.45 | 0.79 | 44.73 | **1.43 | 68.41 | *5.48 | 70.32 | 21.34 |
| Femur | 2.05 | 0.15 | 1.81 | 0.54 | 1.79 | *0.11 | 1.04 | 0.45 |

*n = 4
**n = 3

TABLE VB

BIODISTRIBUTION OF $^{90}$Y INJECTED AS
[$^{90}$Y(PA—DOTA)]—F(ab')$_2$—CC-49
% INJECTED DOSE/GRAM
n = 5

| Organ | 5 hr AVG | STD | 24 hr AVG | STD | 48 hr AVG | STD | 120 hr AVG | STD |
|---|---|---|---|---|---|---|---|---|
| Blood | 13.87 | 1.19 | 2.22 | 0.46 | 0.31 | *0.03 | 0.04 | 0.02 |
| Liver | 6.98 | 0.84 | 4.13 | *0.42 | 3.01 | 0.33 | 1.56 | 0.32 |
| Spleen | 4.27 | 0.35 | 3.44 | *0.49 | 2.54 | 0.71 | 1.33 | 0.54 |
| Kidney | 44.60 | 5.52 | 65.40 | 5.92 | 42.31 | 4.67 | 12.36 | 2.60 |
| Tumor | 13.08 | *0.88 | 22.44 | 4.77 | 17.84 | 5.09 | 5.83 | 0.12 |
| Femur | 1.42 | 0.22 | 1.12 | 0.14 | 0.39 | 0.18 | 0.38 | 0.12 |

*n = 4

TABLE VIA

BIODISTRIBUTION OF $^{153}$Sm INJECTED AS
[$^{153}$Sm(MeO—BA—DOTA)]—IgG—CC-49
% INJECTED DOSE/GRAM

| Organ | n = 5 5 hr AVG | STD | n = 5 24 hr AVG | STD | n = 5 48 hr AVG | STD | n = 4 120 hr AVG | STD |
|---|---|---|---|---|---|---|---|---|
| Blood | 21.06 | *0.75 | 14.57 | 1.18 | 13.98 | 0.78 | 9.49 | 1.06 |
| Liver | 9.00 | 1.93 | 6.22 | 0.68 | 6.32 | 0.41 | 4.34 | 0.27 |
| Spleen | 5.39 | 1.40 | 4.00 | 0.64 | 4.69 | 0.93 | 4.53 | 0.41 |
| Kidney | 3.48 | *0.24 | 3.23 | 0.41 | 3.47 | 0.45 | 3.47 | 0.19 |
| Tumor | 18.00 | 8.91 | 41.64 | 3.37 | 58.34 | 5.78 | 69.26 | 21.92 |
| Femur | 2.54 | 0.27 | 1.94 | 0.32 | 2.05 | 0.29 | 1.29 | 0.16 |

*n = 4

TABLE VIB

BIODISTRIBUTION OF $^{153}$Sm INJECTED AS
[$^{153}$Sm(MeO—BA—DOTA)]—F(ab')$_2$—CC-49
% INJECTED DOSE/GRAM
n = 5

| Organ | n = 5 5 hr AVG | STD | n = 5 24 hr AVG | STD | n = 4 48 hr AVG | STD | n = 5 120 hr AVG | STD |
|---|---|---|---|---|---|---|---|---|
| Blood | 12.98 | **0.36 | 2.13 | 0.37 | 0.31 | *0.03 | 0.05 | 0.03 |
| Liver | 6.58 | **0.16 | 6.77 | 1.13 | 4.62 | 0.27 | 2.46 | 0.55 |
| Spleen | 3.95 | 0.57 | 3.53 | 0.76 | 2.59 | 0.40 | 2.18 | 0.68 |
| Kidney | 47.07 | 5.85 | 74.16 | 8.03 | 47.68 | 6.29 | 24.25 | 2.74 |
| Tumor | 12.59 | 3.96 | 17.30 | 1.68 | 12.33 | *0.80 | 5.21 | *0.63 |
| Femur | 2.61 | 0.30 | 1.61 | 0.31 | 0.90 | 0.03 | 0.68 | **0.10 |

*n = 3
**n = 4

TABLE VIIA

BIODISTRIBUTION OF $^{153}$Sm INJECTED AS
[$^{153}$Sm(PA—DOTMA)]—IgG—CC-49
% INJECTED DOSE/GRAM
n = 5

| Organ | 5 hr AVG | STD | 24 hr AVG | STD | 48 hr AVG | STD | 120 hr AVG | STD |
|---|---|---|---|---|---|---|---|---|
| Blood | 23.00 | 1.11 | 15.58 | 1.37 | 11.78 | 0.36 | 8.98 | 0.91 |
| Liver | 7.71 | 0.51 | 6.68 | 1.16 | 4.98 | 0.32 | 4.72 | 0.69 |
| Spleen | 6.05 | 1.03 | 5.28 | 0.45 | 3.66 | 0.35 | 3.72 | 0.53 |

TABLE VIIA-continued

BIODISTRIBUTION OF $^{153}$Sm INJECTED AS
[$^{153}$Sm(PA—DOTMA)]—IgG—CC-49
% INJECTED DOSE/GRAM
n = 5

| Organ | 5 hr AVG | STD | 24 hr AVG | STD | 48 hr AVG | STD | 120 hr AVG | STD |
|---|---|---|---|---|---|---|---|---|
| Kidney | 3.68 | *0.23 | 4.07 | 0.41 | 3.95 | *0.15 | 3.17 | 0.86 |
| Tumor | 10.40 | 2.10 | 31.85 | *2.52 | 44.70 | 10.03 | 66.45 | 13.60 |
| Femur | 1.94 | 0.20 | 1.66 | 0.11 | 1.49 | 1.10 | 1.22 | 0.08 |

*n = 4

TABLE VIIB

BIODISTRIBUTION OF $^{153}$Sm INJECTED AS
[$^{153}$Sm(PA—DOTMA)]—F(ab')$_2$—CC-49
% INJECTED DOSE/GRAM
n = 5

| Organ | 5 hr AVG | STD | 24 hr AVG | STD | 48 hr AVG | STD | 120 hr AVG | STD |
|---|---|---|---|---|---|---|---|---|
| Blood | 12.85 | 1.06 | 1.84 | 0.13 | 0.38 | 0.09 | 0.07 | 0.02 |
| Liver | 6.12 | 0.52 | 5.36 | 0.49 | 3.65 | 0.65 | 1.93 | 0.32 |
| Spleen | 4.08 | 0.37 | 2.88 | 0.31 | 2.09 | 0.62 | 0.92 | *0.13 |
| Kidney | 50.28 | 5.26 | 58.59 | 5.63 | 45.29 | 7.04 | 14.85 | *0.66 |
| Tumor | 11.85 | 2.23 | 14.27 | 1.02 | 15.26 | 2.83 | 4.90 | 2.01 |
| Femur | 1.77 | 0.06 | 1.06 | 0.13 | 0.96 | 0.28 | 0.79 | 0.24 |

*n = 4

TABLE VIIIA

| Organ | 24 hr AVG | STD | 48 hr AVG | STD | 7 day AVG | STD | 14 day AVG | STD | 21 day AVG | STD |
|---|---|---|---|---|---|---|---|---|---|---|

BIODISTRIBUTION OF $^{177}$Lu INJECTED AS [$^{177}$Lu(PA—DOTMA)]—IgG—CC-49
% INJECTED DOSE/GRAM
n = 5

| Organ | 24 hr AVG | STD | 48 hr AVG | STD | 7 day AVG | STD | 14 day AVG | STD | 21 day AVG | STD |
|---|---|---|---|---|---|---|---|---|---|---|
| Blood | 31.35 | 2.66 | 30.25 | *0.93 | 22.47 | 0.71 | 14.13 | 1.05 | 9.88 | 0.83 |
| Liver | 10.01 | 0.46 | 11.22 | 1.47 | 8.61 | 0.79 | 6.76 | 0.67 | 5.41 | 1.39 |
| Spleen | 10.13 | 1.16 | 10.91 | *0.67 | 10.79 | *0.36 | 8.09 | 0.98 | 6.03 | 0.55 |
| Kidney | 6.52 | 2.06 | 6.14 | 0.76 | 5.21 | 0.97 | 3.44 | 0.43 | 2.17 | 0.22 |
| Femur | 3.97 | 0.45 | 4.53 | 0.38 | 2.84 | 0.16 | 2.36 | 0.23 | 1.67 | 0.30 |

BIODISTRIBUTION OF $^{177}$Lu INJECTED AS [$^{177}$Lu(PA—DOTA)]—IgG—CC-49
% INJECTED DOSE/GRAM
n = 5

| Organ | 24 hr AVG | STD | 48 hr AVG | STD | 7 day AVG | STD | 14 day AVG | STD | 21 day AVG | STD |
|---|---|---|---|---|---|---|---|---|---|---|
| Blood | 30.23 | *0.57 | 28.42 | 2.02 | 21.96 | 1.03 | 14.73 | 0.48 | 8.85 | 1.03 |
| Liver | 11.54 | 1.34 | 10.84 | 1.27 | 9.20 | 1.04 | 6.69 | 0.48 | 6.07 | 1.41 |
| Spleen | 10.86 | 1.47 | 11.55 | 1.64 | 10.62 | 1.25 | 9.25 | 1.10 | 6.64 | 1.43 |
| Kidney | 7.67 | 1.83 | 5.80 | 0.59 | 4.98 | 0.50 | 3.27 | *0.19 | 2.60 | 0.64 |
| Femur | 3.65 | 0.62 | 3.64 | 0.51 | 2.98 | 0.41 | 2.50 | 0.20 | 1.71 | *0.17 |

*n = 4

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What we claim is:

1. A conjugate comprising of a compound of the formula:

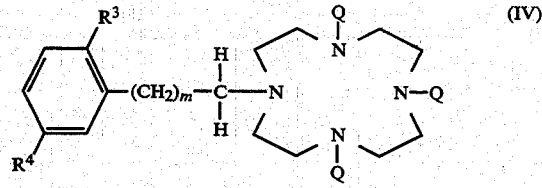

(IV)

wherein:
each Q is CHR$^5$CO$_2$R;
each R is hydrogen;
m is 0;
R$^3$ is selected from the group consisting of methoxy and hydroxy;
R$^4$ is selected from the group consisting of amino, and isothiocyanato;
each R$^5$ is hydrogen; or
a pharmaceutically acceptable salt thereof;
complexed with an ion of a metal selected from the group consisting of La, Ce, Pr, Nd, Pm, Sm, Eu, Gd, Tb, Dy, Ho, Er, Tm, Yb, Lu, Y and Sc; and covalently attached to an antibody or antibody fragment.

2. A conjugate of claim 1 wherein the conjugate has the metal ion selected from the group consisting of Sm, Ho, Lu and Y.

3. A conjugate of claim 1 wherein the conjugate has the metal ion selected from the group consisting of $^{153}$Sm, $^{166}$Ho, $^{90}$Y, $^{149}$Pm, $^{159}$Gd, $^{140}$La, $^{177}$Lu, $^{175}$Yb, $^{47}$S and $^{142}$Pr.

4. A conjugate of claim 1 wherein the conjugate has the metal ion selected from the group consisting of $^{153}$Sm, $^{166}$Ho, $^{177}$Lu and $^{90}$Y.

5. A conjugate of claim 1 wherein the antibody or antibody fragment is a monoclonal antibody or fragment thereof.

6. A conjugate of claim 5 wherein the antibody or antibody fragment is selected from the group consisting of CC-49, CC-49 F(ab')$_2$, CC-83 and CC-83 F(ab')$_2$.

7. A conjugate of claim 1 wherein the compound of the conjugate is 1-(2-methoxy-5-aminobenzyl)-1,4,7,10-tetraazacyclododecane-4,7,10-triacetic acid.

8. A conjugate of claim 1 wherein the compound of the conjugate is 1-(2-hydroxy-5-aminobenzyl)-1,4,7,10-tetraazacyclododecane-4,7,10-triacetic acid.

9. A pharmaceutical formulation comprising a conjugate of claim 1 with a pharmaceutically acceptable carrier.

10. A pharmaceutical formulation comprising a conjugate of claim 3 with a pharmaceutically acceptable carrier.

11. A method for the diagnosis of cancer in a mammal which comprises administering to said mammal an amount effective for the diagnosis of cancer of a formulation comprising a conjugate of a compound of the formula

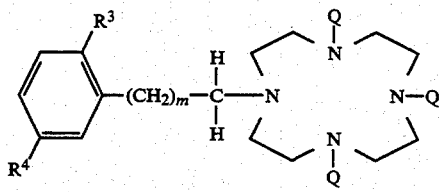

wherein:
each Q is $CHR^5CO_2R$;
each R is hydrogen;
m is 0;
$R^3$ is selected from the group consisting of methoxy and hydroxy;
$R^4$ is selected from the group consisting of amino, and isothiocyanato;
each $R^5$ is hydrogen; or
a pharmaceutically acceptable salt thereof;
complexed with an ion of a metal selected from the group consisting of La, Ce, Pr, Nd, Pm, Sm, Eu, Gd, Tb, Dy, Ho, Er, Tm, Yb, Lu, Y and Sc; and covalently attached to an antibody or antibody fragment; with a pharmaceutically acceptable carrier.

12. A method of claim 11 wherein the conjugate has the metal ion selected from the group consisting of Sm, Ho, Lu and Y.

13. A method of claim 11 wherein the conjugate has the metal ion selected from the group consisting of $^{153}$Sm, $^{166}$Ho, $^{90}$Y, $^{149}$Pm, $^{159}$Gd, $^{140}$La, $^{177}$Lu, $^{175}$Yb, $^{47}$Sc and $^{142}$Pr.

14. A method of claim 11 wherein the conjugate has the metal ion selected from the group consisting of $^{153}$Sm, $^{166}$Ho, $^{177}$Lu and $^{90}$Y.

15. A method of claim 11 wherein the antibody or antibody fragment is a monoclonal antibody or fragment thereof.

16. A method of claim 15 wherein the antibody or antibody fragment is selected from the group consisting of CC-49, CC-49 F(ab')$_2$, CC-83 and CC-83 F(ab')$_2$.

17. A method of claim 11 wherein the compound of the conjugate is 1-(2-methoxy-5-aminobenzyl)-1,4,7,10-tetraazacyclododecane-4,7,10-triacetic acid.

18. A method of claim 11 wherein the compound of the conjugate is 1-(2-hydroxy-5-aminobenzyl)-1,4,7,10-tetraazacyclododecane-4,7,10-triacetic acid.

19. A conjugate comprising of a compound of the formula:

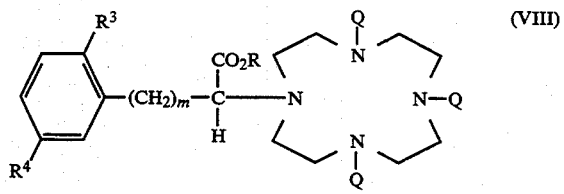

wherein:
each Q is $CHR^5CO_2R$;
each R is hydrogen;
m is 0;
$R^3$ is selected from the group consisting of methoxy and hydroxyl
$R^4$ is selected from the group consisting of amino, and isothiocyanato;
each $R^5$ is hydrogen; or
a pharmaceutically acceptable salt thereof;
complexed with an ion of a metal selected from the group consisting of La, Ce, Pr, Nd, Pm, Sm, Eu, Gd, Tb, Dy, Ho, Er, Tm, Yb, Lu, Y and Sc; and covalently attached to an antibody or antibody fragment.

20. A conjugate of claim 19 wherein the conjugate has the metal ion selected from the group consisting of Sm, Ho, Lu and Y.

21. A conjugate of claim 19 wherein the conjugate has the metal ion selected from the group consisting of $^{153}$Sm, $^{166}$Ho, $^{90}$Y, $^{149}$Pm, $^{159}$Gd, $^{140}$La, $^{177}$Lu, $^{175}$Yb, $^{47}$Sc and $^{142}$Pr.

22. A conjugate of claim 19 wherein the conjugate has the metal ion selected from the group consisting of $^{153}$Sm, $^{166}$Ho, $^{177}$Lu and $^{90}$Y.

23. A conjugate of claim 19 wherein the antibody or antibody fragment is a monoclonal antibody or fragment thereof.

24. A conjugate of claim 23 wherein the antibody or antibody fragment is selected from the group consisting of CC-49, CC-49 F(ab')$_2$, CC-83 and CC-83 F(ab')$_2$.

25. A conjugate of claim 19 wherein the compound of the conjugate is α-(2-methoxy-5-aminophenyl)-1,4,7,10-tetraazacyclododecane-1,4,7,10-tetraacetic acid, tetraammonium salt.

26. A conjugate of claim 19 wherein the compound of the conjugate is α-(2-methoxy-5-isothiocyanatophenyl)-1,4,7,10-tetraazacyclododecane-1,4,7,10-tetraacetic acid, tetraammonium salt.

27. A conjugate of claim 19 wherein the conjugate has as its compound α-(2-methoxy-5-isothiocyanatophenyl)-1,4,7,10-tetraazacyclododecane-1,4,7,10-tetraacetic acid, tetraammonium salt, the metal ion is $^{153}$Sm, and the antibody or antibody fragment is selected from the group consisting of CC-49, CC-49 F(ab')$_2$, CC-83 and CC-83 F(ab')$_2$.

28. A conjugate of claim 19 wherein the conjugate has as its compound α-(2-methoxy-5-aminophenyl)-1,4,7,10-tetraazacyclododecane-1,4,7,10-tetraacetic acid, tetraammonium salt, the metal ion is $^{153}$Sm, and the antibody or antibody fragment is selected from the group consisting of CC-49, CC-49 F(ab')$_2$, CC-83 and CC-83 F(ab')$_2$.

29. A pharmaceutical formulation comprising a conjugate of claim 19 pharmaceutically acceptable carrier.

30. A pharmaceutical formulation comprising a conjugate of claim 21 pharmaceutically acceptable carrier.

31. A method for the diagnosis of cancer in a mammal which comprises administering to said mammal an amount effective for the diagnosis of cancer of a formulation comprising a conjugate of a compound of the formula

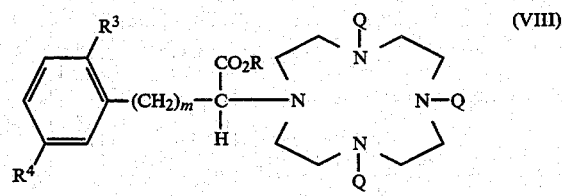

wherein:
each Q is $CHR^5CO_2R$;
each R is hydrogen;
m is 0;
$R^3$ is selected from the group consisting of methoxy and hydroxy;
$R^4$ is selected from the group consisting of amino, and isothiocyanato;
each $R^5$ is hydrogen; or
a pharmaceutically acceptable salt thereof;
complexed with an ion of a metal selected from the group consisting of La, Ce, Pr, Nd, Pm, Sm, Eu, Gd, Tb, Dy, Ho, Er, Tm, Yb, Lu, Y and Sc; and
covalently attached to an antibody or antibody fragment; with a pharmaceutically acceptable carrier.

32. A method of claim 31 wherein the conjugate has the metal ion selected from the group consisting of Sm, Ho, Lu and Y.

33. A method of claim 31 wherein the conjugate has the metal ion selected from the group consisting of $^{153}Sm$, $^{166}Ho$, $^{90}Y$, $^{149}Pm$, $^{159}Gd$, $^{140}La$, $^{177}Lu$, $^{175}Yb$, $^{47}Sc$ and $^{142}Pr$.

34. A method of claim 31 wherein the conjugate has the metal ion selected from the group consisting of $^{153}Sm$, $^{166}Ho$, $^{177}Lu$ and $^{90}Y$.

35. A method of claim 31 wherein the antibody or antibody fragment is a monoclonal antibody or fragment thereof.

36. A method of claim 31 wherein the antibody or antibody fragment is selected from the group consisting of CC-49, CC-49 F(ab')$_2$, CC-83 and CC-83 F(ab')$_2$.

37. A method of claim 31 wherein the compound of the conjugate is α-(2-methoxy-5-aminophenyl)-1,4,7,10-tetraazacyclododecane-1,4,7,10-tetraacetic acid, tetraammonium salt.

38. A method of claim 31 wherein the compound of the conjugate is α-(2-methoxy-5-isothiocyanatophenyl)-1,4,7,10-tetraazacyclododecane-1,4,7,10-tetraacetic acid, tetraammonium salt.

39. A method of claim 31 wherein the conjugate has as its compound α-(2-methoxy-5-isothiocyanatophenyl)-1,4,7,10-tetraazacyclododecane-1,4,7,10-tetraacetic acid, tetraammonium salt, the metal ion is $^{153}Sm$, and the antibody or antibody fragment is selected from the group consisting of CC-49, CC-49 F(ab')$_2$, CC-83 and CC-83 F(ab')$_2$.

40. A method of claim 31 wherein the conjugate has as its compound α-(2-methoxy-5-aminophenyl)-1,4,7,10-tetraazacyclododecane-1,4,7,10-tetraacetic acid, tetraammonium salt, the metal ion is $^{153}Sm$, and the antibody or antibody fragment is selected from the group consisting of CC-49, CC-49 F(ab')$_2$, CC-83 and CC-83 F(ab')$_2$.

* * * * *

UNITED STATES PATENT AND TRADEMARK OFFICE
CERTIFICATE OF CORRECTION

PATENT NO. : 5,435,990

DATED : July 25, 1995

INVENTOR(S) : R.C. Cheng, W.A. Fordyce, W.F. Goeckeler, W.J. Kruper, D.A. Wilson, S. Baughman, R.K. Frank, J.R. Garlich, G.E. Kiefer, K. McMillan, J. Simon It is certified that error appears in the above-indentified patent and that said Letters Patent is hereby corrected as shown below:

Cover page, item [54] and col. 1, line 1, delete "CONGUGATES" and insert -- CONJUGATES --.

Cover page, line 2, in the Inventors Information, delete "Goeckleler" and insert --Goeckeler--.

Cover page, line 10, in the Inventors Information, delete "Braughman" and insert --Baughman--.

Column 76, line 65, delete " $^{47}$S " and insert -- $^{47}$Sc --.

Signed and Sealed this

Thirty-first Day of December, 1996

Attest:

BRUCE LEHMAN

*Attesting Officer*    *Commissioner of Patents and Trademarks*